(12) United States Patent
Lo et al.

(10) Patent No.: US 9,512,480 B2
(45) Date of Patent: Dec. 6, 2016

(54) DETERMINATION OF THE DEPTH COVERAGE OF THE FETAL GENOME

(71) Applicant: The Chinese University of Hong Kong, Sha Tin (CN)

(72) Inventors: Yuk Ming Dennis Lo, Kowloon (CN); Kwan Chee Chan, Kowloon (CN); Wai Kwun Rossa Chiu, Shatin (CN); Charles Cantor, Del Mar, CA (US)

(73) Assignees: The Chinese University of Hong Kong, Shatin (CN); Sequenom Inc., San Diego, CA (US)

( * ) Notice: Subject to any disclaimer, the term of this patent is extended or adjusted under 35 U.S.C. 154(b) by 754 days.

(21) Appl. No.: 13/895,308

(22) Filed: May 15, 2013

(65) Prior Publication Data
US 2013/0323731 A1  Dec. 5, 2013

Related U.S. Application Data

(62) Division of application No. 12/940,993, filed on Nov. 5, 2010, now Pat. No. 8,467,976.

(60) Provisional application No. 61/258,567, filed on Nov. 5, 2009, provisional application No. 61/259,075, filed on Nov. 6, 2009, provisional application No. 61/381,854, filed on Sep. 10, 2010.

(51) Int. Cl.
| | |
|---|---|
| G06F 19/10 | (2011.01) |
| G11C 17/00 | (2006.01) |
| C12Q 1/68 | (2006.01) |
| G06F 19/18 | (2011.01) |
| G06F 19/24 | (2011.01) |
| G06F 19/22 | (2011.01) |

(52) U.S. Cl.
CPC .......... *C12Q 1/6876* (2013.01); *C12Q 1/6827* (2013.01); *G06F 19/18* (2013.01); *G06F 19/22* (2013.01); *G06F 19/24* (2013.01); *Y10T 436/143333* (2015.01)

(58) Field of Classification Search
None
See application file for complete search history.

(56) References Cited

U.S. PATENT DOCUMENTS

| | | | |
|---|---|---|---|
| 6,258,540 | B1 | 7/2001 | Lo |
| 6,927,028 | B2 | 8/2005 | Dennis et al. |
| 7,727,720 | B2 | 6/2010 | Dhallan |
| 2005/0164241 | A1 | 7/2005 | Hahn |
| 2006/0252071 | A1 | 11/2006 | Lo |
| 2007/0202525 | A1 | 8/2007 | Quake |
| 2008/0318235 | A1 | 12/2008 | Handyside |
| 2009/0029377 | A1 | 1/2009 | Lo |
| 2009/0087847 | A1 | 4/2009 | Lo |
| 2010/0112590 | A1 | 5/2010 | Lo |
| 2011/0178719 | A1 | 7/2011 | Rabinowitz et al. |
| 2011/0276277 | A1 | 11/2011 | Lo |
| 2011/0288780 | A1 | 11/2011 | Rabinowitz et al. |

FOREIGN PATENT DOCUMENTS

| | | |
|---|---|---|
| RU | 2200761 C1 | 3/2003 |
| WO | 2004/078999 | 9/2004 |
| WO | 2004/079011 A1 | 9/2004 |
| WO | 2007/028155 | 3/2007 |
| WO | 2007/075836 A2 | 7/2007 |
| WO | 2007/100911 | 9/2007 |
| WO | 2009/013492 | 1/2009 |

OTHER PUBLICATIONS

Armstrong, J., et al., "Prenatal Diagnosis in Rett Syndrome," Fetal Diagnosis and Therapy, 2002, vol. 17, pp. 200-204.
Office Action mailed Sep. 9, 2014 in Australian Patent Application No. 2013203446, 6 pages.
Office Action mailed Sep. 16, 2014 in Australian Patent Application No. 2013203448, 6 pages.
Zhou, et al., "Counting alleles to predict recurrence of early-stage colorectal cancers," The Lancet, Jan. 2002, vol. 359, Issue 9302, pp. 219-225.
Diehl, et al., "Detection and quantification of mutations in the plasma of patients with colorectal tumors," PNAS, Nov. 2005, vol. 102, No. 45, pp. 16368-16373.
Office Action mailed Feb. 25, 2014 in U.S. Appl. No. 13/937,162, 11 pages.
Ding, Chunming, et al., "MS Analysis of Single-Nucleotide Differences in Circulating Nucleic Acids: Application to Noninvasive Prenatal Diagnosis," Jul. 20, 2004, Proceedings of the National Academy of Sciences of the United States of America, vol. 101, No. 29, pp. 10762-10767.
Reed, W., et al., "Non-Invasive Determination of the Paternal HLA Haplotype of a Fetus Using Kinetic PCR to Detect Fetal Microchimerism in Maternal Plasma," Mar. 2, 2002, Bone Marrow Transplantation, vol. 29, No. 6, pp. 527-529.

(Continued)

*Primary Examiner* — John S Brusca
(74) *Attorney, Agent, or Firm* — Kilpatrick Townsend & Stockton LLP; David B. Raczkowski

(57) ABSTRACT

Systems, methods, and apparatus for determining at least a portion of fetal genome are provided. DNA fragments from a maternal sample (maternal and fetal DNA) can be analyzed to identify alleles at certain loci. The amounts of DNA fragments of the respective alleles at these loci can be analyzed together to determine relative amounts of the haplotypes for these loci and determine which haplotypes have been inherited from the parental genomes. Loci where the parents are a specific combination of homozygous and heterozygous can be analyzed to determine regions of the fetal genome. Reference haplotypes common in the population can be used along with the analysis of the DNA fragments of the maternal sample to determine the maternal and paternal genomes. Determination of mutations, a fractional fetal DNA concentration in a maternal sample, and a proportion of coverage of a sequencing of the maternal sample can also be provided.

19 Claims, 45 Drawing Sheets
(31 of 45 Drawing Sheet(s) Filed in Color)

(56) References Cited

OTHER PUBLICATIONS

Chiu, Rossa, W.K., et al., "Non-Invasive Prenatal Diagnosis by Single Molecule Counting Technologies," Jul. 1, 2009, Trends in Genetics, vol. 25, No. 7, pp. 324-331.
Lun, Fiona, M.F., et al., "Noninvasive Prenatal Diagnosis of Monogenic Diseases by Digital Size Selection and Relative Mutation Dosage on DNA in Maternal Plasma," Dec. 16, 2008, Proceedings of the National Academy of Sciences of the United States of America, vol. 105, No. 50, pp. 19920-19925.
Fan, H., Christina, et al., "Noninvasive Diagnosis of Fetal Aneuploidy by Shotgun Sequencing DNA from Maternal Blood," Oct. 21, 2008, Proceedings of the National Academy of Sciences of the United States of America, vol. 105, No. 42, pp. 16266-16271.
Chiu, Rossa, W.K., et al., "Noninvasive Prenatal Diagnosis of Fetal Chromosomal Aneuploidy by Massively Parallel Genomic Sequencing of DNA in Maternal Plasma," Dec. 23, 2008, Proceedings of the National Academy of Sciences of the United States of America, vol. 105, No. 51, pp. 20458-20463.
Larrabee, Paige, B., et al., "Microarray Analysis of Cell-Free Fetal DNA in Amniotic Fluid: A Prenatal Molecular Karyotype," Sep. 1, 2004, American Journal of Human Genetics, vol. 75, No. 3, pp. 485-491.
Li, Ying, et al., "Size Separation of Circulatory DNA in Maternal Plasma Permits Ready Detection of Fetal DNA Polymorphisms," Jun. 1, 2004, Clinical Chemistry, American Association for Clinical Chemistry, vol. 50, No. 6, pp. 1002-1011.
Lo, Y. M. Dennis, et al., "Digital PCR for the Molecular Detection of Fetal Chromosomal Aneuploidy," Aug. 2007, Proceesings of the National Academy of Sciences of the United States of America, vol. 104, No. 32, pp. 13116-13121.
International Search Report and Written Opinion, mailed Apr. 20, 2011, PCT Application No. PCT/US2010/055655, International Filing Date Nov. 6, 2010, 20 pages.
International Search Report and Written Opinion, mailed Feb. 23, 2011, PCT/EP2010/066935, International Filing Date Nov. 5, 2010, pp. 13 pages.
Amicucci, P., et al., "Prenatal Diagnosis of Myotonic Dystrophy Using Fetal DNA Obtained from Maternal Plasma," Clin Chem, 2000, vol. 46, No. 2, pp. 301-302.
Batzer. M. A., et al., "Enhanced evolutionary PCR using oligonucleotides with inosine at the 3'-terminus," Nucleic Acid Res., Jul. 12, 1991, vol. 19, p. 5081.
Bentley, D.R., et al., "Accurate whole human genome sequencing using reversible terminator chemistry," Nature, Nov. 2008; vol. 456, pp. 53-59.
Botezatu, I., et al., "Genetic Analysis of DNA Excreted in Urine: a New Approach for Detecting Specific Genomic DNA Sequences from Cells Dying in an Organism," Clin Chem, 2000; vol. 46, pp. 1078-1084.
Chan, K.C.A., et al.; "Hypermethylated RASSFIA in Maternal Plasma: A Universal Fetal DNA Marker that Improves the Reliability of Noninvasive Prenatal Diagnosis"; Clin Chem, 2006, vol. 52, pp. 2211-2218.
Chan, K.C.A., et al., "Size Distributions of Maternal and Fetal DNA in Maternal Plasma," Clin Chem, 2004; vol. 50, pp. 88-92.
Chiu, R.W.K., et al., "Prenatal exclusion of .beta. thalassaemia major by examination of maternal plasma," Lancet, Sep. 28, 2002; vol. 360, pp. 998-1000.
Clark, A.G., "Inference of Haplotypes from PCR-amplified Samples of Diploid Populations," Mol Biol Evol, 1990, vol. 7, pp. 111-122, [retrieved on Oct. 25, 2012], <URL: http://mbe.oxfordjournals.org/>.
Clarke, J., et al., "Continuous base identification for single-molecule nanopore DNA sequencing," Nat Nanotechnol, [online], Apr. 2009; vol. 4, pp. 265-270.
Ding, C., et al., "Direct molecular haplotyping of long-range genomic DNA with M1-PCR," Proc Natl Acad Sci USA, Jun. 24, 2003; vol. 100, pp. 7449-7453.

Eid, J., et al., "Real-Time DNA Sequencing from Single Polymerase Molecules," Science, Jan. 2, 2009, vol. 323, pp. 133-138.
Geiss, G.K., et al., "Direct multiplexed measurement of gene expression with color-coded probe pairs," Nat Biotechnol, Mar. 2008, vol. 26, pp. 317-325.
Gnirke, A., et al., "Solution hybrid selection with ultra-long oligonucleotides for massively parallel targeted sequencing," Nat Biotechnol, Feb. 2009, vol. 27, No. 2, pp. 182-189.
Harris, T. D., et al.; "Single-Molecule DNA Sequencing of a Viral Genome"; Science, Apr. 4, 2008, vol. 320, pp. 106-109.
Karoui, N.E., et al., "Getting more from digital SNP data," Statist Med, 2006, vol. 25, pp. 3124-3133.
Lien, S., et al., "Single-Sperm Typing," Curr Protoc Hum Genet, 2002; Chapter 1, Unit 1.6, 18 pages.
Li, R., et al.,"SOAP: short oligonucleotide alignment program," Bioinformatics, [online], 2008; vol. 24, No. 5, pp. 713-714, [retrieved on Oct. 25, 2012], <URL:http://bioinformatics.oxfordjournals.org/>.
Li, R., et al., "SOAP2: an improved ultrafast tool for short read alignment," Bioinformatics, [online], 2009; vol. 25, No. 15, pp. 1966-1967, [retrieved on Oct. 25, 2012], <URL: http://bioinformatics.oxfordjournals.org/>.
Lo, et al., "Presence of Fetal DNA in Maternal Plasma and Serum," Lancet, 1997, vol. 350, pp. 485-487.
Lo, Y.M. Dennis, et al.; "Plasma Placental RNA Allelic Ratio Permits Noninvasive Prenatal Chromosomal Aneuploidy Detection;" Nature Medicine; Feb. 2007; vol. 13, No. 2; pp. 218-223.
Lo, et al., "Quantitative Analysis of Fetal DNA in Maternal Plasma and Serum: Implications for Noninvasive Prenatal Diagnosis," Am J. Hum Genet, 1998, vol. 62, pp. 768-775.
Lo, Y.M.D., et al., "Direct haplotype determination by double ARMS: specificity, sensitivity and genetic applications," Nucleic Acids Res, 1991; vol. 19, No. 13, pp. 3561-3567.
Lun, Fiona, M. F., et al.; "Microfluidics Digital PCR Reveals a Higher Than Expected Fraction of Fetal DNA in Maternal Plasma;" Clin Chem, Oct. 1, 2008, vol. 54; No. 10; pp. 1664-1672.
Margulies, Marcel et al.; "Genome sequencing in microfabricated high-density picolitre reactors"; Nature, Sep. 15, 2005, vol. 437, pp. 376-380.
McKernan, K.J., et al., "Sequence and structural variation in a human genome uncovered by short-read, massively parallel ligation sequencing using two-base encoding," Genome Res, [online], 2009; vol. 19, pp. 1527-1541, [retrieved on Oct. 25, 2012], <URL: genome.cshlp.org>.
Michalatos-Beloin, S., et al., "Molecular haplotyping of genetic markers 10 kb apart by allele-specific long-range PCR," Nucleic Acids Res, 1996; vol. 24, pp. 4841-4843.
Ohtsuka, E., et al., "An Alternative Approach to Deoxyoligonucleotides as Hybridization Probes by Insertion of Deoxyinosine at Ambiguous Codon Positions," J. Biol. Chem., Mar. 10, 1985, vol. 260, pp. 2605-2608.
Poon, Leo, L. M., et al.; "Differential DNA Methylation between Fetus and Mother as a Strategy for Detecting Fetal DNA in Maternal Plasma"; Clin Chem, 2002, vol. 48, No. 1, pp. 35-41.
Rossolini, G.M., et al., "Use of deoxyinosine-containing primers vs degenerate primers for polymerase chain reaction based on ambiguous sequence information," Mol. Cell. Probes, 1994, vol. 8, pp. 91-98.
Ruano, G., et al., "Haplotype of multiple polymorphisms resolved by enzymatic amplification of single DNA molecules," Proc Natl Acad Sci USA, Aug. 1990; vol. 87, pp. 6296-6300.
Saito, et al., "Prenatal DNA Diagnosis of a Single-gene Disorder From Maternal Plasma," Lancet, 2000, vol. 356, p. 1170.
Salem, R.M., et al., "A comprehensive literature review of haplotyping software and methods for use with unrelated individuals," Hum Genomics, 2005; vol. 2, No. 1, pp. 39-66.
Smirnova, A., et al., "A novel strategy for defining haplotypes by selective depletion using restriction enzymes," Immunogenetics, 2007; vol. 59, pp. 93-98.
Tewhey, R., et al., "Microdroplet-based PCR enrichment for large-scale targeted sequencing," Nat Biotechnol, Nov. 2009, vol. 27, No. 11, pp. 1025-1031.

(56) References Cited

OTHER PUBLICATIONS

Tong, Yu, K., et al.; "Noninvasive Prenatal Detection of Fetal Trisomy 18 by Epigenetic Allelic Ratio Analysis in Maternal Plasma: Theoretical and Empirical Considerations;" Clin Chem, Oct. 13, 2006, vol. 52; No. 12; pp. 2194-2202.

Xiao, M., et al., "Determination of Haplotypes from Single DNA Molecules: A Method for Single-Molecule Barcoding," Hum Mutat, 2007; vol. 28, pp. 913-921.

Zhou, W., et al., "Counting alleles reveals a connection between chromosome 18q loss and vascular invasion," Nat Biotechnol, Jan. 2001, vol. 19, pp. 78-81.

Wright, Caroline, F., et al., "The use of cell-free fetal nucleic acids in maternal blood For non-invasive prenatal diagnosis," Human Reproductive Update, 2009, vol. 15, No. 1, pp. 139-151.

Gonzalez-Gonzalez, Cristina, et al., "Application of Fetal DNA Detection in Maternal Plasma: A Prenatal Diagnosis Unit Experience," Journal of Histochemistry & Cytochemistry, 2005, vol. 53, No. 3, pp. 307-314.

Office Action (English Translation) dated Nov. 12, 2013 in ROC Taiwan Patent Application No. 099138291, 4 pages.

Office Action (English Translation) mailed Nov. 26, 2013 in Japanese Patent Application No. 2012-538035, 7 pages.

Patent Examination Report No. 1, mailed Aug. 27, 2013 in Australian Patent Application No. 2010315037, 4 pages.

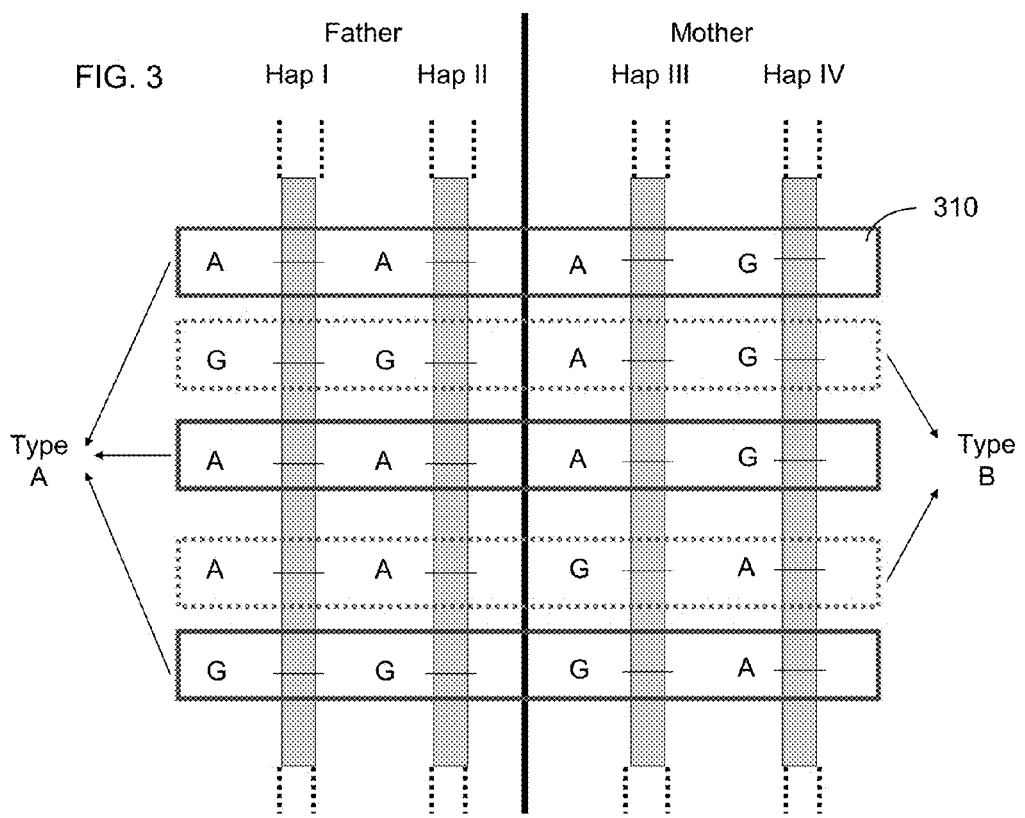

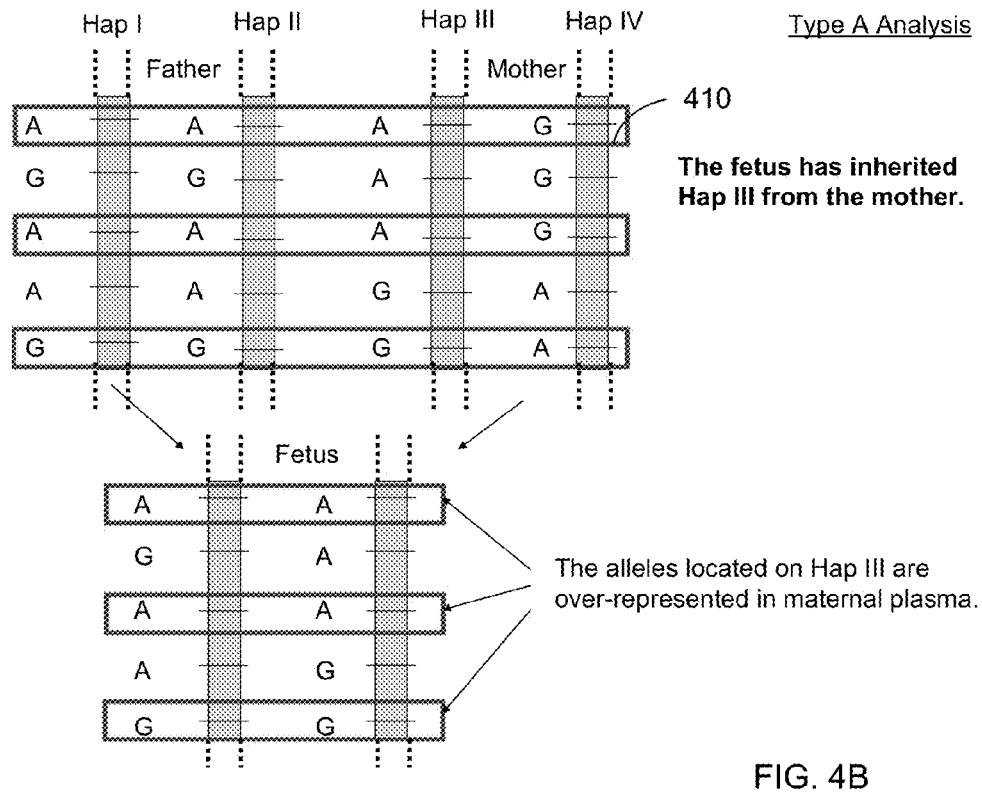
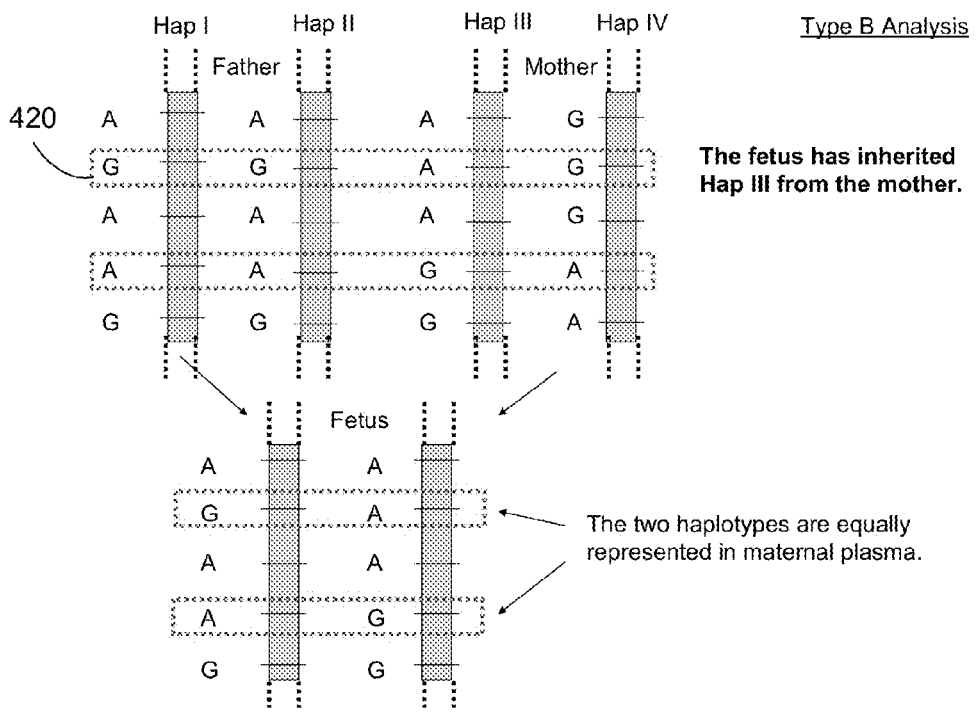

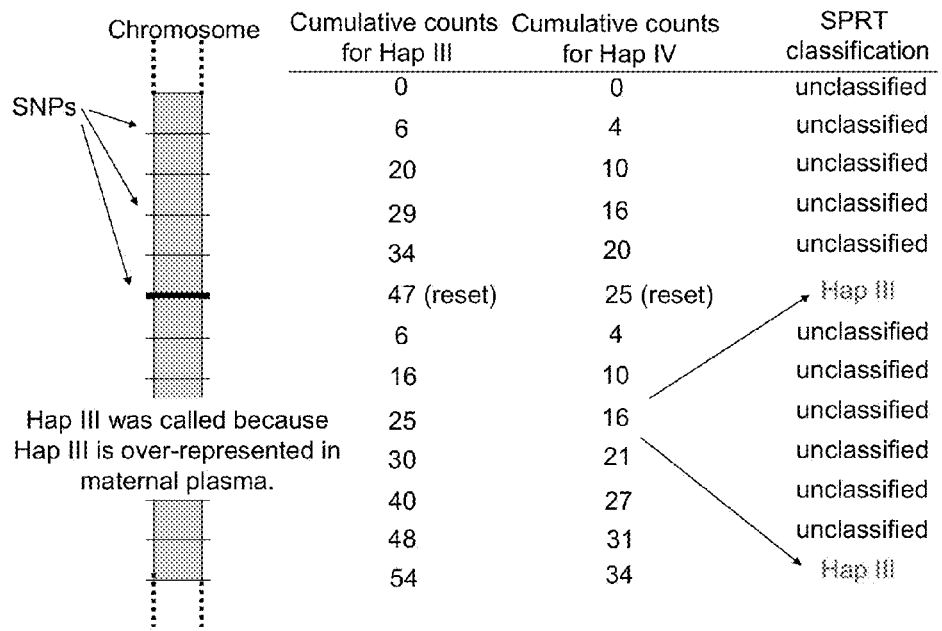
FIG. 5A: SPRT analysis for RHDO
Type A analysis: paternal alleles identical to Hap III
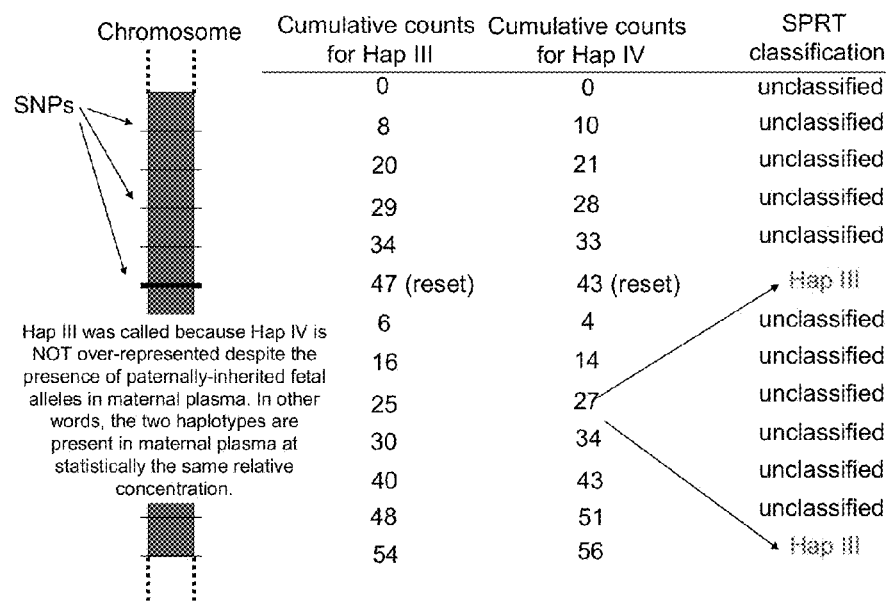
FIG. 5B: SPRT analysis for RHDO
Type B analysis: paternal alleles identical to Hap IV

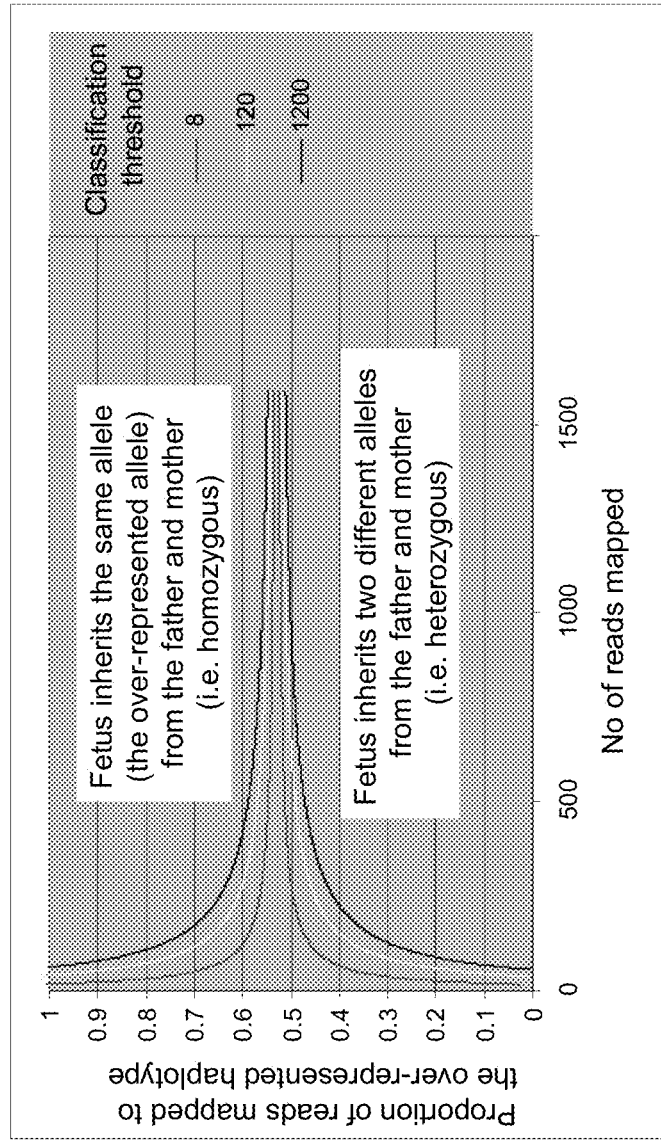
FIG. 6 : Effect of the alteration of classification threshold on SPRT curves (Paternal allele identical to Hap III)

Mut = mutation
WT = wildtype

| Genotype combination | No. of SNPs | Percentage (%) |
|---|---|---|
| Fetus heterozygous | 220,296 | 24.57 |
| Mother homozygous; father heterozygous | 131,037 | 14.61 |
| Mother homozygous; fetus heterozygous | 111,775 | 12.46 |
| Mother homozygous; father heterozygous; fetus heterozygous | 65,875 | 7.35 |
| Mother homozygous; father heterozygous; fetus homozygous | 65,162 | 7.27 |
| Mother homozygous; father homozygous, but with different alleles | 45,900 | 5.12 |
| Total | 896,756 | 100 |

| Flow Cell | Total Raw Read (Million) | Total Aligned Read (Million) | Alignment Rate % |
|---|---|---|---|
| 1 | 265 | 200 | 75.29 |
| 2 | 274 | 206 | 75.22 |
| 3 | 268 | 204 | 75.96 |
| 4 | 254 | 193 | 76.10 |
| 5 | 258 | 196 | 76.02 |
| 6 | 280 | 215 | 76.60 |
| 7 | 272 | 207 | 75.97 |
| 8 | 253 | 192 | 75.80 |
| 9 | 260 | 195 | 75.17 |
| 10 | 266 | 208 | 78.11 |
| 11 | 245 | 188 | 76.68 |
| 12 | 249 | 190 | 76.22 |
| 13 | 250 | 189 | 75.32 |
| 14 | 257 | 192 | 74.79 |
| 15 | 250 | 187 | 75.14 |
| 16 | 243 | 187 | 76.93 |
| 17 | 270 | 200 | 74.25 |
| 18 | 258 | 197 | 76.48 |
| 19 | 258 | 193 | 74.98 |
| 20 | 253 | 193 | 76.31 |

FIG. 26 Fetal DNA concentration estimated from 20 FCs

| Chr. | Father hetero, Mother homo, Fetus hetero (%) | Father homo, Mother homo, Different alleles (%) |
|---|---|---|
| chr1 | 11.83 | 11.92 |
| chr2 | 12.15 | 11.99 |
| chr3 | 11.80 | 11.92 |
| chr4 | 11.89 | 11.84 |
| chr5 | 12.01 | 12.10 |
| chr6 | 12.00 | 11.80 |
| chr7 | 12.14 | 11.75 |
| chr8 | 12.04 | 11.95 |
| chr9 | 11.70 | 11.82 |
| chr10 | 11.57 | 11.75 |
| chr11 | 11.88 | 11.90 |
| chr12 | 12.09 | 11.80 |
| chr13 | 12.39 | 11.94 |
| chr14 | 11.90 | 11.84 |
| chr15 | 11.75 | 11.61 |
| chr16 | 11.93 | 11.36 |
| chr17 | 11.77 | 11.49 |
| chr18 | 11.99 | 11.74 |
| chr19 | 11.77 | 12.02 |
| chr20 | 11.74 | 11.56 |
| chr21 | 11.74 | 11.37 |
| chr22 | 11.81 | 11.34 |
| chrX |  | 12.03 |

Chr: Chromosome
homo: homozygous
hetero: heterozygous

FIG. 27A Proportion of SNPs Covered by Fetal Specific Reads
(Mother and father homozygous but with different alleles)
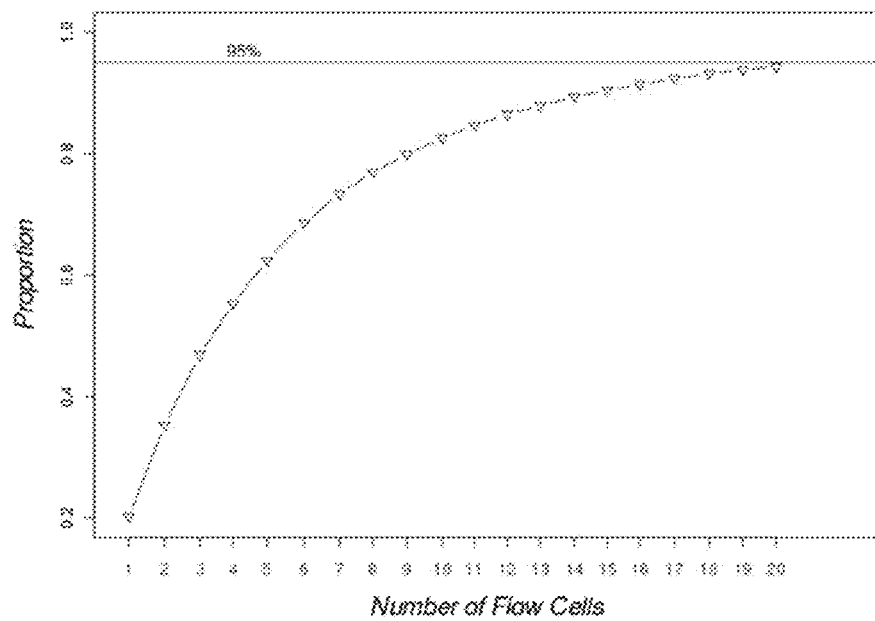
FIG. 27B Proportion of SNPs Covered by Fetal Specific Reads
(Mother and father homozygous but with different alleles)
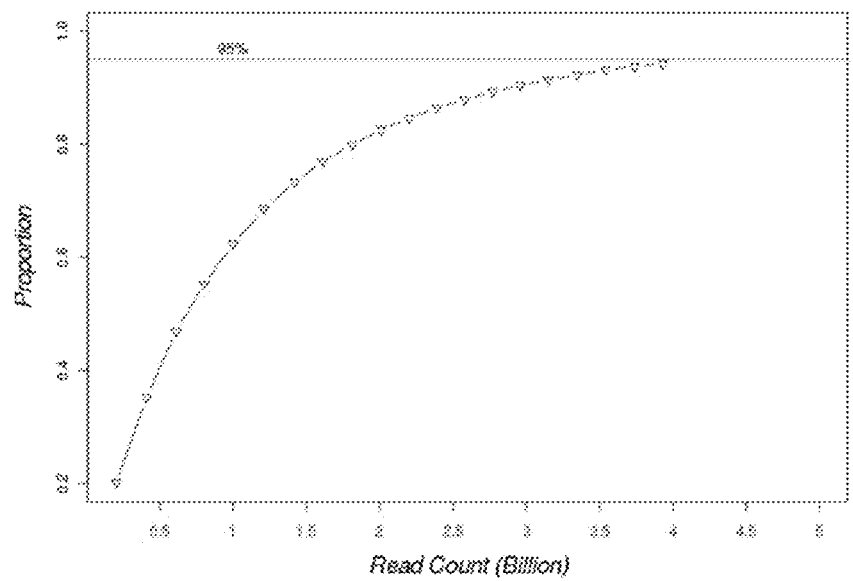

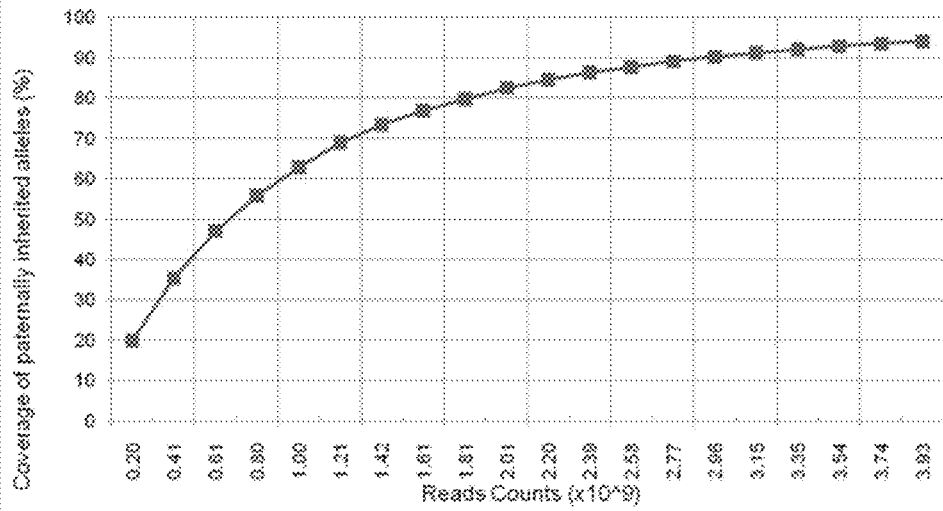
FIG. 28A Correlation between coverage of paternally inherited alleles and read counts (mother homozygous; father heterozygous; fetus heterozygous)
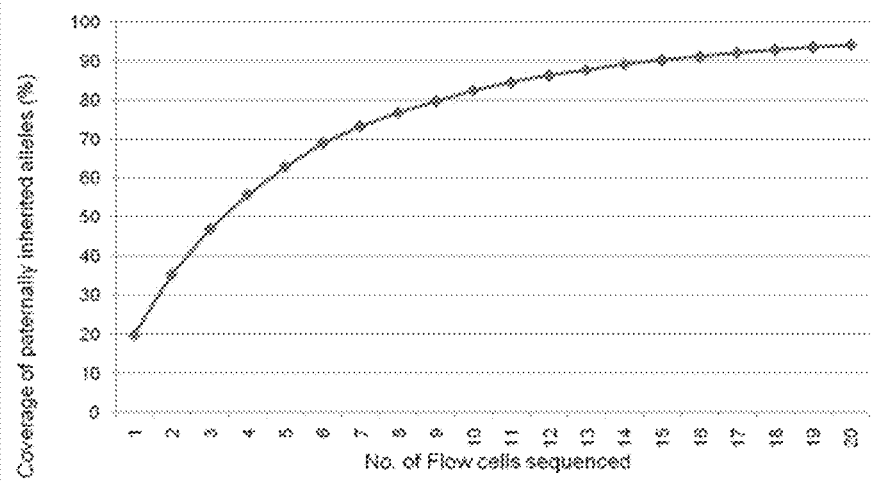
FIG. 28B Correlation between the coverage of paternally inherited alleles and no. of flow cells sequenced (mother homozygous; father heterozygous; fetus heterozygous)

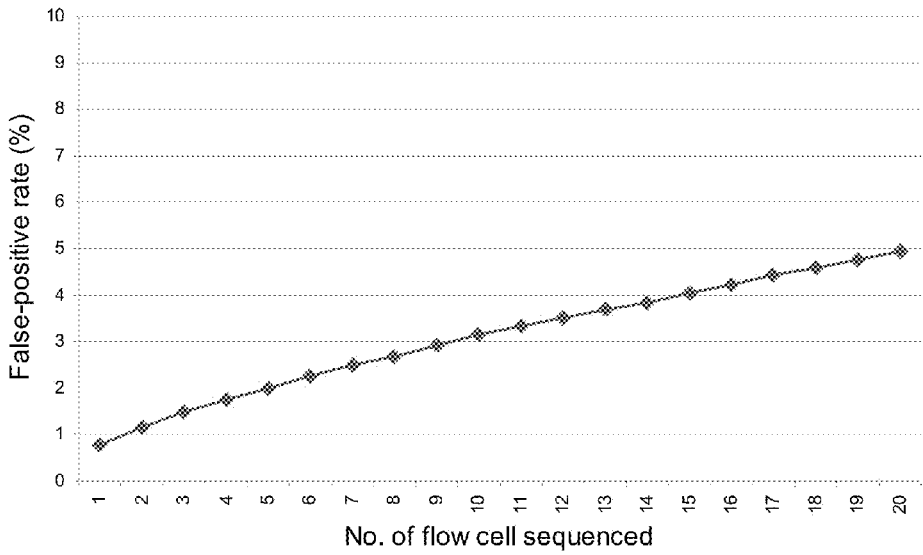
FIG. 29A Correlation between false-positive rate and no. of flow cells sequenced
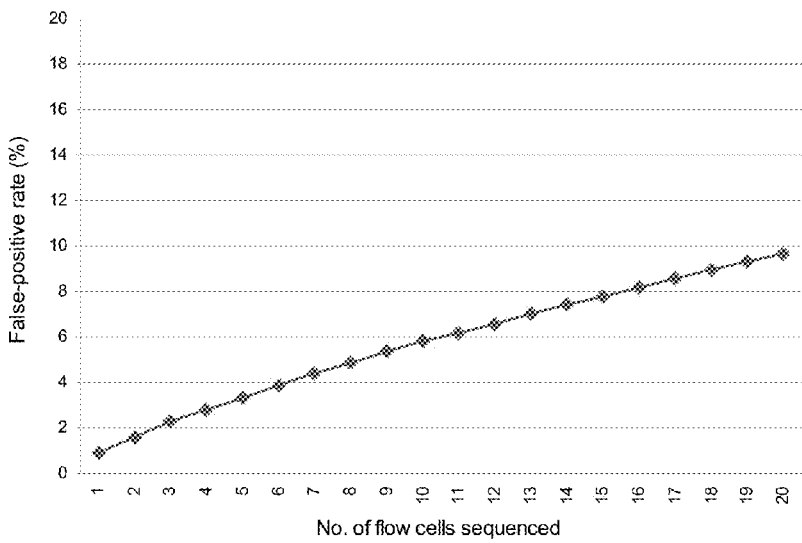
FIG. 29B : Correlation between false-positive rate and the number of flow cells sequenced (Mother homozygous, Father homozygous, with the same allele)

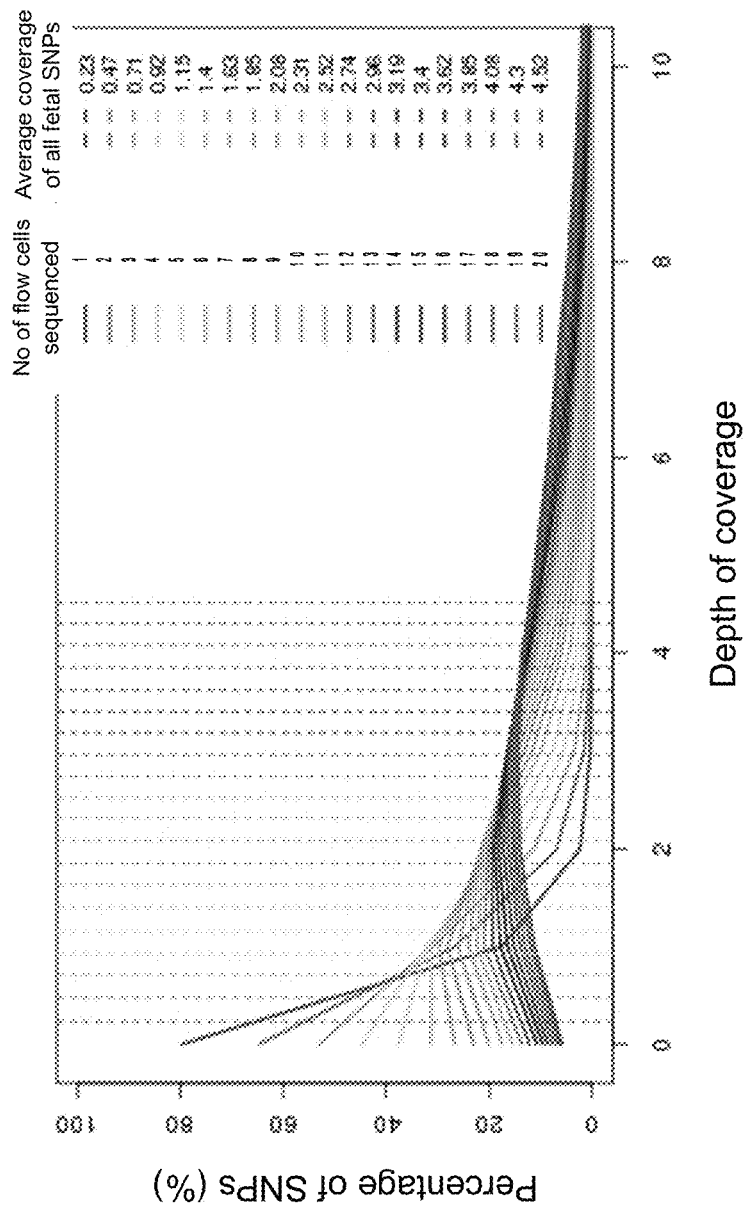
FIG. 30 : Depth of coverage of SNPs with different number of flow cells sequenced FIG. 31 : Accuracy of Type A classification (10 flow cells)

| Chr | Correct classification | | Incorrect classification | | Incorrect for both interlacing analyses | | Total |
|---|---|---|---|---|---|---|---|
| | No. | Percentage | No. | Percentage | No. | Percentage | |
| Chr 1 | 224 | 99.1% | 2 | 0.9% | 0 | 0.0% | 226 |
| Chr 2 | 215 | 96.8% | 7 | 3.2% | 0 | 0.0% | 222 |
| Chr 3 | 176 | 97.2% | 5 | 2.8% | 0 | 0.0% | 181 |
| Chr 4 | 162 | 98.8% | 2 | 1.2% | 0 | 0.0% | 164 |
| Chr 5 | 139 | 99.3% | 1 | 0.7% | 0 | 0.0% | 140 |
| Chr 6 | 170 | 99.4% | 1 | 0.6% | 0 | 0.0% | 171 |
| Chr 7 | 134 | 99.3% | 1 | 0.7% | 0 | 0.0% | 135 |
| Chr 8 | 154 | 98.7% | 2 | 1.3% | 0 | 0.0% | 156 |
| Chr 9 | 134 | 99.3% | 1 | 0.7% | 0 | 0.0% | 135 |
| Chr 10 | 154 | 99.4% | 1 | 0.6% | 0 | 0.0% | 155 |
| Chr 11 | 151 | 98.7% | 2 | 1.3% | 0 | 0.0% | 153 |
| Chr 12 | 136 | 99.3% | 1 | 0.7% | 0 | 0.0% | 137 |
| Chr 13 | 95 | 100.0% | 0 | 0.0% | 0 | 0.0% | 95 |
| Chr 14 | 91 | 100.0% | 0 | 0.0% | 0 | 0.0% | 91 |
| Chr 15 | 76 | 100.0% | 0 | 0.0% | 0 | 0.0% | 76 |
| Chr 16 | 95 | 99.0% | 1 | 1.0% | 0 | 0.0% | 96 |
| Chr 17 | 82 | 100.0% | 0 | 0.0% | 0 | 0.0% | 82 |
| Chr 18 | 67 | 100.0% | 0 | 0.0% | 0 | 0.0% | 67 |
| Chr 19 | 46 | 100.0% | 0 | 0.0% | 0 | 0.0% | 46 |
| Chr 20 | 79 | 97.5% | 2 | 2.5% | 0 | 0.0% | 81 |
| Chr 21 | 45 | 100.0% | 0 | 0.0% | 0 | 0.0% | 45 |
| Chr 22 | 32 | 100.0% | 0 | 0.0% | 0 | 0.0% | 32 |
| Chr X | 103 | 96.3% | 4 | 3.7% | 0 | 0.0% | 107 |
| Total | 2760 | 98.8% | 33 | 1.2% | 0 | 0.0% | 2793 |

FIG. 32  Accuracy of Type B classification (10 flow cells)

| Chr | Correct classification | | Incorrect classification | | Incorrect for both interlacing analyses | | Total |
|---|---|---|---|---|---|---|---|
| | No. | Percentage | No. | Percentage | No. | Percentage | |
| Chr 1 | 210 | 97.2% | 6 | 2.8% | 0 | 0.0% | 216 |
| Chr 2 | 230 | 97.9% | 5 | 2.1% | 0 | 0.0% | 235 |
| Chr 3 | 163 | 99.4% | 1 | 0.6% | 0 | 0.0% | 164 |
| Chr 4 | 127 | 100.0% | 0 | 0.0% | 0 | 0.0% | 127 |
| Chr 5 | 182 | 98.9% | 2 | 1.1% | 0 | 0.0% | 184 |
| Chr 6 | 155 | 96.9% | 5 | 3.1% | 0 | 0.0% | 160 |
| Chr 7 | 115 | 97.5% | 3 | 2.5% | 0 | 0.0% | 118 |
| Chr 8 | 160 | 98.8% | 2 | 1.2% | 0 | 0.0% | 162 |
| Chr 9 | 123 | 98.4% | 2 | 1.6% | 0 | 0.0% | 125 |
| Chr 10 | 130 | 97.0% | 4 | 3.0% | 0 | 0.0% | 134 |
| Chr 11 | 129 | 97.7% | 3 | 2.3% | 0 | 0.0% | 132 |
| Chr 12 | 118 | 100.0% | 0 | 0.0% | 0 | 0.0% | 118 |
| Chr 13 | 90 | 97.8% | 2 | 2.2% | 0 | 0.0% | 92 |
| Chr 14 | 83 | 97.6% | 2 | 2.4% | 0 | 0.0% | 85 |
| Chr 15 | 75 | 98.7% | 1 | 1.3% | 0 | 0.0% | 76 |
| Chr 16 | 80 | 94.1% | 5 | 5.9% | 0 | 0.0% | 85 |
| Chr 17 | 50 | 100.0% | 0 | 0.0% | 0 | 0.0% | 50 |
| Chr 18 | 71 | 97.3% | 2 | 2.7% | 0 | 0.0% | 73 |
| Chr 19 | 48 | 100.0% | 0 | 0.0% | 0 | 0.0% | 48 |
| Chr 20 | 80 | 100.0% | 0 | 0.0% | 0 | 0.0% | 80 |
| Chr 21 | 27 | 100.0% | 0 | 0.0% | 0 | 0.0% | 27 |
| Chr 22 | 44 | 97.8% | 1 | 2.2% | 0 | 0.0% | 45 |
| Chr X | 118 | 97.5% | 3 | 2.5% | 0 | 0.0% | 121 |
| Total | 2608 | 98.2% | 49 | 1.8% | 0 | 0.0% | 2657 |

FIG. 33 : Accuracy of Type A SPRT analysis

| chr | Single block classification | | | Two consecutive blocks algorithm | | |
|---|---|---|---|---|---|---|
| | Correct (%) | Incorrect (%) | Total | Correct (%) | Incorrect (%) | Total |
| 1 | 314 (99.1%) | 3 (0.9%) | 317 | 309 (100%) | 0 (0.0%) | 309 |
| 2 | 305 (99.3%) | 2 (0.7%) | 307 | 301 (100%) | 0 (0.0%) | 301 |
| 3 | 240 (99.6%) | 1 (0.4%) | 241 | 237 (100%) | 0 (0.0%) | 237 |
| 4 | 218 (99.5%) | 1 (0.5%) | 219 | 215 (100%) | 0 (0.0%) | 215 |
| 5 | 203 (100%) | 0 (0.0%) | 203 | 201 (100%) | 0 (0.0%) | 201 |
| 6 | 240 (98.0%) | 5 (2.0%) | 245 | 237 (98.8%) | 3 (1.3%) | 240 |
| 7 | 182 (98.9%) | 2 (1.1%) | 184 | 179 (100%) | 0 (0.0%) | 179 |
| 8 | 217 (99.5%) | 1 (0.5%) | 218 | 214 (100%) | 0 (0.0%) | 214 |
| 9 | 177 (99.4%) | 1 (0.6%) | 178 | 174 (100%) | 0 (0.0%) | 174 |
| 10 | 217 (99.1%) | 2 (0.9%) | 219 | 213 (100%) | 0 (0.0%) | 213 |
| 11 | 205 (100%) | 0 (0.0%) | 205 | 203 (100%) | 0 (0.0%) | 203 |
| 12 | 193 (99.5%) | 1 (0.5%) | 194 | 190 (100%) | 0 (0.0%) | 190 |
| 13 | 133 (100%) | 0 (0.0%) | 133 | 132 (100%) | 0 (0.0%) | 132 |
| 14 | 125 (100%) | 0 (0.0%) | 125 | 124 (100%) | 0 (0.0%) | 124 |
| 15 | 103 (100%) | 0 (0.0%) | 103 | 102 (100%) | 0 (0.0%) | 102 |
| 16 | 133 (98.5%) | 2 (1.5%) | 135 | 129 (100%) | 0 (0.0%) | 129 |
| 17 | 104 (100%) | 0 (0.0%) | 104 | 102 (100%) | 0 (0.0%) | 102 |
| 18 | 95 (97.9%) | 2 (2.1%) | 97 | 91 (100%) | 0 (0.0%) | 91 |
| 19 | 67 (100%) | 0 (0.0%) | 67 | 65 (100%) | 0 (0.0%) | 65 |
| 20 | 112 (100%) | 0 (0.0%) | 112 | 110 (100%) | 0 (0.0%) | 110 |
| 21 | 60 (100%) | 0 (0.0%) | 60 | 59 (100%) | 0 (0.0%) | 59 |
| 22 | 39 (100%) | 0 (0.0%) | 39 | 38 (100%) | 0 (0.0%) | 38 |
| X | 156 (98.7%) | 2 (1.3%) | 158 | 152 (100%) | 0 (0.0%) | 152 |
| Total | 3838 (99.4%) | 25 (0.6%) | 3863 | 3777 (99.9%) | 3 (0.1%) | 3780 |

FIG. 34 : Accuracy of Type B SPRT analysis

| chr | Single block classification | | | Two consecutive blocks algorithm | | |
|---|---|---|---|---|---|---|
| | Correct (%) | Incorrect (%) | Total | Correct (%) | Incorrect (%) | Total |
| 1 | 267 (98.2%) | 5 (1.8%) | 272 | 262 (100%) | 0 (0.0%) | 262 |
| 2 | 283 (99.0%) | 3 (1.0%) | 286 | 278 (100%) | 0 (0.0%) | 278 |
| 3 | 222 (98.2%) | 4 (1.8%) | 226 | 216 (100%) | 0 (0.0%) | 216 |
| 4 | 175 (98.9%) | 2 (1.1%) | 177 | 171 (100%) | 0 (0.0%) | 171 |
| 5 | 255 (99.6%) | 1 (0.4%) | 256 | 252 (100%) | 0 (0.0%) | 252 |
| 6 | 195 (99.0%) | 2 (1.0%) | 197 | 192 (100%) | 0 (0.0%) | 192 |
| 7 | 155 (97.5%) | 4 (2.5%) | 159 | 150 (100%) | 0 (0.0%) | 150 |
| 8 | 211 (100%) | 0 (0.0%) | 211 | 209 (100%) | 0 (0.0%) | 209 |
| 9 | 162 (99.4%) | 1 (0.6%) | 163 | 160 (100%) | 0 (0.0%) | 160 |
| 10 | 172 (96.6%) | 6 (3.4%) | 178 | 167 (98.2%) | 3 (1.8%) | 170 |
| 11 | 171 (99.4%) | 1 (0.6%) | 172 | 168 (100%) | 0 (0.0%) | 168 |
| 12 | 156 (99.4%) | 1 (0.6%) | 157 | 153 (100%) | 0 (0.0%) | 153 |
| 13 | 119 (98.3%) | 2 (1.7%) | 121 | 117 (99.2%) | 1 (0.8%) | 118 |
| 14 | 116 (98.3%) | 2 (1.7%) | 118 | 115 (99.1%) | 1 (0.9%) | 116 |
| 15 | 101 (100%) | 0 (0.0%) | 101 | 100 (100%) | 0 (0.0%) | 100 |
| 16 | 115 (94.3%) | 7 (5.7%) | 122 | 107 (99.1%) | 1 (0.9%) | 108 |
| 17 | 67 (98.5%) | 1 (1.5%) | 68 | 65 (100%) | 0 (0.0%) | 65 |
| 18 | 92 (100%) | 0 (0.0%) | 92 | 90 (100%) | 0 (0.0%) | 90 |
| 19 | 57 (100%) | 0 (0.0%) | 57 | 55 (100%) | 0 (0.0%) | 55 |
| 20 | 95 (100%) | 0 (0.0%) | 95 | 93 (100%) | 0 (0.0%) | 93 |
| 21 | 39 (100%) | 0 (0.0%) | 39 | 38 (100%) | 0 (0.0%) | 38 |
| 22 | 59 (100%) | 0 (0.0%) | 59 | 58 (100%) | 0 (0.0%) | 58 |
| X | 142 (99.3%) | 1 (0.7%) | 143 | 139 (100%) | 0 (0.0%) | 139 |
| Total | 3426 (98.8%) | 43 (1.2%) | 3469 | 3355 (99.8%) | 6 (0.2%) | 3361 |

FIG. 35A

Reads with CD41/42 paternally inherited mutation

Count = 10

```
CGGGTATTGTCGTAGTCCTCACCTGTCTAGGGGTTTCCTGAGTTGGAGAC
CGGGTATTGTCGTAGTCCTCACCTGTCTAGGGGTTTCCTGAGTTGGAGAC
 GGGTATTGTCGTAGTCCTCACCTGTCTAGGGGTTTCCTGAGTTGGAGACC
  GGTATTGTCGTAGTCCTCACCTGTCTAGGGGTTTCCTGAGTTGGAGACCC
         CGTAGTCCTCACCTGTCTAGGGGTTTCCTGAGTTGGAGACCCAGGTTCCC
          GTAGTCCTCACCTGTCTAGGGGTTTCCTGAGTTGGAGACCCAGGTTCCCA
                  CTGTCTAGGGGTTTCCTGAGTTGGAGACCCAGGTTCCCATCTGGTGGTCG
                   TGTCTAGGGGTTTCCTGAGTTGGAGACCCAGGTTCCCATCTGGTGGTCGT
                            TTCCTGAGTGGGAGACCCAGGTTCCCATCTGGTGGTCGTCGGATTCCCAC
                                GTGGGAGACCCAGGTTCCCATCTGGTGGTCGTCGGATTCCCACCCTTTTA
```

FIG. 35B

Reads with wildtype sequence in CD41/42

Count = 62

Thus, % mutant = 10/72 = 0.1389

FIG. 36: Type A analysis on the β-globin cluster on chromosome 11

| Chr | dbSNPid | Loc | Genotype | | | | | HapIII Count | HapIV Count | HapIII Cum Count | HapIV Cum Count | Classification |
|---|---|---|---|---|---|---|---|---|---|---|---|---|
| | | | Father | Mother | Fetus | Hap III | Hap IV | | | | | |
| chr 11 | | 5204905 | | | | Thalassemia beta-globin nt -28 mutation | | | | | | |
| chr11 | rs10742583 | 5205217 | TT | CT | TT | T | C | 22 | 26 | 22 | 26 | Unclassified |
| chr11 | rs10742584 | 5205346 | TT | CT | TT | T | C | 21 | 12 | 43 | 38 | Unclassified |
| chr11 | rs1003586 | 5205946 | GG | AG | GG | G | A | 24 | 11 | 67 | 49 | Unclassified |
| chr11 | rs6578588 | 5208827 | GG | AG | GG | G | A | 43 | 38 | 110 | 87 | Unclassified |
| chr11 | rs3759076 | 5213765 | CC | CT | CC | C | T | 29 | 0 | 139 | 87 | Unclassified |
| chr11 | rs10837643 | 5214614 | AA | AT | AA | A | T | 23 | 11 | 162 | 98 | Unclassified |
| chr11 | rs4283007 | 5215066 | TT | AT | TT | T | A | 53 | 36 | 215 | 134 | Hap III |

FIG. 37 : Type B analysis on the beta-globin cluster on chromosome 11

| Chr | dbSNPid | Loc | Father | Mother | Fetus | Hap III | Hap IV | Hap III Count | Hap IV Count | Hap III Cum Count | Hap IV Cum Count | Classification |
|---|---|---|---|---|---|---|---|---|---|---|---|---|
| chr 11 | | 5204905 | | | | | Thalassemia beta-globin nt -28 mutation | | | | | |
| chr11 | rs12275403 | 5286913 | CC | CG | CG | G | C | 19 | 23 | 19 | 23 | Unclassified |
| chr11 | rs7926089 | 5289019 | CC | CT | CT | T | C | 13 | 21 | 32 | 44 | Unclassified |
| chr11 | rs12365420 | 5289330 | GG | GT | GT | T | G | 5 | 12 | 37 | 56 | Unclassified |
| chr11 | rs4910747 | 5294746 | CC | AC | AC | A | C | 27 | 36 | 64 | 92 | Unclassified |
| chr11 | rs6578604 | 5299185 | AA | AG | AG | G | A | 15 | 18 | 79 | 110 | Unclassified |
| chr11 | rs10837814 | 5301704 | GG | AG | AG | A | G | 39 | 45 | 118 | 155 | Unclassified |
| chr11 | rs4910550 | 5302436 | GG | AG | AG | A | G | 15 | 22 | 133 | 177 | Unclassified |
| chr11 | rs2723381 | 5304451 | TT | CT | CT | C | T | 38 | 34 | 171 | 211 | Unclassified |
| chr11 | rs6578606 | 5306671 | GG | CG | CG | C | G | 40 | 31 | 211 | 242 | Unclassified |
| chr11 | rs3824950 | 5588548 | CC | CT | CT | T | C | 59 | 66 | 270 | 308 | Unclassified |
| chr11 | rs10838441 | 5601579 | GG | CG | CG | C | G | 20 | 10 | 290 | 318 | Unclassified |
| chr11 | rs11038628 | 5645516 | CC | CT | CT | T | C | 65 | 5 | 355 | 323 | Hap III |

| Genomic coordinates of the SNP | Maternal alleles on | | Counts for alleles on | | Cumulative counts for alleles on | | SPRT classification |
|---|---|---|---|---|---|---|---|
| | Hap I | Hap II | Hap I | Hap II | Hap I | Hap II | |
| 3251050 | A | G | 22 | 15 | 22 | 15 | Unclassified |
| 3251284 | G | A | 14 | 10 | 36 | 25 | Unclassified |
| 3251791 | A | G | 18 | 11 | 54 | 36 | Hap I |
| 9865342 | A | G | 5 | 3 | 5 | 3 | Unclassified |
| 9872792 | A | G | 7 | 5 | 12 | 8 | Unclassified |
| 9874947 | G | C | 1 | 3 | 13 | 11 | Unclassified |
| 15242479 | G | A | 17 | 5 | 30 | 16 | Hap I |
| 15710521 | G | A | 1 | 2 | 1 | 2 | Unclassified |
| 15710672 | A | G | 13 | 13 | 14 | 15 | Unclassified |
| 21895385 | C | T | 15 | 3 | 29 | 18 | Unclassified |
| 22149641 | T | C | 5 | 3 | 34 | 21 | Hap I |
| 22201527 | A | C | 11 | 10 | 11 | 10 | Unclassified |
| 23806924 | C | T | 20 | 9 | 31 | 19 | Unclassified |
| 31134605 | A | G | 2 | 1 | 33 | 20 | Hap I |
| 32413115 | C | T | 6 | 8 | 6 | 8 | Unclassified |
| 32473184 | G | A | 8 | 9 | 14 | 17 | Unclassified |
| 35730716 | A | G | 17 | 14 | 31 | 31 | Unclassified |
| 35903375 | C | T | 7 | 9 | 38 | 40 | Unclassified |
| 35903407 | G | A | 6 | 2 | 44 | 42 | Unclassified |
| 35917535 | T | G | 6 | 7 | 50 | 49 | Unclassified |
| 43475980 | T | G | 7 | 16 | 57 | 65 | Unclassified |
| 47351305 | A | G | 7 | 6 | 64 | 71 | Unclassified |
| 48561783 | A | G | 5 | 1 | 69 | 72 | Unclassified |
| 50676020 | C | T | 19 | 15 | 88 | 87 | Unclassified |
| 53601143 | A | G | 8 | 10 | 96 | 97 | Unclassified |
| 54854802 | T | C | 9 | 3 | 105 | 100 | Unclassified |
| 74921254 | C | A | 3 | 3 | 108 | 103 | Unclassified |
| 78102680 | A | C | 5 | 3 | 113 | 106 | Unclassified |
| 78313644 | C | T | 40 | 24 | 153 | 130 | Hap I |

FIG. 38A

| Genomic coordinates of the SNP | Maternal alleles on | | Counts for alleles on | | Cumulative counts for alleles on | | SPRT classification |
|---|---|---|---|---|---|---|---|
| | Hap I | Hap II | Hap I | Hap II | Hap I | Hap II | |
| 84236666 | A | G | 3 | 0 | 3 | 0 | Unclassified |
| 84249796 | A | G | 29 | 12 | 32 | 12 | Hap I |
| 100273993 | T | C | 16 | 10 | 16 | 10 | Unclassified |
| 100494847 | A | G | 13 | 5 | 29 | 15 | Hap I |
| 106283058 | G | A | 5 | 8 | 5 | 8 | Unclassified |
| 106283131 | G | A | 13 | 12 | 18 | 20 | Unclassified |
| 107283614 | G | A | 10 | 4 | 28 | 24 | Unclassified |
| 107335295 | T | G | 5 | 1 | 33 | 25 | Unclassified |
| 114785655 | C | T | 11 | 7 | 44 | 32 | Unclassified |
| 117584169 | G | A | 8 | 2 | 52 | 34 | Hap I |
| 118473031 | T | C | 3 | 5 | 3 | 5 | Unclassified |
| 118488464 | C | T | 5 | 15 | 8 | 20 | Unclassified |
| 119474561 | A | T | 5 | 4 | 13 | 24 | Unclassified |
| 123022716 | C | A | 17 | 12 | 30 | 36 | Unclassified |
| 128506731 | C | G | 4 | 3 | 34 | 39 | Unclassified |
| 130047404 | C | T | 4 | 1 | 38 | 40 | Unclassified |
| 130243499 | C | T | 13 | 19 | 51 | 59 | Unclassified |
| 134814366 | C | T | 12 | 8 | 63 | 67 | Unclassified |
| 134818744 | G | A | 27 | 18 | 90 | 85 | Unclassified |
| 134823671 | C | T | 5 | 9 | 95 | 94 | Unclassified |
| 138507378 | A | T | 7 | 3 | 102 | 97 | Unclassified |
| 138695073 | A | G | 10 | 3 | 112 | 100 | Unclassified |
| 144713436 | C | T | 10 | 16 | 122 | 116 | Unclassified |
| 149577161 | A | G | 11 | 5 | 133 | 121 | Unclassified |
| 150888835 | C | A | 11 | 11 | 144 | 132 | Unclassified |
| 152383349 | T | C | 8 | 3 | 152 | 135 | Hap I |
| 152694738 | C | T | 1 | 0 | 1 | 0 | Unclassified |
| 152848587 | G | A | 4 | 6 | 5 | 6 | Unclassified |

FIG. 38B

| Case | Total no of informative SNPs | Average sequencing depth for each SNP (fold) | Fraction fetal DNA concentration (%) | Total no of SPRT classifications | No of correct classifications | No of incorrect classifications |
|---|---|---|---|---|---|---|
| PW226 | 57 | 17.6 | 19.4 | 9 | 9 | 0 |
| PW263 | 62 | 15.8 | 18.4 | 4 | 4 | 0 |
| PW316 | 58 | 18.5 | 17.4 | 2 | 2 | 0 |
| PW370 | 54 | 18.9 | 11.5 | 1 | 1 | 0 |
| PW431 | 46 | 19.6 | 15.3 | 2 | 2 | 0 |

FIG. 39

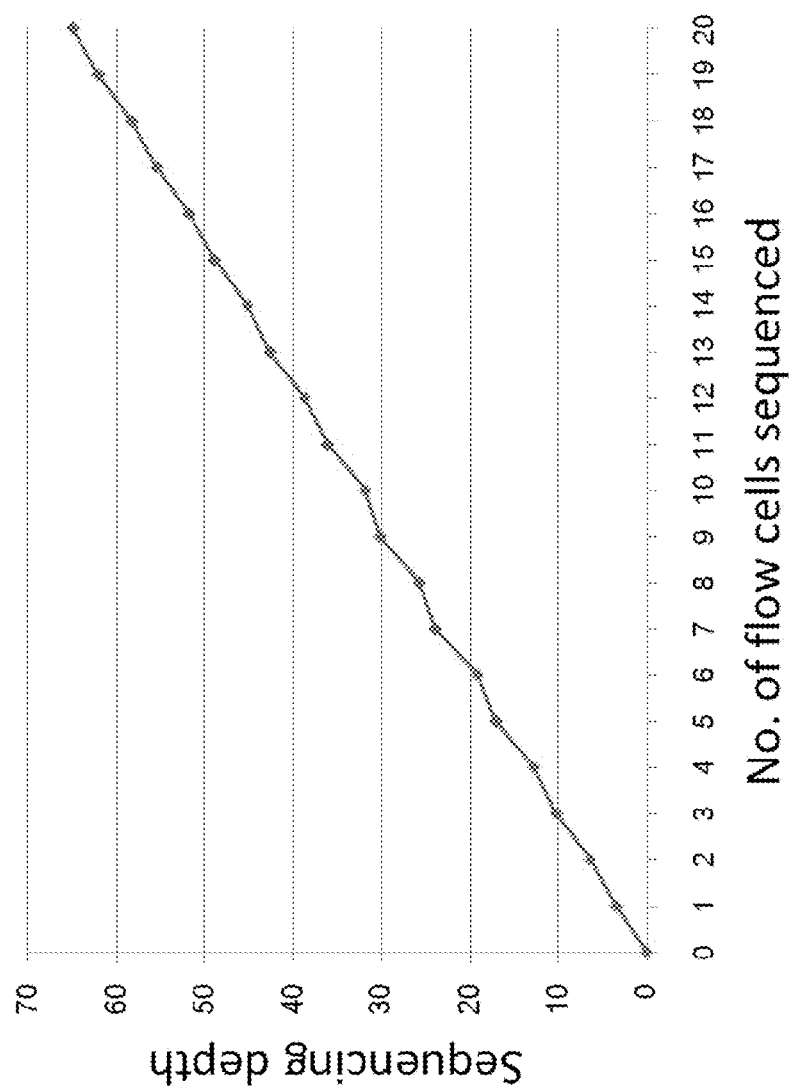
FIG. 40: Sequencing depth against no. of flow cells sequenced

DETERMINATION OF THE DEPTH COVERAGE OF THE FETAL GENOME

CROSS-REFERENCES TO RELATED APPLICATIONS

The present application is a divisional of U.S. application Ser. No. 12/940,993, entitled "Fetal Genomic Analysis From a Maternal Biological Sample," filed Nov. 5, 2010 which claims priority from and is a non-provisional application of U.S. Provisional Application No. 61/258,567, entitled "Fetal Genomic Analysis," filed Nov. 5, 2009; U.S. Provisional Application No. 61/259,075, entitled "Fetal Genomic Analysis from a Maternal Biological Sample," filed Nov. 6, 2009; and U.S. Provisional Application No. 61/381,854, entitled "Fetal Genomic Analysis from a Maternal Biological Sample," filed Sep. 10, 2010, the entire contents of which are herein incorporated by reference for all purposes.

The present application is also related to U.S. application Ser. No. 12/178,181, entitled "Diagnosing Fetal Chromosomal Aneuploidy Using Massively Parallel Genomic Sequencing," filed Jul. 23, 2008; U.S. application Ser. No. 12/614,350, entitled "Diagnosing Fetal Chromosomal Aneuploidy Using Genomic Sequencing With Enrichment," filed Nov. 6, 2009, and U.S. application Ser. No. 12/940,992, entitled "Size-Based Genomic Analysis," filed Nov. 5, 2010, the entire contents of which are herein incorporated by reference for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file -67-3.TXT, created on Jul. 26, 2013, 12,288 bytes, machine format IBM-PC, MS-Windows operating system, is hereby incorporated by reference in its entirety for all purposes.

BACKGROUND

The present invention relates generally to analyzing a fetal genome based on a maternal sample, and more particularly to determining all or parts of the fetal genome based on an analysis of genetic fragments in the maternal sample.

The discovery of cell-free fetal nucleic acids in maternal plasma in 1997 has opened up new possibilities for noninvasive prenatal diagnosis (Lo Y M D et al Lancet 1997; 350: 485-487; and U.S. Pat. No. 6,258,540). This technology has been rapidly translated to clinical applications, with the detection of fetal-derived, paternally-inherited genes or sequences, e.g. for fetal sex determination, fetal RhD status determination, and determination of whether the fetus has inherited a paternally-inherited mutation (Amicucci P et al Clin Chem 2000; 46: 301-302; Saito H et al Lancet 2000; 356: 1170; and Chiu R W K et al Lancet 2002; 360: 998-1000). Recent progress in the field has enabled the prenatal diagnosis of fetal chromosomal aneuploidies, such as trisomy 21, from maternal plasma nucleic acid analysis (Lo Y M D et al Nat Med 2007; 13: 218-223; Tong Y K et al Clin Chem 2006; 52: 2194-2202; US Patent publication 2006/0252071; Lo Y M D et al Proc Natl Acad Sci USA 2007; 104: 13116-13121; Chiu R W K et al Proc Natl Acad Sci USA 2008; 105: 20458-20463; Fan H C et al Proc Natl Acad Sci 2008; 105: 16266-16271; US Patent publication 2007/0202525; and US Patent publication 2009/0029377).

Another area of significant recent progress is the use of single molecule counting methods, such as digital PCR, for the noninvasive prenatal diagnosis of single gene diseases in which the mother and father both carry the same mutation. This has been achieved by relative mutation dosage (RMD) analysis in maternal plasma (US Patent application 2009/0087847; Lun F M F et al Proc Natl Acad Sci USA 2008; 105: 19920-19925; and Chiu R W K et al. Trends Genet 2009; 25: 324-331).

However, such methods use prior knowledge of possible mutations to analyze specific parts of a genome, and thus may not identify latent or uncommon mutations or genetic diseases. Therefore, it is desirable to provide new methods, systems, and apparatus that can identify all or parts of a fetal genome using non-invasive techniques.

BRIEF SUMMARY

Certain embodiments of the present invention can provide methods, systems, and apparatuses for determining at least a portion of the genome of an unborn fetus of a pregnant female. A genetic map of the whole genome or for selected genomic region(s) can be constructed of the fetus prenatally using a sample containing fetal and maternal genetic material (e.g. from a blood sample of the pregnant mother). The genetic map can be of sequences that a fetus has inherited from both of its father and mother, or just those of one of the parents. Based on one or several of such genetic maps, the risk that the fetus would be suffering from a genetic disease or predisposition to a genetic or other diseases or a genetic trait can be determined. Other application of embodiments are also described herein.

In one embodiment, DNA fragments from a maternal sample (containing maternal and fetal DNA) can be analyzed to identify alleles at certain specified loci (landmarks). The amount of DNA fragments of the respective alleles at these loci can then be analyzed together to determine the relative amounts of the haplotypes for these loci and thereby determine which haplotypes have been inherited by the fetus from the maternal and/or paternal genomes. By identifying the fetal haplotypes, the fetal genotype at an individual locus within the corresponding genomic region including the specified loci can be determined. In various embodiments, loci where the parents are a specific combination of homozygous and heterozygous can be analyzed in a manner to determine regions of the fetal genome. In one implementation, reference haplotypes that are representative of haplotypes common in the population are used along with the analysis of the DNA fragments of the maternal sample to determine the maternal and paternal genomes. Other embodiments are also provided, such as determining mutations, determining a fractional fetal concentration in a maternal sample, and determining a proportion of coverage of a sequencing of the maternal sample.

Other embodiments of the invention are directed to systems, apparatus, and computer readable media associated with methods described herein. In one embodiment, the computer readable medium contains instructions for receiving data and analyzing data, but not instructions for directing a machine to create the data (e.g. sequencing nucleic acid molecules). In another embodiment, the computer readable medium does contain instructions for directing a machine to create the data. In one embodiment, a computer program product comprises a computer readable medium storing a plurality of instructions for controlling a processor to perform an operation for methods described herein. Embodiments are also directed to computer systems configured to perform the steps of any of the methods described herein, potentially with different components performing a respective step or a respective group of steps.

Reference to the remaining portions of the specification, including the drawings and claims, will realize other features and advantages of embodiments of the present invention. Further features and advantages, as well as the structure and operation of various embodiments of the present invention, are described in detail below with respect to the accompanying drawings. In the drawings, like reference numbers can indicate identical or functionally similar elements.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3 shows the two types of SNPs in the parental haplotypes of FIG. 2 according to embodiments of the present invention.

FIGS. 4A and 4B shows an analysis for determining the fetal haplotypes for the two types of SNPs according to embodiments of the present invention.

FIGS. 5A and 5B shows the analysis of comparing relative amounts (e.g. counts) of fragments for each locus and whether a result of the comparison is to classify a particular haplotype as being inherited or not according to embodiments of the present invention.

FIG. 6 illustrates the effect of changing the likelihood ratio for SPRT classification according to embodiments of the present invention.

FIG. 25A shows the absolute number and the percentages of SNPs showing different genotype combinations for the father, mother and fetus (CVS) according to embodiments of the present invention.

FIG. 25B shows a table listing the alignment statistics of the first 20 flow cells.

FIG. 26 is a table showing the fractional concentrations of fetal DNA calculated for SNPs via two methods according to embodiments of the present invention.

FIG. 27A shows a plot illustrating the observed percentage of SNPs in this subset in which a fetal allele could be seen from the sequencing data for the first 20 flow cells analyzed, and FIG. 27B shows a plot of the coverage vs. the number of reads according to embodiments of the present invention.

FIGS. 28A and 28B shows plots of the correlation between the coverage of paternally-inherited alleles and the number of mappable sequence reads and the number of flow cells sequences, respectively, according to embodiments of the present invention.

FIG. 29A shows the correlation between the false-positive rate and the number of flow cells sequenced, and FIG. 29B shows the correlation between false-positive rate and the number of flow cells sequenced according to embodiments of the present invention.

FIG. 30 shows the coverage of the fetal-specific SNPs for different number of flow cells analyzed according to embodiments of the present invention.

FIG. 31 shows the accuracy of Type A analysis when data from 10 flow cells were used according to embodiments of the present invention.

FIG. 32 shows the accuracy of Type B analysis when data from 10 flow cells were used according to embodiments of the present invention.

FIG. 33 shows the accuracy of Type A analysis when the data from 20 flow cells were used according to embodiments of the present invention.

FIG. 34 shows the accuracy of Type B analysis when the data from 20 flow cells were used according to embodiments of the present invention.

FIGS. 35A and 35B show reads with a mutations and with a wildtype sequence at codons 41/42 according to embodiments of the present invention. Reads with CD41/42 paternally inherited mutation=SEQ ID NOS:5, 5 and 6-13, respectively. Reads with wildtype sequence in CD41/42=SEQ ID NOS:14, 14, 15, 16, 17, 17, 18, 19, 20, 20, 20, 21, 21, 22-28, 29, 29, 30, 30, 30, 31, 32, 32, 33, 34, 35, 35, 36, 36, 37, 38, 39, 39, 40-42, 43, 43, 44-46, 47, 47, 47, 48-51, 52 and 52, respectively.

FIG. 36 shows a table of a Type A RHDO analysis while those of the Type B RHDO analysis are shown in FIG. 37 according to embodiments of the present invention.

FIGS. 38A and 38B shows the SPRT classification results for case PW226 as an example.

FIG. 39 shows a table summarizing the RHDO analysis results for the five cases according to embodiments of the present invention.

FIG. 40 shows a plot of sequencing depth against the number of flow cells sequenced according to embodiments of the present invention.

DEFINITIONS

Figure 1:
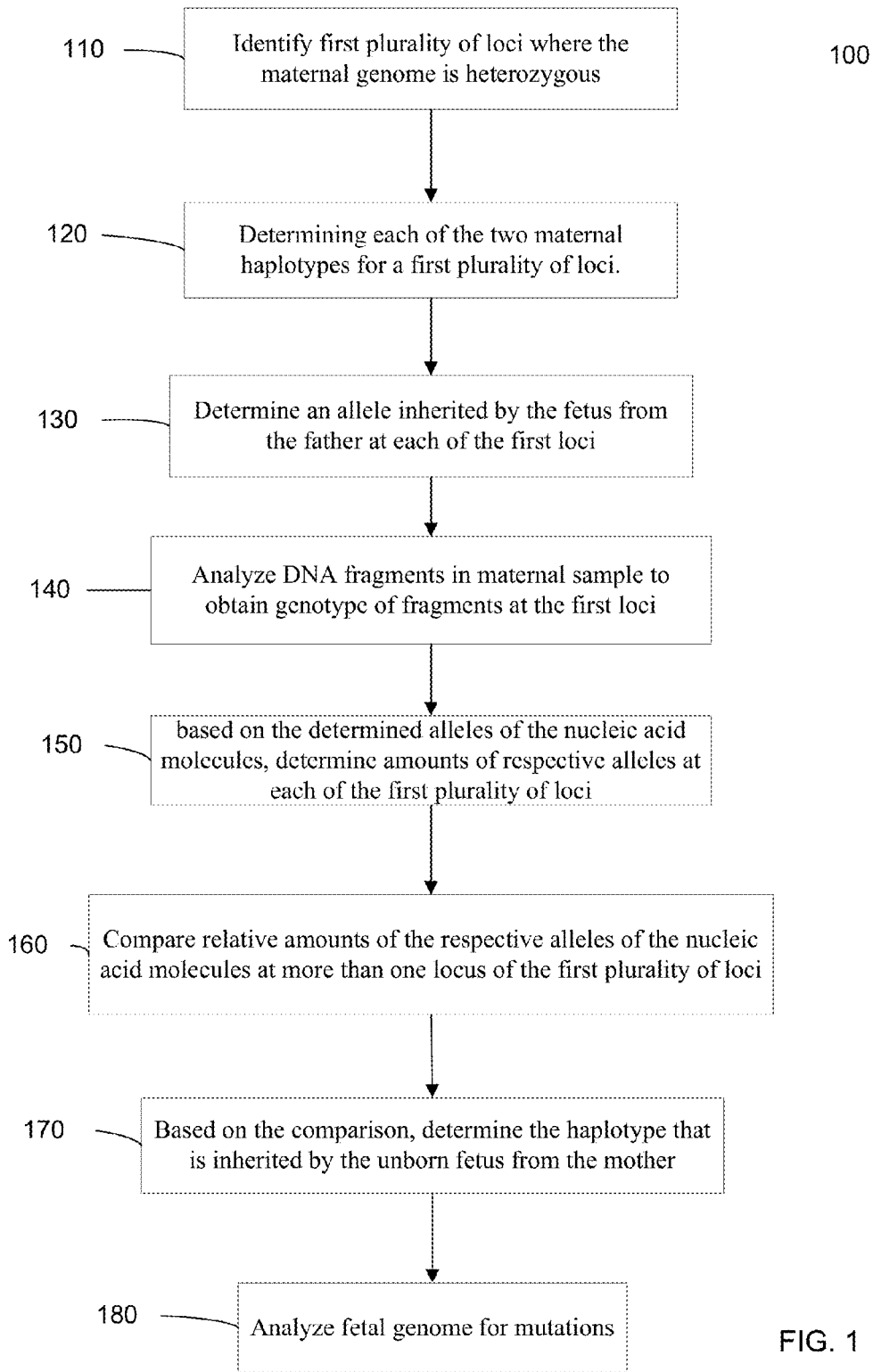
FIG. 1 is a flowchart of a method 100 of determining at least a portion of the genome of an unborn fetus of a pregnant female according to embodiments of the present invention.

The term "biological sample" as used herein refers to any sample that is taken from a subject (e.g., a human, such as a pregnant woman) and contains one or more nucleic acid molecule(s) of interest.

The term "nucleic acid" or "polynucleotide" refers to a deoxyribonucleic acid (DNA) or ribonucleic acid (RNA) and a polymer thereof in either single- or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid is used interchangeably with gene, cDNA, mRNA, small noncoding RNA, micro RNA (miRNA), Piwi-interacting RNA, and short hairpin RNA (shRNA) encoded by a gene or locus.

The term "gene" means the segment of DNA involved in producing a polypeptide chain or transcribed RNA product. It may include regions preceding and following the coding region (leader and trailer) as well as intervening sequences (introns) between individual coding segments (exons).

The term "clinically relevant nucleic acid sequence" (also referred to as a target sequence or chromosome) as used herein can refer to a polynucleotide sequence corresponding to a segment of a larger genomic sequence whose potential imbalance is being tested or to the larger genomic sequence itself. One example is the sequence of chromosome 21. Other examples include chromosome 18, 13, X and Y. Yet other examples include mutated genetic sequences or genetic polymorphisms or copy number variations that a fetus may inherit from one or both of its parents, or as a de novo mutation in the fetus. In some embodiments, multiple clinically relevant nucleic acid sequences, or equivalently multiple makers of the clinically relevant nucleic acid sequence, can be used to provide data for detecting the imbalance. For instance, data from five non-consecutive sequences on chromosome 21 can be used in an additive fashion for the determination of possible chromosomal 21 imbalance, effectively reducing the needed sample volume to ⅕.

The term "based on" as used herein means "based at least in part on" and refers to one value (or result) being used in the determination of another value, such as occurs in the relationship of an input of a method and the output of that method. The term "derive" as used herein also refers to the relationship of an input of a method and the output of that method, such as occurs when the derivation is the calculation of a formula.

The term "parameter" as used herein means a numerical value that characterizes a quantitative data set and/or a numerical relationship between quantitative data sets. For example, a ratio (or function of a ratio) between a first amount of a first nucleic acid sequence and a second amount of a second nucleic acid sequence is a parameter.

As used herein, the term "locus" or its plural form "loci" is a location or address of any length of nucleotides (or base pairs) which has a variation across genomes.

The term "sequence imbalance" as used herein means any significant deviation as defined by at least one cutoff value in a quantity of the clinically relevant nucleic acid sequence from a reference quantity. A sequence imbalance can include chromosome dosage imbalance, allelic imbalance, mutation dosage imbalance, haplotype dosage imbalance, and other similar imbalances. As an example, an allelic or mutation dosage imbalance can occur when a fetus has a different genotype from the mother, thereby creating an imbalance at a particular locus in the sample.

The term "chromosomal aneuploidy" as used herein means a variation in the quantitative amount of a chromosome from that of a diploid genome. The variation may be a gain or a loss. It may involve the whole of one chromosome or a region of a chromosome.

The term "haplotype" as used herein refers to a combination of alleles at multiple loci that are transmitted together on the same chromosome or chromosomal region. A haplotype may refer to as few as one pair of loci or to a chromosomal region, or to an entire chromosome. The term "alleles" refers to alternative DNA sequences at the same physical genomic locus, which may or may not result in different phenotypic traits. In any particular diploid organism, with two copies of each chromosome (except the sex chromosomes in a male human subject), the genotype for each gene comprises the pair of alleles present at that locus, which are the same in homozygotes and different in heterozygotes. A population or species of organisms typically includes multiple alleles at each locus among various individuals. A genomic locus where more than one allele is found in the population is termed a polymorphic site. Allelic variation at a locus is measurable as the number of alleles (i.e., the degree of polymorphism) present, or the proportion of heterozygotes (i.e., the heterozygosity rate) in the population. As used herein, the term "polymorphism" refers to any inter-individual variation in the human genome, regardless of its frequency. Examples of such variations include, but are not limited to, single nucleotide polymorphism, simple tandem repeat polymorphisms, insertion-deletion polymorphisms, mutations (which may be disease causing) and copy number variations.

DETAILED DESCRIPTION

A construction of a partial genetic map or complete genomic sequence of an unborn fetus can be provided based on the haplotypes of polymorphic sequences of its parents. The term "haplotype" as used herein refers to a combination of alleles at multiple loci that are transmitted together on the same chromosome or chromosomal region. For example, embodiments can analyze DNA fragments from a maternal sample (containing maternal and fetal DNA) to identify alleles at certain specified loci (landmarks). The amounts of DNA fragments of the respective alleles at these loci can then be analyzed together to determine the relative amounts of the haplotypes for these loci and thereby determine which haplotypes have been inherited by the fetus from the maternal and/or paternal genomes. By identifying the fetal haplotypes, the fetal genotype at an individual locus within the corresponding genomic region including the specified loci can be determined. In various embodiments, loci where the parents are a specific combination of homozygous and heterozygous can be analyzed in a manner to determine regions of the fetal genome. In one implementation, reference haplotypes that are representative of haplotypes common in the population are used along with the analysis of the DNA fragments of the maternal sample to determine the maternal and paternal genomes.

An example of an application of an embodiment for determining at least part of a fetal genome could be for paternity testing by comparing the deduced fetal genotype or haplotype with the genotype or haplotype of the alleged father. Another example is to detect one or more de novo mutations that the fetus has acquired, or detect meiotic recombination events that have occurred during the production of gametes from its parents. These are the gametes that have fertilized, and the resulting zygote has developed into the fetus.

In addition, some embodiments can also allow the genomic sequence of the unborn fetus to be determined at any desired resolution. For example, in certain applications, embodiments can allow the complete or close to complete genomic sequence of the fetus to be determined. In one embodiment, the resolution of the fetal genomic sequence that can be determined is dependent on the resolution of the knowledge of the genomes of the father and mother, in conjunction with the sequencing information from the maternal biological sample containing fetal nucleic acids. In the event that the complete or close to complete genomic sequences of the father and mother are known, the complete or close to complete genomic sequence of the unborn fetus could be deduced.

In other embodiments, only the genomic sequences of selected regions within the genome are elucidated, e.g., for the prenatal diagnosis of selected genetic, epigenetic (such as imprinting disorders), or chromosomal disorders. Examples of genetic disorders to which an embodiment can be applied include the hemoglobinopathies (such as beta-thalassemia, alpha-thalassemia, sickle cell anemia, hemoglobin E disease), cystic fibrosis, and sex-linked disorders (such as hemophilia and Duchenne muscular dystrophy). Further examples of mutations that can be detected using an embodiment can be found from the Online Mendelian Inheritance in Man (www.ncbi.nlm.nih.gov/omim/getmorbid.cgi).

Some embodiments can also be used to determine a fractional concentration of fetal DNA, which may be done without any prior knowledge of the specific genomes of the parents. A similar analysis can also be used to determine a depth of coverage needed for an accurate determination of the fetal genome. Thus, this coverage determination can be used to estimate how much data needs to be analyzed to obtain accurate results.

I. INTRODUCTION

When a maternal sample (e.g. plasma or serum) is used as the material for elucidating the fetal haplotype, there can be two main challenges. A first challenge is that maternal plasma or serum consists of a mixture of fetal and maternal DNA, with fetal DNA being the minor population. It has been determined that fetal DNA represents a mean/median concentration of some 5% to 10% of the total DNA in maternal plasma in the first two trimesters of pregnancy (Lo Y M D et al Am J Hum Genet 1998; 62: 768-775; Lun F M F et al Clin Chem 2008; 54: 1664-1672). As DNA is released by maternal blood cells during the blood clotting process, the fractional concentration of fetal DNA in maternal serum can be even lower than that in maternal plasma. Thus, in some embodiments, maternal plasma is preferred over maternal serum.

A second challenge is that fetal DNA and maternal DNA in maternal plasma consist of short fragments (Chan K C A et al Clin Chem 2004; 50: 88-92). Indeed the fetal-derived DNA is generally shorter than the maternal-derived DNA in maternal plasma. Most of the fetal DNA in maternal plasma is less than 200 bp in length. Using such short plasma DNA fragments alone, it can be challenging to construct the haplotype of genetic polymorphisms over long genomic distances. The above-mentioned challenges for maternal plasma and serum also apply for the detection of fetal DNA in maternal urine (Botezatu I et al Clin Chem 2000; 46: 1078-1084). Fetal DNA only represents a minor fraction of the DNA in the urine of a pregnant woman, and fetal DNA in maternal urine also consists of short DNA fragments.

A. Sequencing and Analyzing of Maternal Sample

An approach that some embodiments have taken to address the first challenge is to use a method that allows the quantitative genotyping of nucleic acids obtained from the maternal biological sample with high precision. In one embodiment of this approach, the precision is achieved by analysis of a large number (for example, millions or billions) of nucleic acid molecules. Furthermore, the precision can be enhanced by the analysis of single nucleic acid molecules or the clonal amplification of single nucleic acid molecules. One embodiment uses massively parallel DNA sequencing, such as, but not limited to that performed by the Illumina Genome Analyzer platform (Bentley D R et al. Nature 2008; 456: 53-59), the Roche 454 platform (Margulies M et al. Nature 2005; 437: 376-380), the ABI SOLiD platform (McKernan K J et al. Genome Res 2009; 19: 1527-1541), the Helicos single molecule sequencing platform (Harris T D et al. Science 2008; 320: 106-109), real-time sequencing using single polymerase molecules (Science 2009; 323: 133-138) and nanopore sequencing (Clarke J et al. Nat Nanotechnol. 2009; 4: 265-70). In one embodiment, massively parallel sequencing is performed on a random subset of nucleic acid molecules in the biological sample.

In some embodiments, it can be beneficial to obtain as long a sequence read from each molecule as is possible. One limitation of the length of the sequencing reads that can be achieved is the nature of the nucleic acid molecules in the maternal biological sample. For example, it is known that most DNA molecules in maternal plasma consist of short fragments (Chan K C A et al Clin Chem 2004; 50: 88-92). Furthermore, the read length has to be balanced against the fidelity of the sequencing system at long read lengths. For some of the above-mentioned systems, it might be preferable to obtain sequences from both ends of the molecule, the so-called paired-end sequencing. As an illustration, one approach is to perform 50 bp of sequencing from each end of a DNA molecule, thus resulting in a total of 100 bp of sequence per molecule. In another embodiment, 75 bp of sequencing from each end of a DNA molecule, thus resulting in a total of 150 bp of sequence per molecule, can be done.

After the sequencing is performed, the sequences are then aligned back to a reference human genome. As embodiments elucidate the genomic variations inherited by an unborn fetus from its parents, the alignment algorithm can be able to cope with sequence variations. One example of such a software package is the Efficient Large-Scale Alignment of Nucleotide Databases (ELAND) software produced by Illumina Another example of such a software package is the SOAP (short oligonucleotide alignment program) and SOAP2 software (Li R et al. Bioinformatics 2008; 24:713-714; Li R et al. Bioinformatics 2009; 25:1966-1967).

The amount of DNA sequencing that may need to be performed can depend on the resolution at which the fetal genetic map or fetal genomic sequence may need to be constructed. In general, the more molecules that are sequenced the higher the resolution. Another determinant of the resolution of the fetal genetic map or fetal genomic sequence at a given level, or depth, of DNA sequencing is the fractional concentration of fetal DNA in the maternal biological sample. In general, the higher the fractional fetal DNA concentration, the higher is the resolution of the fetal genetic map or fetal genomic sequence that can be elucidated at a given level of DNA sequencing. As the fractional concentration of fetal DNA in maternal plasma is higher than that in maternal serum, maternal plasma is a more preferred maternal biological sample type than maternal serum for some embodiments.

The throughput of the above-mentioned sequencing-based methods can be increased with the use of indexing or barcoding. Thus, a sample or patient-specific index or barcode can be added to nucleic acid fragments in a particular nucleic acid sequencing library. Then, a number of such libraries, each with a sample or patient-specific index or barcode, are mixed together and sequenced together. Following the sequencing reactions, the sequencing data can be harvested from each sample or patient based on the barcode or index. This strategy can increase the throughput and thus the cost-effectiveness of embodiments of the current invention.

In one embodiment, the nucleic acid molecules in the biological sample can be selected or fractionated prior to quantitative genotyping (e.g. sequencing). In one variant, the nucleic acid molecules are treated with a device (e.g. a microarray) which can preferentially bind nucleic acid molecules from selected loci in the genome (e.g. the region on chromosome 7 containing the CFTR gene). Then the sequencing can be performed preferentially on nucleic acid molecules captured by the device. This scheme will allow one to target the sequencing towards the genomic region of interest. In one embodiment of this scheme a Nimblegen sequence capture system (www.nimblegen.com/products/seqcap/index.html) or an Agilent SureSelect Target Enrichment System (www.opengenomics.com/SureSelect_Target_Enrichment_System), or similar platforms, can be used. In some embodiments, the nucleic acid molecules from the selected regions of the genome are subjected to random sequencing.

In another embodiment, the genomic region of interest in the biological sample can be first amplified by one set or multiple set of amplification primers. Then, the quantitative genotyping, for example, sequencing, can be performed on the amplified products. In one implementation of this scheme, the RainDance (www.raindancetech.com/technology/per-genomics-research.asp) system can be used. In some embodiments, the amplified nucleic acid molecules are subjected to random sequencing.

A size fractionation step can also be performed on the nucleic acid molecules in the biological sample. As fetal DNA is known to be shorter than maternal DNA in maternal plasma (Li et al Clin Chem 2004; 50: 1002-1011; US Patent Application 20050164241; US Patent application 20070202525), the fraction of smaller molecular size can be harvested and then used for the quantitative genotyping, for example, sequencing. Such a fraction would contain a higher fractional concentration of fetal DNA than in the original biological sample. Thus, the sequencing of a fraction enriched in fetal DNA can allow one to construct the fetal genetic map or deduce the fetal genomic sequence with a higher resolution at a particular level of analysis (e.g. depth of sequencing), than if a non-enriched sample has been used. This can therefore make the technology more cost-effective. As examples of methods for size fractionation, one could use (i) gel electrophoresis followed by the extraction of nucleic acid molecules from specific gel fractions; (ii) nucleic acid binding matrix with differential affinity for nucleic acid molecules of different sizes; or (iii) filtration systems with differential retention for nucleic acid molecules of different sizes.

In yet another embodiment, one could preferentially analyze nucleic acid molecules of a specific size or size range following the nucleic acid sequencing. For example, one could perform paired-end sequencing in which both ends of a DNA molecule are sequenced. Then, the genomic coordinates of both of these ends could be mapped back to a reference human genome. Then one could deduce the size of the molecule by subtracting the genomic coordinates of both ends. One way to perform such paired-end sequencing is to use the paired-end sequencing protocol of the Illumina Genome Analyzer. Another method to deduce the size of a DNA molecule is to sequence the entire DNA molecule. This is most readily done by sequencing platforms with relatively long read lengths, such as the Roche 454 platform (Marguelis et al Nature 2005; 437:376-380) and the Pacific Biosciences single molecule, real-time (SMRT™) technology (Eid et al Science 2009; 323: 133-138). Following the deduction of the size of the nucleic acid molecules, one could choose to focus the subsequent analysis on molecules of less than a particular size cutoff, thereby enriching in the fractional concentration of fetal DNA. Analysis of this subset of molecules can allow the fetal genetic map or fetal genomic sequences to be deduced with fewer analyzed molecules after the size selection than be if this procedure has not been done. In one embodiment, a size cutoff of 300 bp is used. In yet other embodiments, a size cutoff of 250 bp, 200 bp, 180 bp, 150 bp, 125 bp, 100 bp, or 75 bp could be used.

B. Using Parental Genomes as Scaffolds

To address the second challenge, some embodiments can use haplotypes of the chromosomes of the mother as a 'scaffold'. The haplotypes of the chromosomes of the father can also be used as another 'scaffold'. This scaffold can be compared against genetic information of the fetus obtained from the maternal sample containing fetal DNA. This fetal genetic information can be used to determine how the scaffold of the mother and/or father have been erected in the fetal genome, thereby using the component parts of the scaffold to determine the resulting fetal genome.

The parental haplotypes can be constructed from genomic DNA from the father and mother, and from other members of the family, e.g. a sibling of the fetus in the current pregnancy. It is possible that the availability of the parental haplotypes can become increasingly commonplace, in view of the reduction in the costs of genomic sequencing. In one scenario, if one or both parents already have their genomes sequenced and their haplotypes on one or more chromosomal regions have been determined, then this information can be used as the above-mentioned scaffold.

Any genotyping platform known to those of skill in the art that can interrogate sequence variations in the genome can be used, including DNA sequencing, microarrays, hybridization probes, fluorescence-based techniques, optical techniques, molecular barcodes and single molecule imaging (Geiss G K et al. Nat Biotechnol 2008; 26: 317-325), single molecule analysis, PCR, digital PCR, mass spectrometry (such as the Sequenom MassARRAY platform), etc. As a more extreme example, the DNA sequence of the father and mother can be determined by whole genome DNA sequencing using a massively parallel sequencing method (e.g. Bentley D R et al. Nature 2008; 456: 53-59; McKernan K J et al. Genome Res 2009; 19: 1527-1541). An example of sequence variations that may be of interest are single nucleotide polymorphisms (SNPs). A particularly preferred method for determining the parental genotypes is by microarray analysis of SNPs on a genomewide scale, or at selected genomic regions, e.g. those containing genes whose mutations can cause genetic diseases (such as genes in the beta-globin cluster, or the cystic fibrosis transmembrane conductance regulator (CFTR) gene). Apart from sequence variations, copy number variations can also be used. Sequence variations and copy number variations are both referred to as polymorphic genetic features (PMF).

In one aspect, the maternal genotypes on the chromosomes or chromosomal regions of interest can be constructed into haplotypes. One way in which this can be performed is by the analysis of other family members related to the mother, e.g. a son or daughter of the mother, a parent, a sibling, etc. Another way in which the haplotypes can be constructed is through other methods well known to those skilled in the art mentioned above.

The genotype information can then be extended into haplotype information of the parents by comparison with the genotype information from other family members, for example, a sibling of the fetus of the current pregnancy, or from the genotypes of the grandparents, etc. Haplotypes of the parents can also be constructed by other methods well known to those skilled in the art. Examples of such methods include methods based on single molecule analysis such as digital PCR (Ding C and Cantor C R. Proc Natl Acad Sci USA 2003; 100: 7449-7453; Ruano G et al. Proc Natl Acad Sci USA 1990; 87: 6296-6300), sperm haplotyping (Lien S et al. Curr Protoc Hum Genet 2002; Chapter 1:Unit 1.6) and imaging techniques (Xiao M et al. Hum Mutat 2007; 28: 913-921). Other methods include those based on allele-specific PCR (Michalatos-Beloin S et al. Nucleic Acids Res 1996; 24: 4841-4843; Lo Y M D et al. Nucleic Acids Res 1991; Nucleic Acids Res 19: 3561-3567), cloning and restriction enzyme digestion (Smirnova A S et al. Immunogenetics 2007; 59: 93-8), etc. Yet other methods are based on the distribution and linkage disequilibirum structure of haplotype blocks in the population which allow the maternal haplotype to be inferred from statistical assessments (Clark A G. Mol Biol Evol 1990; 7:111-22; 10:13-9; Salem R M et al. Hum Genomics 2005; 2:39-66).

C. Using Genomic Information of Maternal Sample to Assemble the Scaffold

In one embodiment, to work out which of the maternal chromosomes have been passed onto the fetus, a relative haplotype dosage (RHDO) method is used. A general principle of this approach is as follows for an example of where the mother is heterozygous for each of the genetic polymorphisms. Thus, there are two haplotypes, and the relative dosage of these haplotypes would be 1:1. However, in the maternal sample, the presence of a small proportion of fetal DNA might alter the relative haplotype dosage. This is because the fetus would have inherited half of its haplotype complement from the mother and the other half from the father. Furthermore, for each chromosome, the fetus might have inherited a 'patchwork' of haplotypes which have originated from one or the other homologous chromosomes from each parent, depending on the occurrence of meiotic recombination. All of these factors might deviate the relative haplotype dosage from the 1:1 ratio in the maternal constitutional DNA. Thus, for a given chromosome or chromosomal region, the constituent alleles of these haplotypes can be sought from analytic data (e.g. sequencing data) generated from the maternal sample.

Then, a statistical procedure can be performed to determine the relative haplotype dosage, or if one of these haplotypes is overrepresented over the other haplotype. The classification threshold for this statistical procedure can be adjusted depending on the fractional fetal DNA concentration. In general, a higher fractional fetal DNA concentration can allow the threshold to be reached with fewer molecules. The classification threshold can also be adjusted depending on the number of successfully classified fragments that one wishes to achieve across the genome or the genomic regions of interest. In one embodiment, the sequential probability ratio test (SPRT) can be used.

In one embodiment, a relative mutation dosage (RMD), as described in US Patent application 2009/0087847) can be used to determine a relative amount of an allele at particular polymorphisms of the mother. These relative amounts can be used in determining a haplotype of the fetus (e.g. when the polymorphisms are at consecutive or linked loci). In one implementation of this targeted approach is the use of the polymerase chain reaction (PCR) to amplify specific sequences from selected parts of the genome for RMD analysis. To extend this RMD approach to determine fetal inheritance over a large genomic region or the whole genome, a large volume of maternal sample is needed.

In an embodiment using random sequencing, the genomic regions of interest are not specifically targeted. Thus, the number of sequences obtained in the genomic regions of interest may not be as numerous as in a targeted approach (unless very deep sequencing is performed). However, counts can be pooled the counts across a number of linked polymorphisms, to achieve the necessary statistical power for diagnostic purposes. A practical implication of using this sequencing embodiment is that it can save costs by avoiding the need for excessively deep sequencing. It also requires an input of a lesser amount of maternal sample than digital PCR based approaches.

Furthermore, it can be desirable to perform such RHDO analysis in blocks. In other words, each chromosome can be analyzed in one, or preferably more than one block. In one aspect, the latter can allow meiotic recombination to be observed. For example, a haplotype of a segment of a particular chromosome of the fetus can appear to have come from one of the maternal homologous chromosomes, while another segment of the same fetal chromosome appears to possess the haplotype from the other maternal homologous chromosome. An SPRT analysis can allow this segmentation to be performed.

For example, SPRT analysis can be performed on neighboring SNPs demonstrating the required parental genotype configuration (i.e. the father being homozygous and the mother being heterozygous) starting from one end of a chromosome. This will continue until the SPRT analysis has indicated that one of the maternal haplotype is predominant in the maternal plasma analytic data (e.g. sequencing data). Then, the SPRT analysis can be 'reset' and start afresh from the next neighboring SNP demonstrating the required parental genotype configuration. This can again continue until the SPRT analysis has once again indicated that one of the maternal haplotype is predominant in the maternal plasma analytic data (e.g. sequencing data). This process can continue until the last selected SNP on the said chromosome. Then, these various SPRT-determined haplotype segments on the chromosome can be compared with the haplotypes of the two homologous chromosomes in the mother's genome. A meiotic recombination is seen when the haplotype segments in the fetus appear to have switched from one maternal homologous chromosome to another one. This system can also work even if there is more than one meiotic recombination per chromosome.

As is described later, RHDO analysis can also be carried out for genomic regions in which the father and mother are both heterozygous for the constituent genetic polymorphisms. This scenario is particularly useful for situation when the father and mother share a mutant copy of the disease gene from the same ancestral origin, such as when they are consanguineous, or when the predominant mutation for the disease is due to a large founder effect (i.e. most individuals with the mutation has inherited the same haplotype from a common ancestral founder of the population). Thus, the haplotypes of the father and mother in this region can be used to deduce the fetal haplotype.

II. CONSTRUCTING FETAL GENOME FROM MATERNAL GENOME

Constructing a fetal genetic map or elucidating the fetal genomic sequence with explicit knowledge of the parental genomes is now described.

A. Method

FIG. 1 is a flowchart of a method 100 of determining at least a portion of the genome of an unborn fetus of a pregnant female. The fetus has a father and a mother being the pregnant female. The father has a paternal genome with two haplotypes and the mother has a maternal genome with two haplotypes. Method 100 analyzes nucleic acid molecules (fragments) from a biological sample obtained from the pregnant female to determine the genome of the fetus. Method 100 is described primarily for the example of when the father is homozygous and the mother is heterozygous at a plurality of loci, while other examples describe other embodiments Method 100 and any of the methods described herein may be totally or partially performed with a computer system including a processor, which can be configured to perform the steps. Thus, embodiments are directed to computer systems configured to perform the steps of any of the methods described herein, potentially with different components performing a respective step or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

In step 110, a first plurality of loci are identified at which the maternal genome is heterozygous. In one embodiment, this determination can be performed at part of a genotyping of the father and mother at the genomewide level or at selected genomic loci of interest. In other embodiments, the determination of the first plurality of loci can be made during an analysis of the maternal sample, which is described in later sections.

In step 120, each of the two maternal haplotypes covering the first plurality of loci are determined. As mentioned above, the maternal genome could be obtained from direct sequencing. In other embodiments, genotyping can be done at a plurality of loci and then use a mapped genome of someone that is expected to have a similar genome, e.g. from a family member or from a reference genome that is common in a same or similar population. In one embodiment, step 120 can be performed first for all or parts of the maternal genome and then the maternal genome can be investigated to find loci where the mother is heterozygous.

In one aspect, it is not essential to construct the haplotypes of the chromosomes of the father. However, if the paternal haplotypes could be constructed then additional information could be obtained from the sequencing results. One such additional information includes the fact that relative haplotype dosage analysis can be performed for regions for which both parents are heterozygous. Another additional piece of information which can be obtained if the paternal haplotype is available is information concerning meiotic recombination involving one or more paternal chromosomes, and to determine if disease alleles linked to such polymorphisms have been passed onto to the fetus.

In step 130, an allele inherited by the fetus from the father at each of the first plurality of loci is determined. Some embodiments use genomic loci which are homozygous for the father, but heterozygous for the mother (as mentioned in step 110). Thus, if the father is homozygous at the loci, then the allele that is inherited from the father is known. The genotyping of the father to determine loci at which the father is homozygous can be determined in any of the ways described herein. In one embodiment, the determination of the first plurality of loci can be determined based on the genotyping of the father and mother in order to find loci at which the father is homozygous and at which the mother is heterozygous.

In another embodiment, a second plurality of loci of the paternal genome that are heterozygous can be used to determine the paternal haplotype inherited by the fetus at the first plurality of loci at which the father is homozygous. For example, if the maternal genome is homozygous at the second plurality of loci, alleles that are present in the paternal genome at respective ones of the second plurality of loci and absent in the maternal genome can be identified. The inherited paternal haplotype can then be identified as the haplotype with the identified alleles, and used to determine the allele inherited from the father at the first plurality of loci. These aspects of determining a paternal haplotype are discussed in more detail below.

In step 140, a plurality of nucleic acid molecules from a biological sample obtained from the pregnant female analyzed. The sample contains a mixture of maternal and fetal nucleic acids. The maternal biological sample can be taken and then received for analysis. In one embodiment, maternal plasma and serum is used. In other embodiments, maternal blood, maternal urine, maternal saliva, uterine lavage fluid, or fetal cells obtained from maternal blood can be used.

In one embodiment, analyzing a nucleic acid molecule includes identifying a location of the nucleic acid molecule in the human genome, and determining an allele of the nucleic acid molecule at the individual locus. Thus, one embodiment can perform quantitative genotyping using the determined alleles of the nucleic acid molecules from the same locus. Any method that will allow the determination of the genomic location and allele (information as to genotype) of nucleic acid molecules in the maternal biological sample can be used. Some of such methods are described in U.S. application Ser. Nos. 12/178,181 and 12/614,350, and application entitled "Size-Based Genomic Analysis."

In step 150, based on the determined alleles of the nucleic acid molecules, amounts of respective alleles at each of the first plurality of loci are determined. In one embodiment, the amounts can be the number of alleles of each type at a first locus. For example, six A and four T. In another embodiment, an amount can be a size distribution of the nucleic acid molecules having a particular allele. For example, a relative amount can also include a size distribution of the fragments with a particular genotype, which can convey a relative amount of fragments at certain lengths. Such relative amounts can also provide information as to which genotype is in the fetal genome, since fetal fragments tend to be smaller than the maternal fragments. Some examples of amounts and methods are described in U.S. application Ser. Nos. 12/178,181 and 12/614,350, and application entitled "Size-Based Genomic Analysis."

In one embodiment, the relative amounts of the alleles at a locus can provide information as to which genotype was inherited by the fetus (e.g. after a dataset has reached sufficient statistical power). For example, the relative amounts can be used to determine whether a sequence imbalance occurs relative to the mother's genotypes at a locus. The related patent applications cited above provide examples of embodiments for detecting a sequence imbalance at a particular locus or region.

In step 160, relative amounts of the respective alleles of the nucleic acid molecules at more than one locus of the first plurality of loci are compared. In some embodiments, amounts of each allele at each locus of the first plurality of loci comprising the haplotypes are aggregated before making a comparison. The aggregated amounts of the parental haplotypes can then compared to determine if a haplotype is over-represented, equally represented or under-represented. In other embodiments, the amounts for the alleles at a locus are compared, and comparisons at multiple loci are used. For example, a separation value (e.g. a difference or a ratio) can be aggregated, which can be used in a comparison with a cutoff value. Each of these embodiments can apply to any of the comparisons steps described herein.

In various embodiments, the relative amounts can be a count of a number of each fragment with a particular allele at a particular locus, a count of a number of fragments from any locus (or any loci in a region) on a particular haplotype, and a statistical value of the count (e.g., an average) at a particular locus or on a particular haplotype. Thus, in one embodiment, the comparison can be a determination of a separation value (e.g. a difference or a ratio) of one allele vs. another allele at each loci.

In step 170, based on the comparison, the haplotype that is inherited by the unborn fetus from the mother at the portion of the genome covered by the first plurality of loci can be determined. In one embodiment, to work out which of the maternal chromosomes have been passed onto the fetus, a relative haplotype dosage (RHDO) method is used, e.g., as mentioned above. As the mother is heterozygous for each of the first loci, the first loci correspond to two haplotypes for the genomic region of first loci. The relative dosage of these haplotypes would be 1:1 if the sample was just from the mother. Deviations or lack of deviations from this ratio can be used to determine the haplotype of the fetus that is inherited from the mother (and the father, which is addressed in more detail later). Thus, for a given chromosome or chromosomal region, the constituent alleles of these haplotypes can be sought from the analytic data (e.g. sequencing data) generated in step 130.

Since a plurality of loci are analyzed and compared to the haplotype of the mother, the sequences between the loci can be attributed to a particular haplotype. In one embodiment, if several loci match a particular haplotype, then the sequence segments between the loci can be assumed to be the same as that of the maternal haplotype. Because of the occurrence of meiotic recombination, the final haplotype inherited by the fetus can consist of a patchwork of 'haplotype segments' originating from one of these two homologous chromosomes. Embodiments can detect such recombination.

The resolution in which one could detect such recombination is dependent on the number and distribution of the genetic markers that one has determined in the father's and mother's constitutional DNA, and the threshold that one uses in the subsequent bioinformatic analysis (using for example the SPRT). For example, if the comparison suggests that the allele inherited from the mother at each of a first set of consecutive loci correspond to the first haplotype, then the first haplotype is determined to be inherited for the genomic location corresponding to the first set of loci. If a second set of consecutive loci suggest that the second haplotype is inherited, then the second haplotype is determined to be inherited for the genomic location corresponding to the second set of loci.

In one embodiment, as a plurality of loci are analyzed, the haplotype can be determined with greater accuracy. For example, the statistical data for one loci may not be determinative, but when combined with the statistical data of other loci, a determination of which haplotype is inherited can be made. In another embodiment, each loci can be analyzed independently to make a classification, and then the classifications can be analyzed to provide a determination of which haplotype is inherited for a given region.

In one embodiment, a statistical procedure can be performed to determine the relative haplotype dosage (e.g. if one of these haplotypes is overrepresented over the other haplotype). The classification threshold for this statistical procedure can be adjusted depending on the fractional fetal DNA concentration. In general, a higher fractional fetal DNA concentration can allow the threshold to be reached with fewer molecules. The classification threshold can also be adjusted depending on the number of successfully classified segments that one wishes to achieve across the genome or the genomic regions of interest.

Referring back to FIG. 1, in step 180, the fetal genome can be analyzed for mutations. For example, embodiments can be used to search for a panel of mutations causing genetic diseases in a particular population. Examples of mutations that can be detected using embodiments can be found from the Online Mendelian Inheritance in Man (www.ncbi.nlm.nih.gov/omim/getmorbid.cgi). These mutations can be searched for during steps 140-160; or as a separate step as described here. For example, in families in which the father is a carrier of one or more mutations which are absent in the mother, then the mutation(s) could be searched for from the analytic data (e.g. sequencing data) from the maternal biological sample.

Apart from detecting the actual mutation, one could also look for polymorphic genetic markers which are linked to the mutant or wildtype allele in the father or mother. For example, RHDO analysis may reveal that the fetus has inherited the haplotype from the mother that is known to carry a mutation for a disease. Embodiments of the invention can also be used for the noninvasive prenatal diagnosis of diseases caused by deletions of chromosomal regions, e.g. the Southeast Asian deletion causing alpha-thalassemia. In the scenario in which both the father and the mother are carriers of the deletion, if the fetus is homozygous for the deletion, and if massively parallel sequencing is performed on maternal plasma DNA, then there should be a reduction in the frequencies of DNA sequences originating from the deleted region in maternal plasma.

B. Example

This section describes an example of embodiments (e.g. of method 100) applied to single-nucleotide polymorphism (SNPs) in which the mother is heterozygous. The SNP alleles on the same chromosome form a haplotype, with the mother having a homologous pair of each chromosome, and thus two haplotypes. To illustrate how such a determination is performed, consider a segment on chromosome 3, e.g., as shown in FIG. 2.

Figure 2:
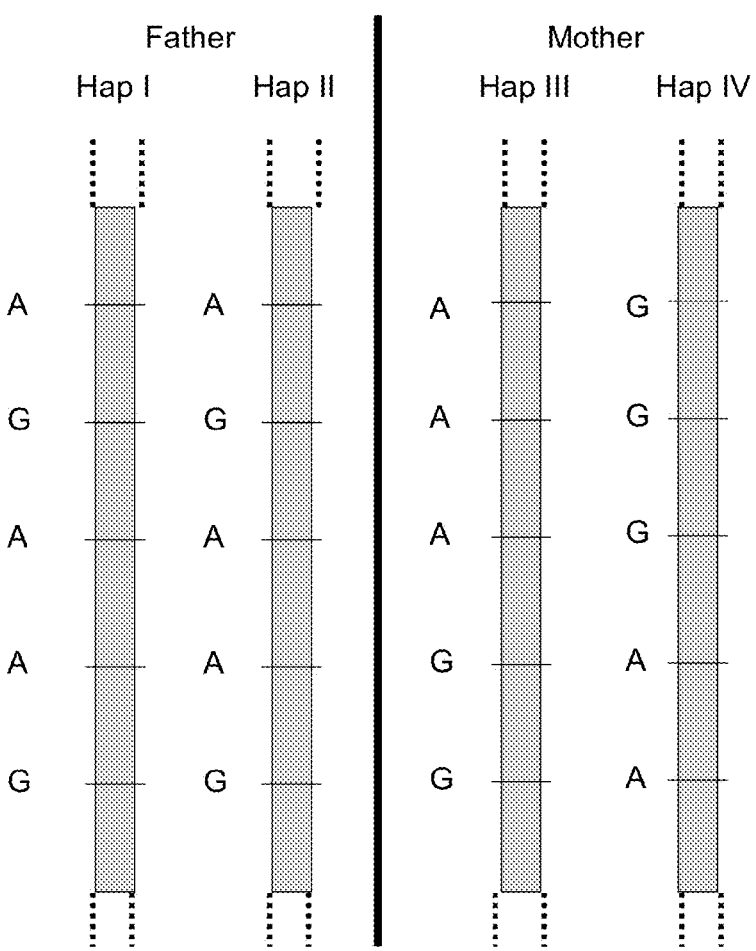
FIG. 2 shows two haplotypes for the father and two haplotypes for the mother for a particular segment of their respective genomic code according to embodiments of the present invention.

FIG. 2 shows two haplotypes for the father and two haplotypes for the mother for a particular segment of their respective genomic code. Five SNPs were found within this segment in which the father and mother were homozygous and heterozygous, respectively, for all 5 of these SNPs. The two homologous chromosomes of the father possessed the same haplotype (Hap), i.e., A-G-A-A-G (from top to bottom in FIG. 2). For simplicity, the paternal haplotypes are called Hap I and Hap II, bearing in mind that both of these are identical for this set of 5 SNPs. For the mother, two haplotypes were observed, namely Hap III, A-A-A-G-G and Hap IV, G-G-G-A-A.

The SNPs in this example could be further classified into two types. FIG. 3 shows the two types of SNPs according to embodiments of the present invention. Type A consists of those SNPs in which the paternal alleles were the same as those on the maternal haplotype III. Type B consists of those SNPs in which the paternal alleles were the same as those on the maternal haplotype IV.

These two types of SNPs can require slightly different mathematical handling. Thus, in the Type A scenario, the fetal inheritance of haplotype III would result in the overrepresentation of haplotype III, relative to haplotype IV, in maternal plasma (FIG. 4A). For example, looking at just one SNP 410 for ease of discussion, the allele A is inherited from the father, and if Hap III is inherited from the mother, then the fetus will be contributing two A alleles to the sample, which will cause an overrepresentation of A. If the fetus had inherited haplotype IV then no overrepresentation would be seen, since the fetus would also be heterozygous with A and G at the locus.

On the other hand, in the Type B scenario, the fetal inheritance of haplotype III would result in the equal representation of haplotype III and haplotype IV in maternal plasma (FIG. 4B). For example, looking against SNP 420, the inheritance of G from the father and A as part of Hap III would cause the fetus to contribute equal amounts of A and G at SNP 420, just like the mother. If the fetus had inherited haplotype IV, then overrepresentation would be observed as is evident from the discussion above.

FIGS. 5A and 5B shows the analysis of comparing relative amounts (e.g. counts) of fragments for each locus and whether a result of the comparison is to classify a particular haplotype as being inherited or not. Any genomic location in which there is a SNP which fits one of these genotype configurations of the father and mother (e.g. Type A or Type B scenarios) can be used for this example. From the maternal plasma sequencing data, one can focus on the number of sequenced molecules corresponding to a particular allele of the SNP. An SPRT analysis (or other comparison method) can be used to determine if there was any allelic imbalance between these alleles (Lo Y M D et al Proc Natl Acad Sci USA 2007; 104: 13116-13121).

FIG. 5A shows an analysis for type A SNPs. As shown, for each SNP, a SPRT comparison of the relative amounts (e.g. as defined by a separation value) to a cutoff value provides a classification. In one embodiment, if the classification threshold for SPRT was reached then the fetal inheritance of a particular maternal haplotype was concluded. Counting for the SPRT analysis can then be reset. Then, an analysis can move onto a neighboring SNP fitting the required genotype configuration, either from the telomeric-to-centromeric direction, or vice versa; and the new SPRT analysis can begin with this next SNP.

On the other hand, in one embodiment, if the classification for SPRT was not reached with the SNP, then we can also move onto a neighboring SNP in a similar fashion, except that the counts for the next SNP can be added to the previous one and then SPRT can again be performed. This process can continue until the classification threshold had been reached. FIG. 5A and FIG. 5B illustrate the operation of this process for Type A and Type B analyses. In one embodiment, the classifications are analyzed together to make a total classification for a region. For example, if a classification is obtained for a first group of SNPs and for the next group of SNPs, the classification of the two can be compared to see if the classification is consistent.

FIG. 6 illustrates the effect of changing the likelihood ratio for SPRT classification (Zhou W et al. Nat Biotechnol 2001; 19:78-81; Karoui N E et al. Statist Med 2006; 25:3124-33). In general a lower likelihood ratio for classification, e.g., 8, can allow classification to be made more easily. This can result in a larger number of classified regions within the genome. However, a number of such regions can be expected to be misclassified. On the other hand, a higher likelihood for classification, e.g., 1200, can only allow classification when more SNPs have been scored. This can result in a smaller number of classified regions within the genome. The number and proportion of misclassified regions can be expected to be lower when compared with situations when a lower classification threshold was used.

In one embodiment, a classification is made only if two consecutive SPRT classifications result in the same haplotype (referred to as the "two consecutive blocks" algorithm). In one aspect, the "two consecutive blocks" algorithm can increase the accuracy of classification. In some embodiments, for any stretch of sequence, an embodiment can first perform an SPRT analysis for Type A SNPs, and then do another SPRT analysis for the Type B SNPs. In one embodiment, one can consider the scenario for a stretch of sequence for which the Type A and Type B SNPs form two interlacing groups of genetic landmarks (e.g. SNPs). In embodiments using the "two consecutive blocks" algorithm, the two blocks can be of different types.

The SPRT results from the Type A and Type B analyses can allow one to check for concordance or discordance in their classification results. To enhance the classification accuracy, one embodiment ("interlacing approach") could only make a classification if both the Type A and Type B analyses for a given genomic region can yield consistent results. If the two analyses yield discordant results, we can look at the classification results of the two contiguous regions of classification next to the region, one at the centromeric end and the other one at the telomeric end. If these two contiguous regions yield concordant results, then we can classify the first region as a continuous haplotype with these two regions. If these two contiguous regions do not yield concordant results, then we can move onto the next two contiguous regions until concordance is seen. One variant of this theme is to move in just one direction and to take the classification results of the next one, or two, or even more contiguous regions as the results of the original region concerned. The general principle is to use the classification results of adjacent genomic regions to confirm the classification results of a particular region.

III. DETERMINATION OF THE PATERNAL ALLELES INHERITED BY THE FETUS

Figure 7:
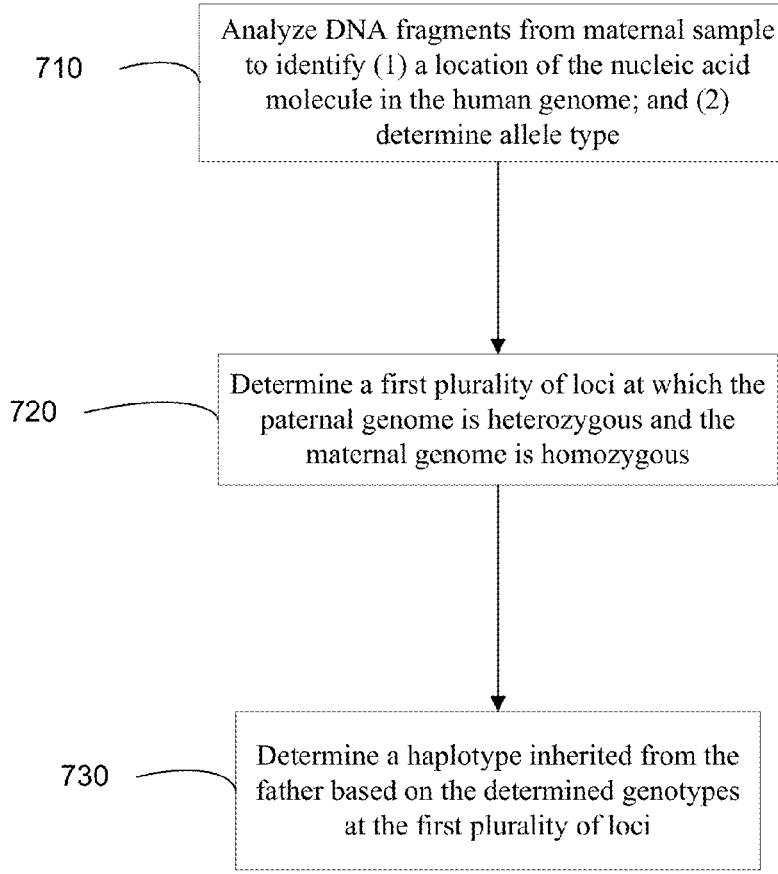
FIG. 7 is a flowchart of a method 700 of determining at least a portion of the genome of an unborn fetus of a pregnant female inherited from the father according to embodiments of the present invention.

FIG. 7 is a flowchart of a method 700 of determining at least a portion of the genome of an unborn fetus of a pregnant female inherited from the father. Method 700 analyzes nucleic acid molecules (fragments) from a biological sample obtained from the pregnant female to determine the genome of the fetus. The sample contains a mixture of maternal and fetal nucleic acids.

In step 710, each of a plurality of nucleic acid molecules from the biological sample are analyzed to identify a location of the nucleic acid molecule in the human genome, and determine an allele type of the nucleic acid molecule. Thus, genotypes of the nucleic acid molecules at a particular location (locus) can be determined in one embodiment. Any of the methods described above and elsewhere may be used for this analysis.

In step 720, a first plurality of loci are determined at which the paternal genome is heterozygous and the maternal genome is homozygous. In one embodiment, the first plurality of loci are obtained by determining the paternal and maternal genomes. The genomes can be mined for genomic loci in which the father is heterozygous and the mother is homozygous.

In step 730, the haplotype that is inherited by the unborn fetus from the father at the portion of the genome covered by the first plurality of loci is determined based on the determined genotypes at the first plurality of loci. In one embodiment, the allele of each of these loci which is possessed by the father, but absent in the genome of the mother, is sought for in the analytic data (e.g. sequencing data). The combination of these alleles would indicate the haplotypes of the chromosomes that the fetus has inherited from the father.

In another embodiment, if the haplotypes of each of the chromosomes or the chromosomal regions of interest in the father's genome is known, then one can also determine where meiotic recombination has occurred during spermatogenesis in the father. Hence, paternal meiotic recombination is seen when the haplotype of a stretch of DNA in a paternally-inherited chromosome differs between the fetus and the father. The inclusion of such recombination information can be useful when the analytic data (e.g. sequencing data) are used for the prenatal diagnosis of a genetic disease by linkage analysis to genetic polymorphisms.

IV. FATHER AND MOTHER ARE HETEROZYGOUS FOR A GENOMIC REGION

Embodiments can address a scenario in which the father and mother are heterozygous for a genomic region. This scenario can be particularly relevant in families in which the father and mother are consanguineous. When a disease is associated with a predominant mutation which has resulted from a large founder effect can also be relevant. In such circumstances, it is to be expected that if the father and mother of the unborn fetus are both carriers of the mutant gene, then the haplotype of the chromosome carrying the mutant copy of the gene can essentially be identical, except for the occurrence of meiotic recombination events. This type of analysis can be especially useful for autosomal recessive diseases such as cystic fibrosis, beta-thalassemia, sickle cell anemia, and hemoglobin E disease.

Figure 8:
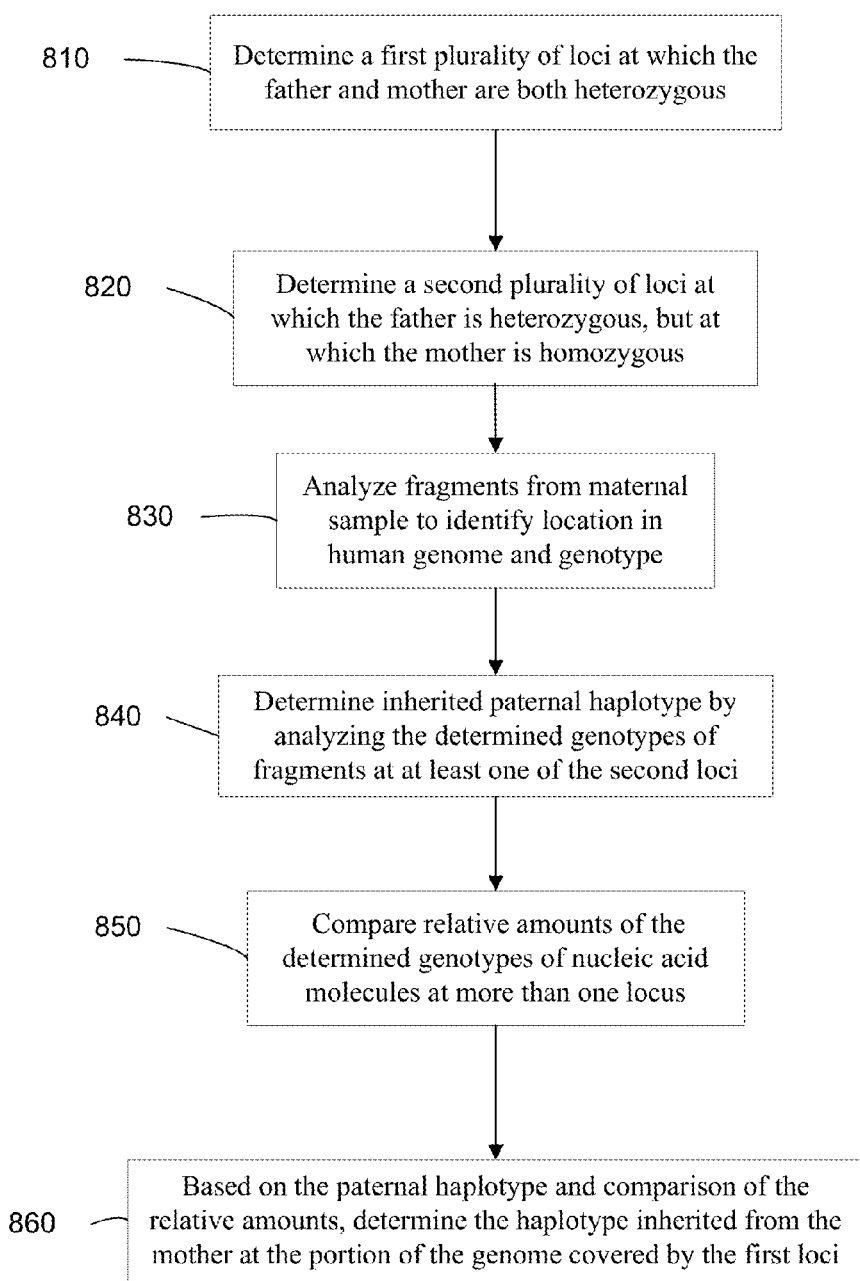
FIG. 8 is a flowchart of a method 800 for determining at least a portion of the genome of an unborn fetus in a region where the mother and father are heterozygous according to embodiments of the present invention.

FIG. 8 is a flowchart of a method 800 for determining at least a portion of the genome of an unborn fetus in a region where the mother and father are heterozygous according to embodiments of the present invention.

In step 810, a first plurality of loci are determined at which the father and mother are both heterozygous. In one embodiment, the first loci can be determined by any of the methods mentioned herein. For example, all or regions of the parental genomes can be sequenced, or different parts genotyped to find the first loci. Thus, each of the two paternal and each of the two maternal haplotypes at the first plurality of loci can be known.

Figure 9:
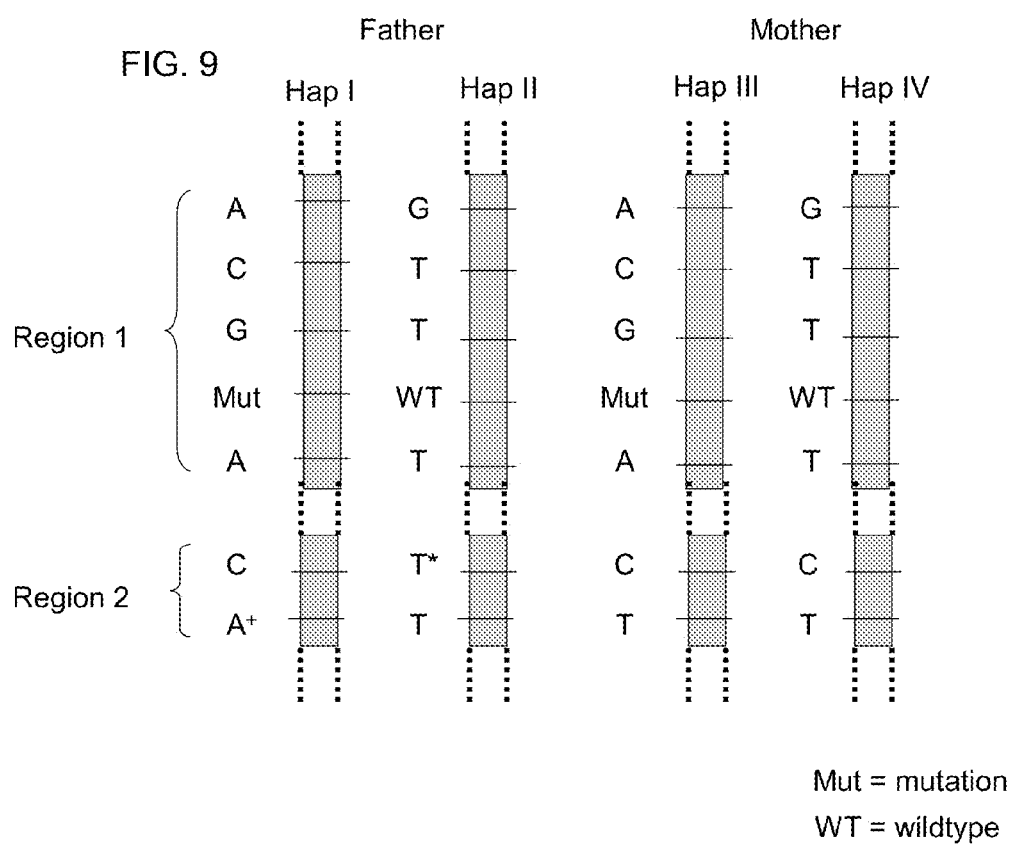
FIG. 9 shows haplotypes of a father and mother that are both heterozygous in a particular genomic region according to embodiments of the present invention.

As an example, FIG. 9 shows haplotypes of a father and mother that are both heterozygous in a particular genomic region. As shown, both parents have a mutant gene (allele) in region 1. Specifically, Hap I of the father and Hap III of the mother have the mutant gene. Also as shown, the father and mother can each have the other copy of the chromosome carrying the wildtype copy of the gene. Specifically, Hap II of the father and Hap IV of the mother have the wildtype gene. Thus, this example has relevance in determining whether a fetus has inherited a mutant gene. The chromosomes from the father and mother that carry the wildtype gene have an identical haplotype in the immediate vicinity of the gene, but might have divergent haplotypes further away from the gene. As this chromosome would likely have a diverse ancestral origin, this chromosome would unlikely have identical haplotypes between the father and mother throughout the whole chromosome.

In step 820, a second plurality of loci are determined at which the father is heterozygous, but at which the mother is homozygous. As shown, the first and second pluralities of loci are on the same chromosome. Region 2 shows such second loci. Region 2 can be chosen such that the father is heterozygous for one or more SNPs in this region while the mother is homozygous in this region.

In step 830, fragments from a sample of the pregnant female can be analyzed to identify a location in the human genome and a genotype. The location can be used to determine whether a fragment (nucleic acid molecule) includes one or more of the first loci or one or more of the second loci. This information can then be used to determine the haplotype inherited from the father and the haplotype inherited from the mother.

In step 840, which of the two paternal haplotypes has been inherited by the fetus is determined by analyzing the determined genotypes of the plurality of nucleic acid molecules from the biological sample at at least one of the second loci. For example, the SNP alleles which are uniquely present in the father's genome, but absent in the mother's genome, such as the T allele marked by * and the A allele marker by $^+$ in FIG. 9, can be sought for from the analytic data (e.g. location and genotype resulting from step 710) of the maternal biological sample. As can be done for method 700, if the T allele marked by * is detected from maternal plasma, then it means that haplotype II (Hap II) is inherited by the fetus from the father. Conversely, if the A allele marked by $^+$ is detected from maternal plasma, then it means that Hap I is inherited by the fetus from the father.

In step 850, comparing relative amounts of the determined genotypes of nucleic acid molecules at more than one of the first plurality of loci. In one embodiment, amounts at each locus are aggregated and the relative amounts of the maternal haplotypes are compared. The relative amounts can refer to counted numbers, size distributions, and any other parameter that can convey information as to which genotype is in the fetal genome at a particular locus.

In step 860, based on the paternal haplotype determined to be inherited by the fetus and based on the comparison of the relative amounts, determining the haplotype that is inherited by the unborn fetus from the mother at the portion of the genome covered by the first plurality of loci. Thus, an RHDO analysis (e.g. as described above) of SNPs in Region 1 from the analytic data of the maternal biological sample can be carried out to determine which one of the two maternal haplotypes has been inherited by the fetus, taking the paternal haplotype inherited by the fetus in Region 2 into consideration. In one embodiment, it is assumed that there is no recombination between Regions 1 and 2 when these regions are passed from the parents to the fetus.

For example, consider the scenario when the fetus has been determined to have inherited Hap I from the father through Region 2 analysis. Then, the fetal inheritance of Hap III (which is identical to Hap I at Region 1) from the mother will result in the overrepresentation of Hap III relative to Hap IV in maternal plasma. Conversely, if the fetus has inherited Hap IV from the mother, then equal representation of Hap III and Hap IV will be observed in maternal plasma.

As another example, consider the scenario when the fetus has been determined to have inherited Hap II from the father through Region 2 analysis. Then, the fetal inheritance of Hap IV (which is identical to Hap II at Region 1) from the mother will result in the overrepresentation of Hap IV relative to Hap III in maternal plasma. Conversely, if the fetus has inherited Hap III from the mother, then equal representation of Hap III and Hap IV will be observed in maternal plasma.

In the previous sections, we have deduced the fetal genome and the fractional fetal DNA concentration using the data obtained from the sequencing of the maternal plasma DNA, as well as the genotype information of the parents of the fetus. In the following sections, we describe embodiments for deducing the fractional fetal DNA concentration and fetal genotype without prior information of the maternal and paternal genotypes/haplotypes.

V. DETERMINATION OF FRACTIONAL FETAL DNA CONCENTRATION

In some embodiments, an optional step is to determine a fractional fetal DNA concentration. In various aspects, this fractional concentration can guide the amount of analysis (e.g. amount of sequencing required) or allow one to estimate the accuracy of the analysis for a given amount of data (e.g. depth of genome sequence coverage). The determination of the fractional fetal DNA concentration can also be useful for determining a cutoff to determine a classification of which haplotype and/or genotype are inherited.

In one embodiment, the fractional fetal DNA concentration can be determined by mining the analytic data (e.g. as can be obtained in step 140 and 710) for loci that are homozygous for the father and for the mother, but with different alleles. For example, for a SNP with two alleles, A and G; the father can be AA and the mother can be GG, and vice versa. For such loci, the fetus would be an obligate heterozygote. In the example above, the fetal genotype would be AG, and a proportion of allele A in the maternal sample can be used to determine the fractional fetal DNA concentration. In another embodiment, a statistical analysis can be made to determine a locus where the mother is homozygous and the fetus is heterozygous. In this manner, no prior information about the mother's genome or the paternal genome is needed.

As alternatives to mining the analytic data, the fractional fetal DNA concentration can also be determined by another approach, such as the use of PCR assays, digital PCR assays or assays based on mass spectrometry, on a panel of polymorphic genetic markers (Lun F M F et al Clin Chem 2008; 54: 1664-1672). Another alternative is to use one or more genomic loci which exhibit different DNA methylation between the fetus and mother (Poon L L M et al. Clin Chem 2002; 48: 35-41; Chan K C A et al. Clin Chem 2006; 52: 2211-2218; U.S. Pat. No. 6,927,028). As yet another alternative is to use an approximate fractional fetal DNA concentration determined from a reference population, e.g. at a similar gestational age. However, as the fractional fetal DNA concentration could vary from sample to sample, this latter approach may be expected to be less precise than if the concentration is measured specifically for the sample being tested.

A. Determining Fractional Concentration for Obligate Heterozygote

In embodiments where the fetus is an obligate heterozygote, one can determine the fractional fetal DNA concentration using the following series of calculations (e.g. using massively parallel sequencing). Let p be the counts of the fetal allele that is absent from the maternal genome. Let q be the counts of the other allele, i.e. the allele that is shared by the maternal and fetal genomes. Fractional fetal DNA concentration is given by the following equation:

$$\frac{2p}{p+q}$$

In one implementation, this calculation can be performed on the cumulative data across different polymorphic genetic loci or polymorphic genetic features that fulfill the parental genotype configuration (e.g. both parents being homozygous, but for different alleles).

B. Determination Based on Informative SNPs

The fractional concentration of fetal DNA can also be determined for any locus at which the mother is homozygous and the fetus is heterozygous, and not just when the mother is homozygous for one allele and the father is homozygous for a different allele. Both methods provide whether a locus is informative. The term "informative SNP" can be used in different contexts depending on what information is desired. In one context, the information is an allele in the fetal genome at a particular locus that is not present in the maternal genome at that locus. Thus, the subset of SNPs that the mother is homozygous and the fetus is heterozygous can be referred to as "informative SNPs" for the context of determining fetal DNA concentration. Instances where the mother and fetus are both heterozygous, but for at least one different allele, can also be used as an informative SNP. However, triallelic SNPs are relatively uncommon in the genome.

Figure 10:
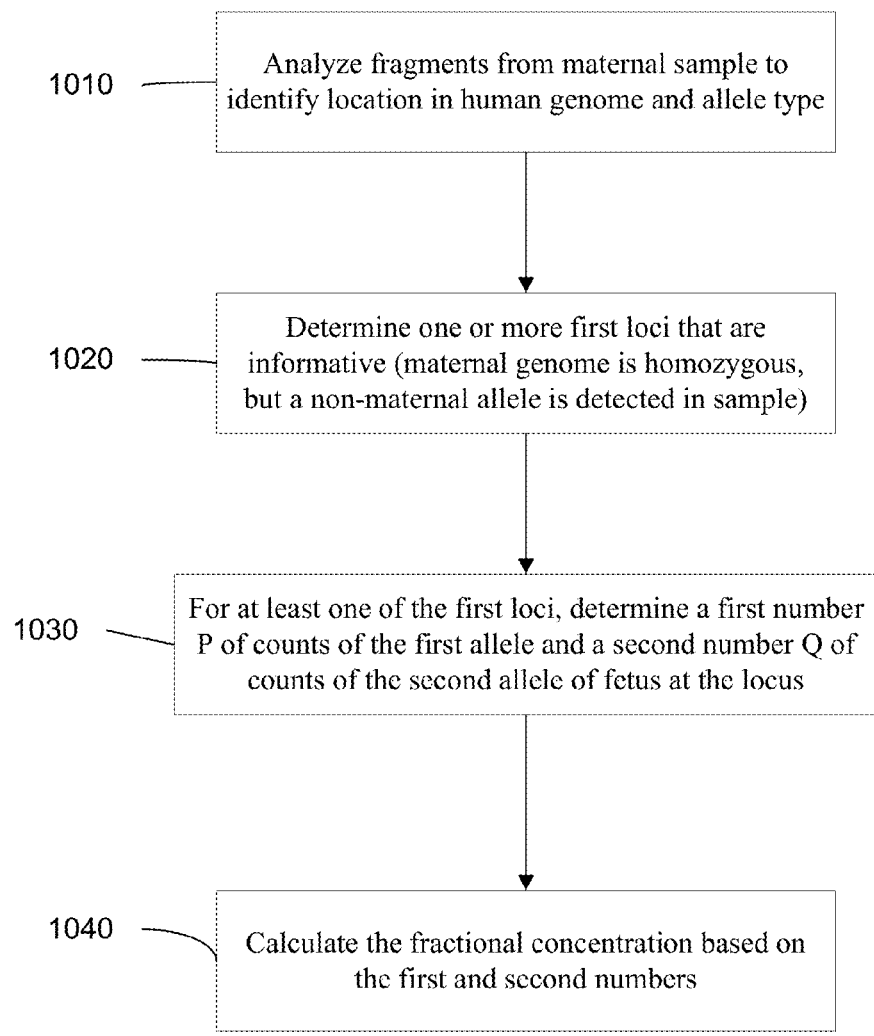
FIG. 10 is a flow chart illustrating a method 1000 for determining fractional concentration of fetal material in a maternal sample according to embodiments of the present invention.

FIG. 10 is a flow chart illustrating a method 1000 for determining fractional concentration of fetal material in a maternal sample according to embodiments of the present invention. In step 1010, fragments from a sample of the pregnant female can be analyzed to identify a location in the human genome and an allele type (which can lead to a genotype determination at the location). In one embodiment, the fragments are analyzed by sequencing a plurality of nucleic acid molecules from the biological sample obtained from the pregnant female. In other embodiments, real-time PCR or digital PCR can be used.

In step 1020, one or more first loci are determined to be informative. In some embodiments, the maternal genome is homozygous, but a non-maternal allele is detected in the sample at an informative locus. In one embodiment, the fetal genome is heterozygous at each first loci and the maternal genome is homozygous at each first loci. For example, the fetal genome can have a respective first and second allele (e.g. TA) at a first locus, and the maternal genome can have two of the respective second allele (e.g. AA) at the first locus. However, such loci may not be a priori known, e.g., in situations where the fetus is not an obligate heterozygote.

In one embodiment to determine an informative locus, the SNPs at which the mother is homozygous are considered. For SNPs that the mother is homozygous, the fetus is either homozygous for the same allele or is heterozygous. For example, if a SNP is polymorphic for A and T, and the mother has a genotype of AA, the genotype of the fetus is either AA or TA. In this case, the presence of the T allele in the maternal plasma sample would indicate the fetal genotype is TA instead of AA. Certain embodiments can address how much of a presence of the T allele indicates a genotype of TA by calculating a necessary cutoff, as is described below.

In step 1030, for at least one of the first loci, a first number p of counts of the respective first allele and a second number q of counts of the respective second allele are determined. In one embodiment, the counts of the fetal-specific (the T allele) and the shared (the A allele) alleles in maternal plasma can be determined by a variety of methods, for example, but not limited to real-time PCR, digital PCR, and massively parallel sequencing.

In step 1040, the fractional concentration is calculated based on the first and second numbers. In one embodiment, in a pregnant woman with genotype AA and the genotype of her fetus being TA, the fractional fetal DNA concentration (f) can be calculated using the equation: $f=2\times p/(p+q)$, where p represents the counts for the fetal-specific allele (allele T) and q represents the counts for the allele shared by the mother and the fetus (allele A).

In another embodiment, by the use of multiple informative SNPs, the fractional concentration of fetal DNA in maternal plasma can be estimated with increased accuracy. For the use of the allele counts of multiple SNPs (a total of n SNPs), the fractional concentration of fetal DNA (f) can be calculated using the equation $$f = \frac{\sum_{i=1}^{n} 2p_i}{\sum_{i=1}^{n} (p_i + q_i)}$$

where $p_i$ represents the counts for the fetal-specific allele for the informative $SNP_i$; $q_i$ represents the counts for the allele shared by the mother and the fetus for the informative $SNP_i$; and n represents the total number of informative SNPs. The use of the allele counts of multiple SNPs can increase the accuracy of the estimation of the fractional fetal DNA concentration.

C. Fractional Concentration without Explicit Genetic Information of Parents

A method for determining the fractional fetal DNA concentration in a maternal plasma sample which does not require prior information regarding the genotypes of the fetus and the mother is now described. In one embodiment, the identification of informative SNPs is made from the counts of different alleles at these SNP loci in maternal plasma. Thus, method 1000 can be used, along with the determination of the informative SNPs based on embodiments described below. First, a description of probabilities is provided to help understand a calculation of a cutoff that is used to identify informative SNPs.

In one embodiment, the probability of detecting the fetal-specific allele follows the Poisson distribution. The probability (P) of detecting the fetal-specific allele can be calculated using the following equation: $P=1-\exp(-f\times N/2)$, where f represents the fractional concentration of fetal DNA in the maternal plasma sample, N represents the total number of molecules corresponding to this particular SNP locus being analyzed; and exp( ) represents the exponential function. In one aspect, P can be considered an expected distribution as it is not a distribution resulting from measuring an amount of molecules across many samples. In other embodiments, other distributions can be used.

Assuming that the fractional concentration of fetal DNA is 5% (a typical value for the first trimester pregnancy) and 100 molecules (maternal+fetal) corresponding to this SNP locus are analyzed (equivalent to the amount contained in 50 diploid genomes), the probability of detecting the fetal-specific allele (the T allele) is $1-\exp(-0.05\times100/2)=0.92$. The probability of detecting the fetal-specific allele would increase with the fractional fetal DNA concentration and the number of molecules being analyzed for the SNP locus. For example, if the fetal DNA concentration is 10% and 100 molecules are analyzed, the probability of detecting the fetal-specific allele is 0.99.

Therefore, at a SNP locus for which the mother is homozygous, the presence of an allele different from the maternal one in maternal plasma can indicate that the SNP is "informative" for the calculation of the fractional fetal DNA concentration. The probability of missing any informative SNP can be dependent on the number of molecules analyzed. In other words, for any desired confidence of detecting the informative SNPs, the number of molecules that needs to be analyzed to obtain a desired accuracy can be calculated according to the Poisson probability function.

Using the above analysis, some embodiments can determine if a locus is informative or not when the genotype of the mother is not known. In one embodiment, loci at which two different alleles are detected in the maternal plasma sample are identified. For example, for a SNP locus with two possible alleles A and T, both the A and the T alleles are detected in the maternal plasma.

Figure 11:
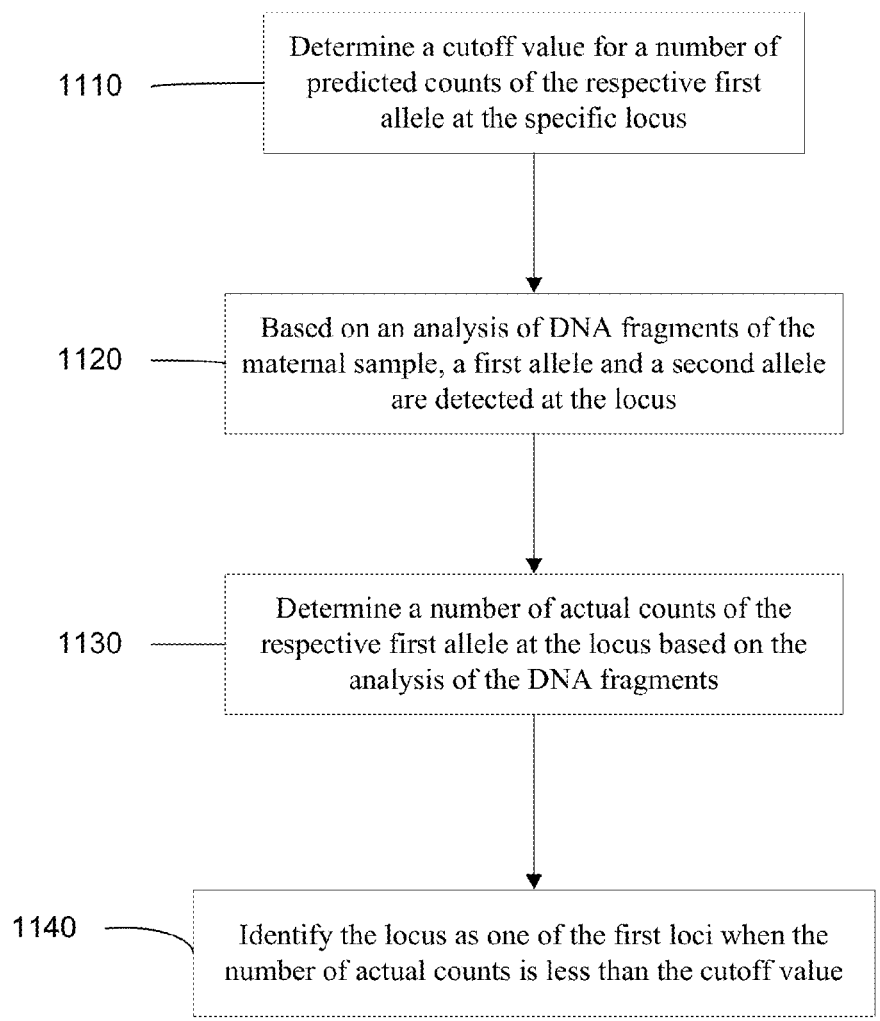
FIG. 11 is a flowchart of a method for determining whether a locus is informative according to embodiments of the present invention.

FIG. 11 is a flowchart of a method 1100 for determining whether a locus is informative according to embodiments of the present invention. In one embodiment, method 1100 can be used to implement step 1020 of method 1000. In another embodiment, one step of method 1100 is to determine a cutoff value based on a statistical distribution, and another uses the cutoff value to determine whether a locus (SNP) is informative.

In step 1110, a cutoff value is determined for a number of predicted counts of the respective first allele at the specific locus. In one implementation, the cutoff value predicts whether the maternal genome is homozygous and the fetal genome is heterozygous. In one embodiment, the cutoff value is determined based on a statistical distribution of numbers of counts for different combinations of homozygosity and heterozygosity at the specific locus. For example, an allelic frequency distribution can be predicted using the Poisson distribution function.

In step 1120, based on an analysis of the nucleic acid molecules of the maternal sample (e.g. from step 1010), a first allele and a second allele are detected at the locus. For example, a set of fragments could be mapped to the locus being analyzed and the first allele or the second allele was detected. The first allele can correspond to one of the respective first alleles from step 1020, and the second allele can correspond to one of the respective second alleles. In one embodiment, if two different alleles are not detected, then it is known that the locus is not informative.

In step 1130, a number of actual counts of the respective first allele at the locus is determined based on the analysis of the nucleic acid molecules. For example, sequencing results of the plurality of nucleic acid molecules can be counted to determine the number of times a fragment having a genotype of the first allele is mapped to the locus.

In step 1140, the locus is identified as one of the first loci based on a comparison of the number of actual counts to the cutoff value. In one aspect, a cutoff value can be used to differentiate between three possibilities: (a) the mother is homozygous (AA) and the fetus is heterozygous (AT); (b) the mother is heterozygous (AT) and the fetus is heterozygous (AT); and (c) the mother is heterozygous (AT) and the fetus is homozygous for (AA) or (TT). For the sake of illustration, the examples below assume the fetal genotype to be AA in scenario (c). However, the calculation would be the same if the genotype of the fetus is TT. An informative locus would have the possibility (a).

In one embodiment, the locus is identified as one of the first loci when the number of actual counts is less than the cutoff value. In another embodiment, a lower threshold can also be used to ensure that a spurious mapping did not occur.

Embodiment for determining the cutoff is now described. Based on the physiologically possible fractional fetal DNA concentration (this information is available from previous studies) and the total number of molecules corresponding to the SNP locus, the distribution of the allelic counts can be predicted for the three possible scenarios above. Based on the predicted distribution, a cutoff value can be determined for interpreting the observed allelic counts in maternal plasma to determine if a SNP is "informative" (i.e. scenario (a)) or not.

The fractional concentration of fetal DNA typically ranges from 5% to 20% in early pregnancy and ranges from 10% to 35% in late pregnancy (Lun et al., Microfluidics digital PCR reveals a higher than expected fraction of fetal DNA in maternal plasma. Clin Chem 2008; 54:1664-72). Thus, in one embodiment, the predicted distributions of the allelic counts for 5% and 20% fractional concentration of fetal DNA were determined.

Figure 12A:
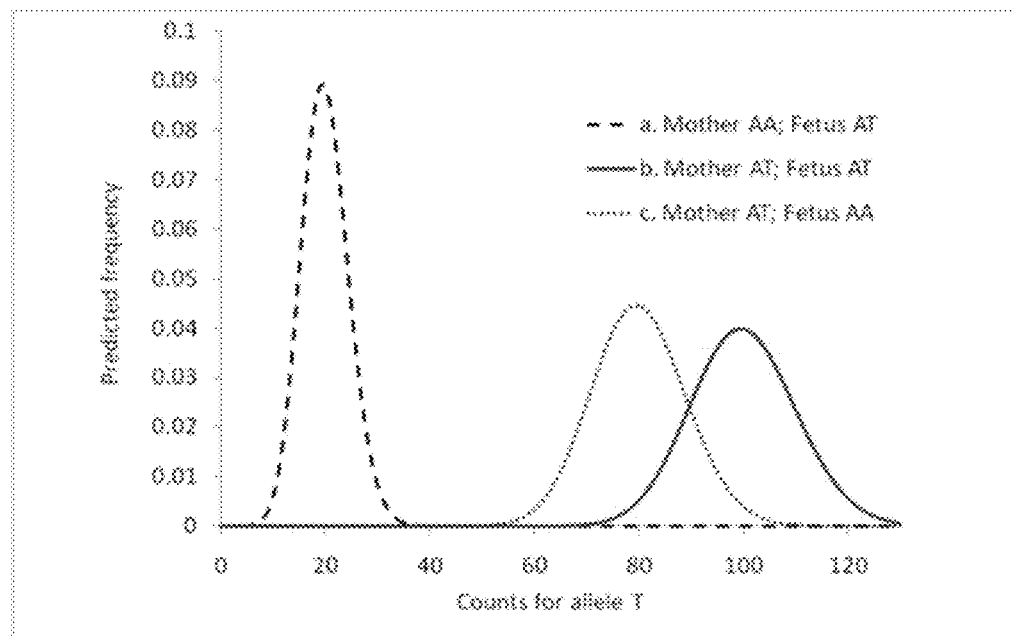
FIGS. 12A and 12B show the predicted distribution of the counts for allele T (the less abundant allele in scenarios (a) and (c)) for the three scenarios with an assumed fractional fetal DNA concentration of 20% and 5%, respectively, according to embodiments of the present invention.
Figure 12B:
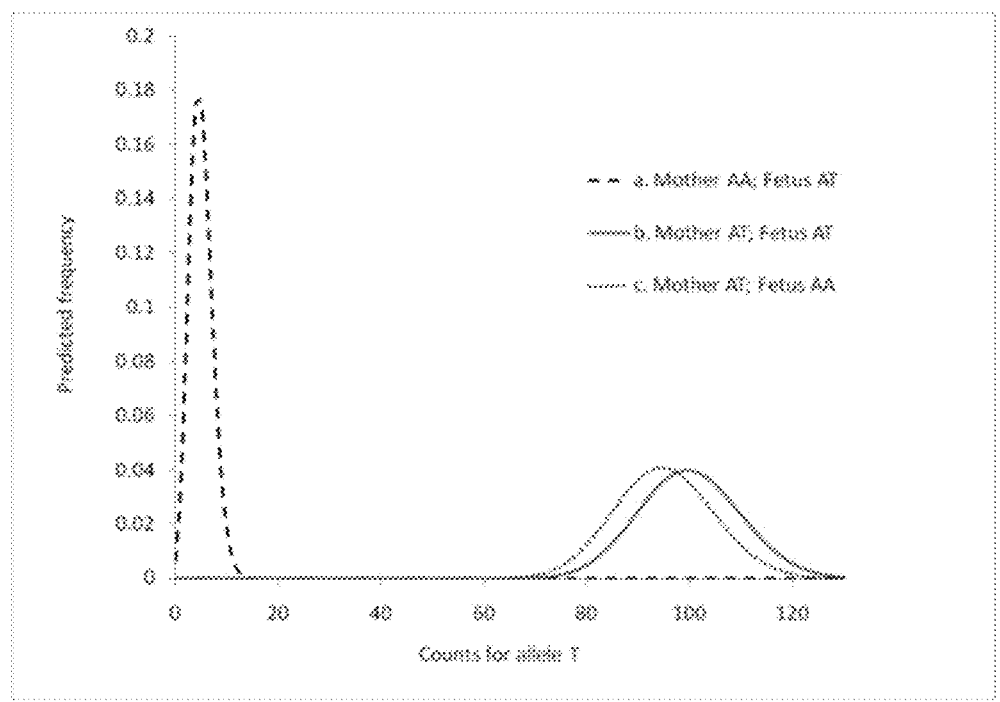

FIG. 12A shows the predicted distribution of the counts for allele T (the less abundant allele in scenarios (a) and (c)) for the three scenarios with an assumed fractional fetal DNA concentration of 20%. FIG. 12B shows the predicted distribution of the counts for allele T (the less abundant allele for scenarios (a) and (c)) for the three scenarios with the assumption of 5% fetal DNA. In both predicted models, a total of 200 molecules were assumed to be analyzed for the SNP locus.

Using the presence of 40 counts of the less abundant allele (the T allele) as a cutoff, the three possibilities can be statistically discriminated. In other words, for any SNP locus with two alleles detected in the maternal plasma and with a total of 200 molecules being analyzed, if the allelic frequency of the minor allele (the less abundant allele) is less than 40, the SNP locus can be regarded as "informative". For fractional fetal DNA concentrations of 5% and 20%, the differentiation of "informative" SNPs (scenario (a)) from the SNPs for which the mother is heterozygous (scenarios (b) and (c)) would be 100% accurate.

In practice, the total number of molecules detected can be different for different SNPs. For each SNP locus, a specific predicted distribution curve can be constructed by taking into account the total number of molecules detected in the maternal plasma sample covering the SNP locus. In other words, the count cutoff for determining whether a SNP is informative or not can vary among SNPs and depends on the number of times the SNP locus has been counted.

The following table shows the allele counts of three SNP loci in maternal plasma for a maternal plasma sample that was sequenced. For each of the three SNPs, two different alleles are detected in the maternal plasma sample. The total numbers of counts detected in maternal plasma corresponding to these three SNPs are different.

| SNP locus | SNP id | Allele (counts) | Allele (counts) | Total no. of counts |
|---|---|---|---|---|
| 1. | rs3107146 | A (10) | G (163) | 173 |
| 2. | rs7522344 | G (9) | T (112) | 121 |
| 3. | rs2272908 | A (72) | G (62) | 134 |

Figure 13A:
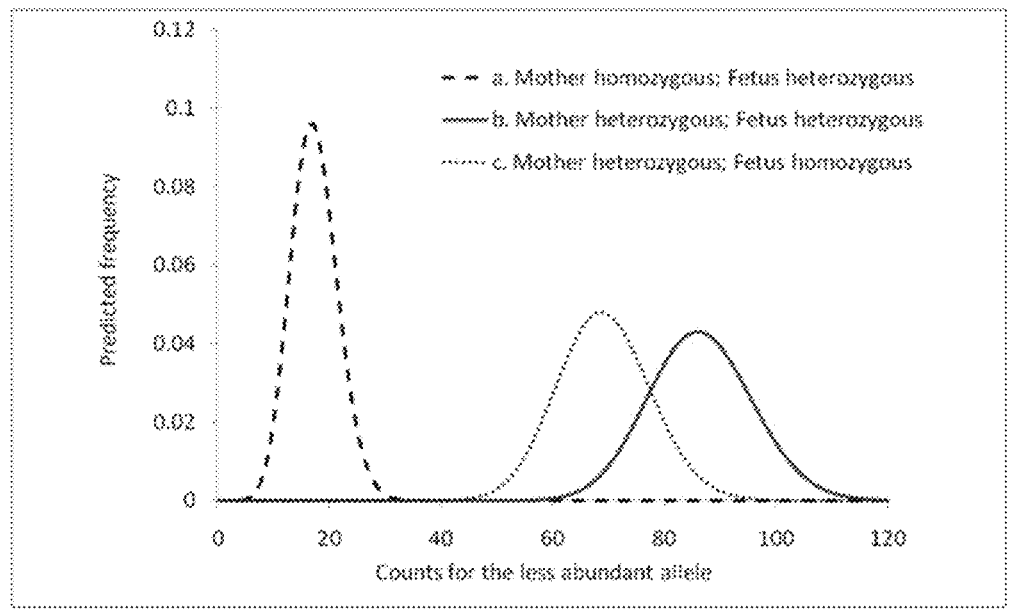
FIGS. 13A, 13B, and 14 show the predicted distributions for the counts of the less abundant allele for a fractional fetal DNA concentration of 20%, each for different total counts of molecules corresponding to a SNP according to embodiments of the present invention.
Figure 13B:
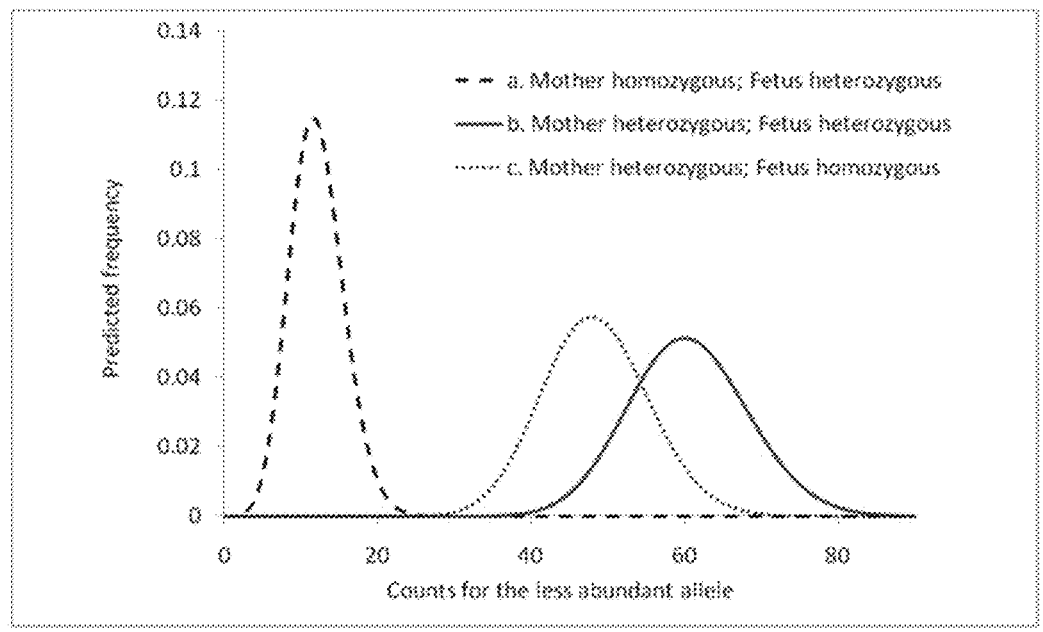
Figure 14:
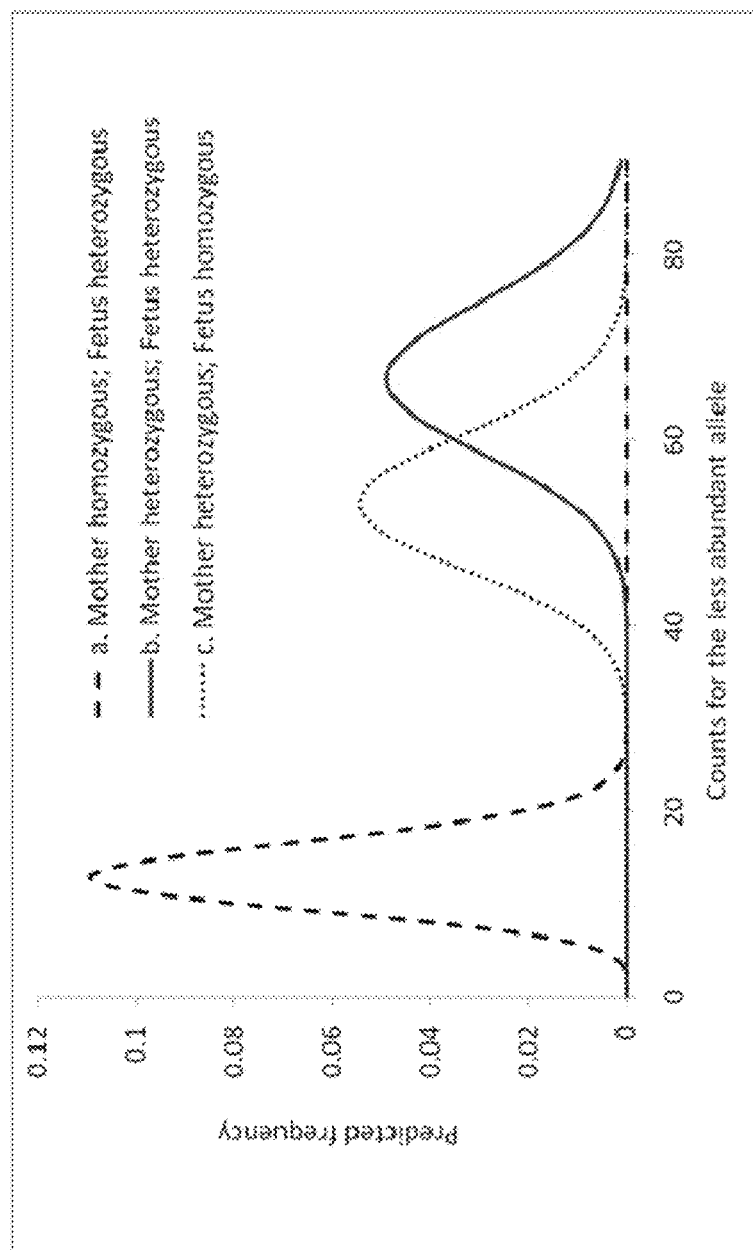

The predicted distributions for the counts of the less abundant allele for a fractional fetal DNA concentration of 20% and different total counts of molecules corresponding to a SNP are shown in FIGS. 13A, 13B, and 14. The predicted distributions were drawn using an assumed fetal DNA concentration of 20% because this represents the higher limit of fetal DNA concentration in the first trimester. The higher the fetal DNA concentration, the more overlap is expected between the distribution curves of the minor allele for which the mother is homozygous for the major allele against that when the mother is heterozygous. Thus, it is more specific to derive cutoffs for the minor allele counts using a higher fetal DNA concentration for the prediction of informative SNPs.

FIG. 13A shows a predicted distribution for the counts of the less abundant allele with a total number of 173 molecules and fractional fetal DNA concentration of 20%. In one embodiment, based on this distribution, a cutoff criterion of less than 40 for the counts of the less abundant allele can be suitable for identifying the informative SNPs. As the counts for the A allele is 10, the SNP locus no. 1 is regarded as "informative" for the calculation of the fractional fetal DNA concentration.

FIG. 13B shows a predicted distribution for the counts of the less abundant allele with a total number of 121 molecules and fractional fetal DNA concentration of 20%. In one embodiment, based on this distribution, a cutoff value of less than 26 for the counts of the less abundant allele can be suitable for identifying the informative SNPs. As the number of counts for the T allele is 9, the SNP locus no. 2 is regarded as "informative" for the calculation of the fractional fetal DNA concentration.

FIG. 12 shows a predicted distribution for the counts of the less abundant allele with a total number of 134 molecules and fractional fetal DNA concentration of 20%. In one embodiment, based on this distribution, a cutoff value of less than 25 for the counts of the less abundant allele can be suitable for identifying the informative SNPs. As the number of counts for the T allele is 62, the SNP locus no. 3 is regarded as "not informative" and would not be used for the calculation of fetal DNA fractional concentration.

In some embodiments, using the equation $f=2\times p/(p+q)$, the fractional concentration of fetal DNA can be calculated using the allele counts for SNP 1 and 2 and combined. The results are shown below.

| Calculation based on SNP locus | Fractional concentration of fetal DNA |
|---|---|
| 1. | $10 \times 2/(10 + 163) = 11.6\%$ |
| 2. | $9 \times 2/(9 + 112) = 14.9\%$ |
| 1. and 2. | $(10 + 9) \times 2/(10 + 9 + 163 + 112) = 12.9\%$ |

D. Determination of Depth Coverage of the Fetal Genome

Besides obtaining a fractional concentration, embodiments can determine a percentage coverage of the fetal genome that the analytic procedure (e.g. sequencing) in step 1010 has accomplished. In some embodiments, informative loci can be used to determine the percentage of coverage. For example, any of the examples from above can be used. In one embodiment, loci at which the fetus is an obligate heterozygote can be used. In another embodiment, loci at which the fetus is determined to be heterozygous and the mother is homozygous may be used (e.g. using method 1100).

The fragments that have been mapped to the informative loci can be used to determine a proportion of coverage. In one embodiment, a proportion of loci of the first plurality of loci in which a respective first allele is detected from the sequencing results is determined. For example, if the fetus is TA at a locus and the mother is AA at the locus, then the allele T should be detected in the sequencing results if that locus has been sequenced. Thus, the proportion of the fetal genome that has been sequenced from the biological sample can be calculated based on this proportion. In one embodiment, the proportion of the first loci where the fetal-specific allele is seen can be taken as the percentage coverage of the fetal genome. In other embodiments, the proportion can be modified based on where the loci are at. For example, a percentage coverage can be determined for each chromosome. As another example, the percentage can be estimated at less than the proportion if the first loci do not form a good representation of the genome. As another example, a range might be provided where the proportion is one end of the range. While a high percentage, i.e. approaching 100%, signifies close to complete coverage of the fetal genome, most genetic diseases can be diagnosed with much less than 100% coverage, e.g. 80%, or 50%, or less.

VI. NO PRIOR INFORMATION OF MATERNAL AND PATERNAL GENOME

In previous sections, some embodiments have determined a genetic map of a fetus (or a portion of a fetal genome) when the haplotypes of the mother and the genotypes of the father are known. Other embodiments have demonstrated that fractional fetal DNA concentration can be determined by analyzing the maternal plasma DNA without prior knowledge about the genotypes of the mother, the father, or the fetus. In yet other embodiments, we now further describe a method for determining the genetic map of a fetus (or a portion of a fetal genome) using RHDO analysis without prior information of the maternal and paternal genotypes/haplotype(s).

In one embodiment, the information of reference (e.g. common or known) haplotypes of the population in which the parents belong to is used. This information can be used for deducing the maternal and paternal haplotypes. An example is used to illustrate the principle of this method. Information concerning such reference haplotypes can be obtained, for example, from the website of the International HapMap Project (hapmap.ncbi.nlm.nih.gov/).

Figures 15A, 15B:
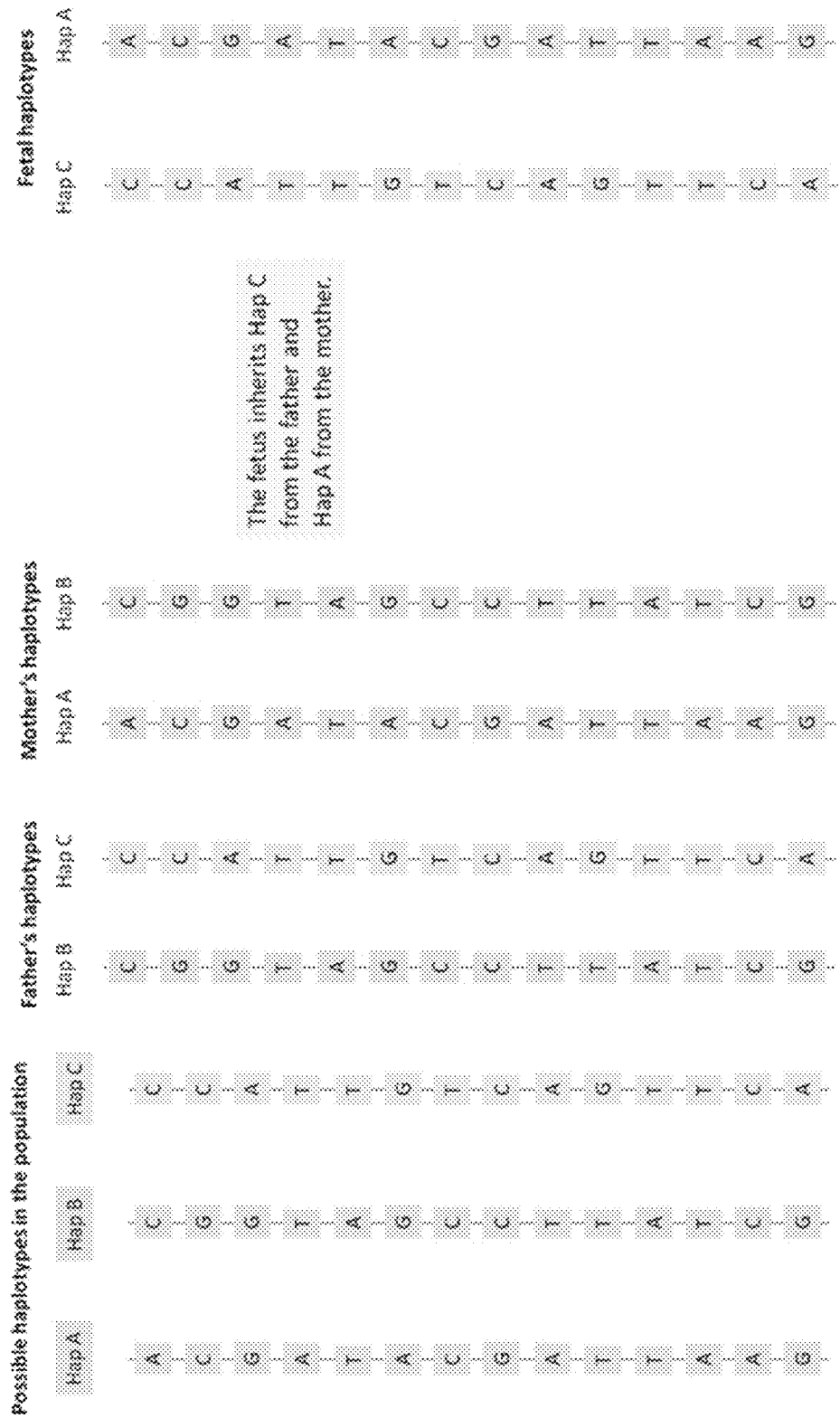
FIGS. 15A and 15B shows examples of reference haplotypes, parental haplotypes taken from the reference haplotypes, and a resulting fetal haplotypes according to embodiments of the present invention. Hap A=SEQ ID NO:1; Hap B=SEQ ID NO:2; Hap c=SEQ ID NO:3.

As part of an illustrative example, assume that three reference haplotypes (Hap A, Hap B and Hap C as shown in FIG. 15A) are present in the population. Each of these three haplotypes consists of 14 SNP loci and, for each locus, there are two possible alleles. In this example, the father possesses Hap B and Hap C whereas the mother possesses Hap A and Hap B, as shown in FIG. 15B. This example assumes that the fetus inherits Hap A from the mother and Hap C from the father. Therefore, the fetus possesses Hap A and Hap C, as shown in FIG. 15B.

Figure 16:
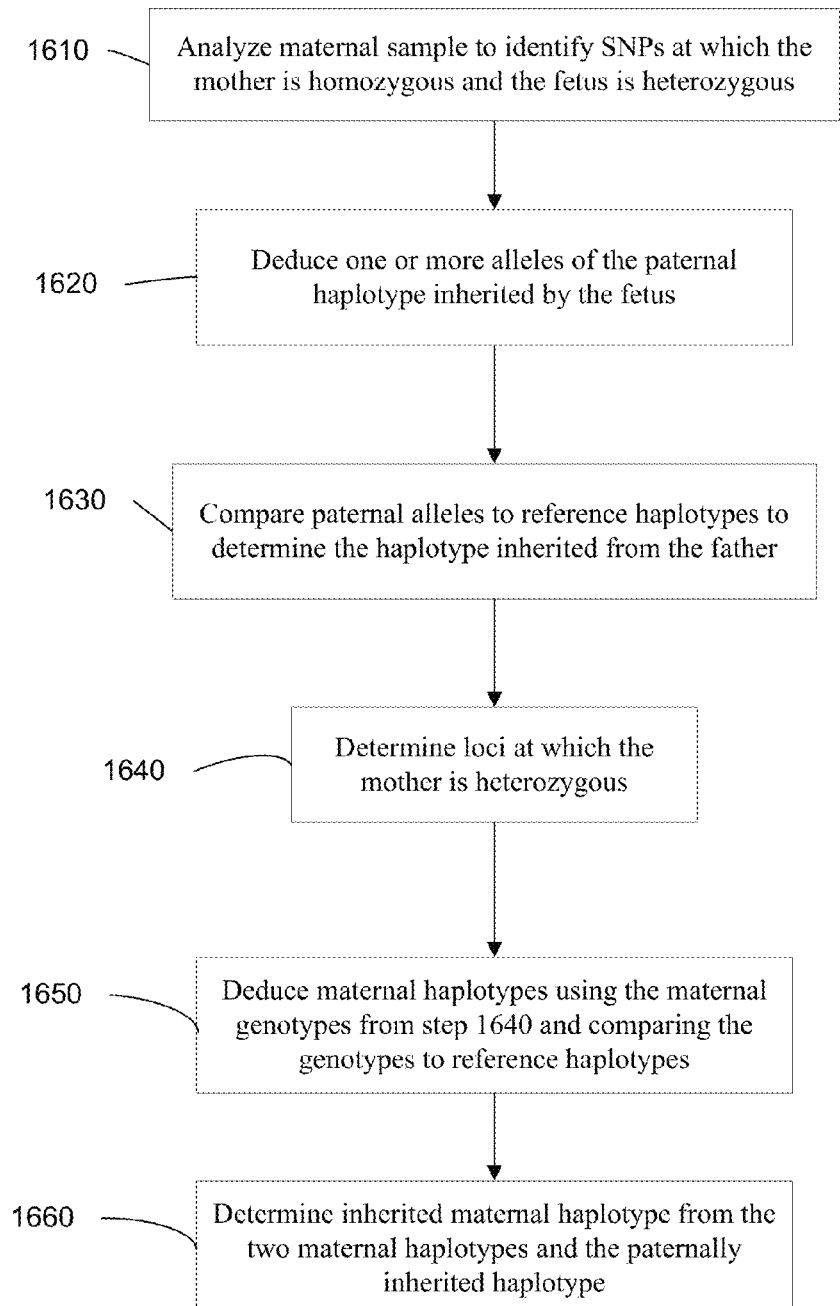
FIG. 16 is a flowchart of a method 1600 for determining at least part of a fetal genome when a set of reference haplotypes are known, but the parental haplotypes are not known, according to embodiments of the present invention.

FIG. 16 is a flowchart of a method 1600 for determining at least part of a fetal genome when a set of reference haplotypes are known, but the parental haplotypes are not known, according to embodiments of the present invention.

In step 1610, the maternal sample can be analyzed to identify SNPs at which the mother is homozygous and the fetus is heterozygous. This analysis can be done in a similar fashion as a determination of whether a locus is informative, as described above. Thus, in one embodiment, methods 1000 and/or 1100 can be used. In other embodiments described above, the maternal and paternal genomes can be analyzed to determine information to perform the fetal genome mapping.

Figure 17:
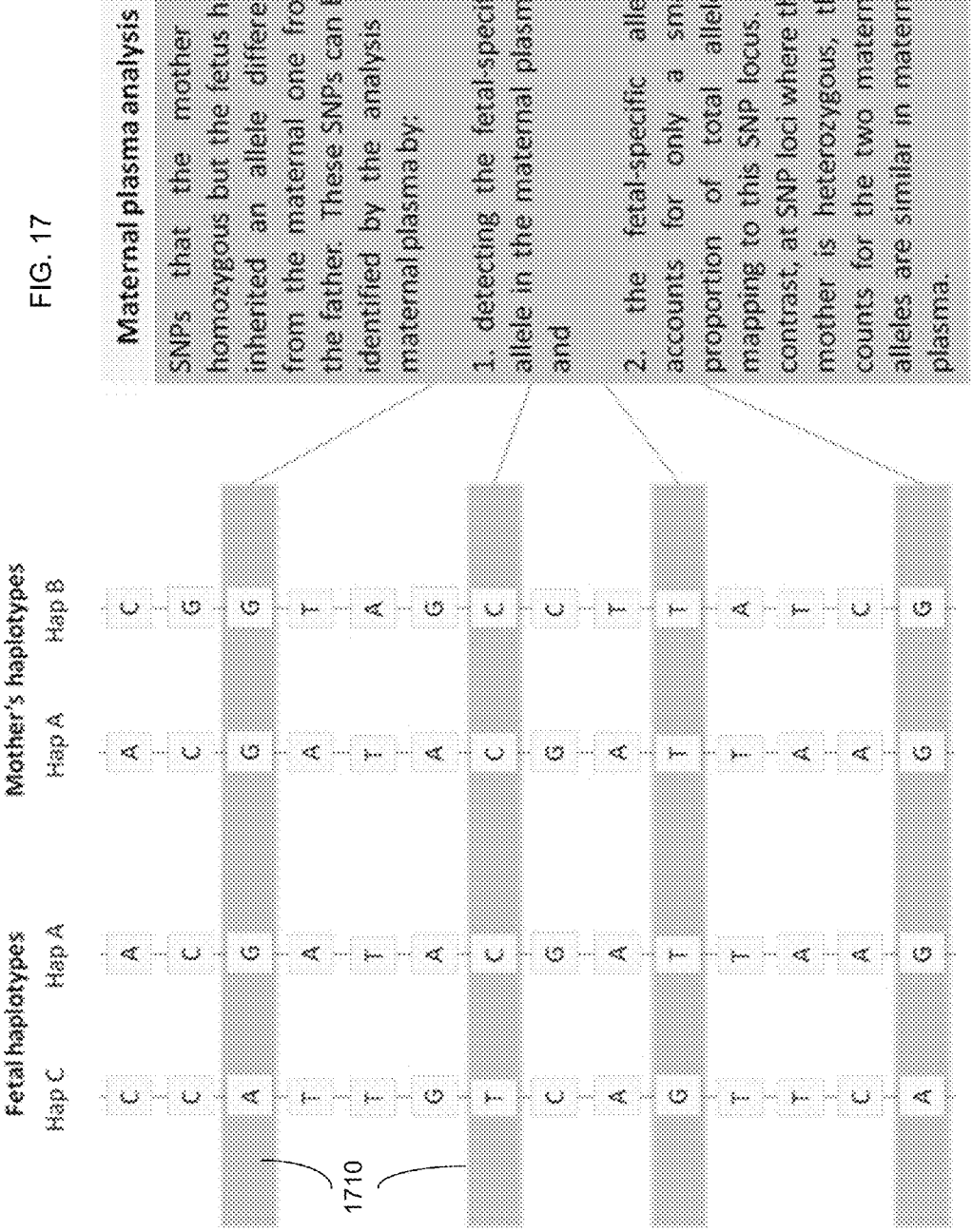
FIG. 17 shows an example of determining informative loci from analysis of DNA fragments from a maternal sample according to embodiments of the present invention. Hap A=SEQ ID NO:1; Hap B=SEQ ID NO:2; Hap c=SEQ ID NO:3.

FIG. 17 shows an example of determining informative loci from analysis of DNA fragments from a maternal sample. For each of the 14 loci, the counts of the two alleles for each locus are determined. The counts of these alleles can be determined, for example but not limited to, using real-time PCR, digital PCR, and massively parallel sequencing. For each of these loci, two different alleles would be detected in the maternal plasma. In contrast to those SNPs at which the mother is heterozygous, the proportion of the two alleles would be significantly different. The fetus-specific allele (the allele that the fetus inherits from the father) would be much less abundant compared with the maternal allele. The informative loci 1710 are marked in FIG. 17.

In step 1620, one or more alleles of the paternal haplotype inherited by the fetus are deduced. In one embodiment, each of the loci 1710 can be used to determine the inherited parternal haplotype. For example, the paternal allele that the fetus has inherited can be identified as the fetal-specific allele for loci 1720 because the fetal-specific allele is the allele is much less abundant than the maternal allele in the maternal sample.

In step 1630, the paternal alleles are compared to the reference haplotypes to determine the haplotype inherited from the father. In certain embodiments, a number of possible fetal haplotypes can be deduced, each with its own probability. One or more of the most likely fetal haplotypes can then be used for subsequent analysis, or for clinical diagnosis.

Figure 18:
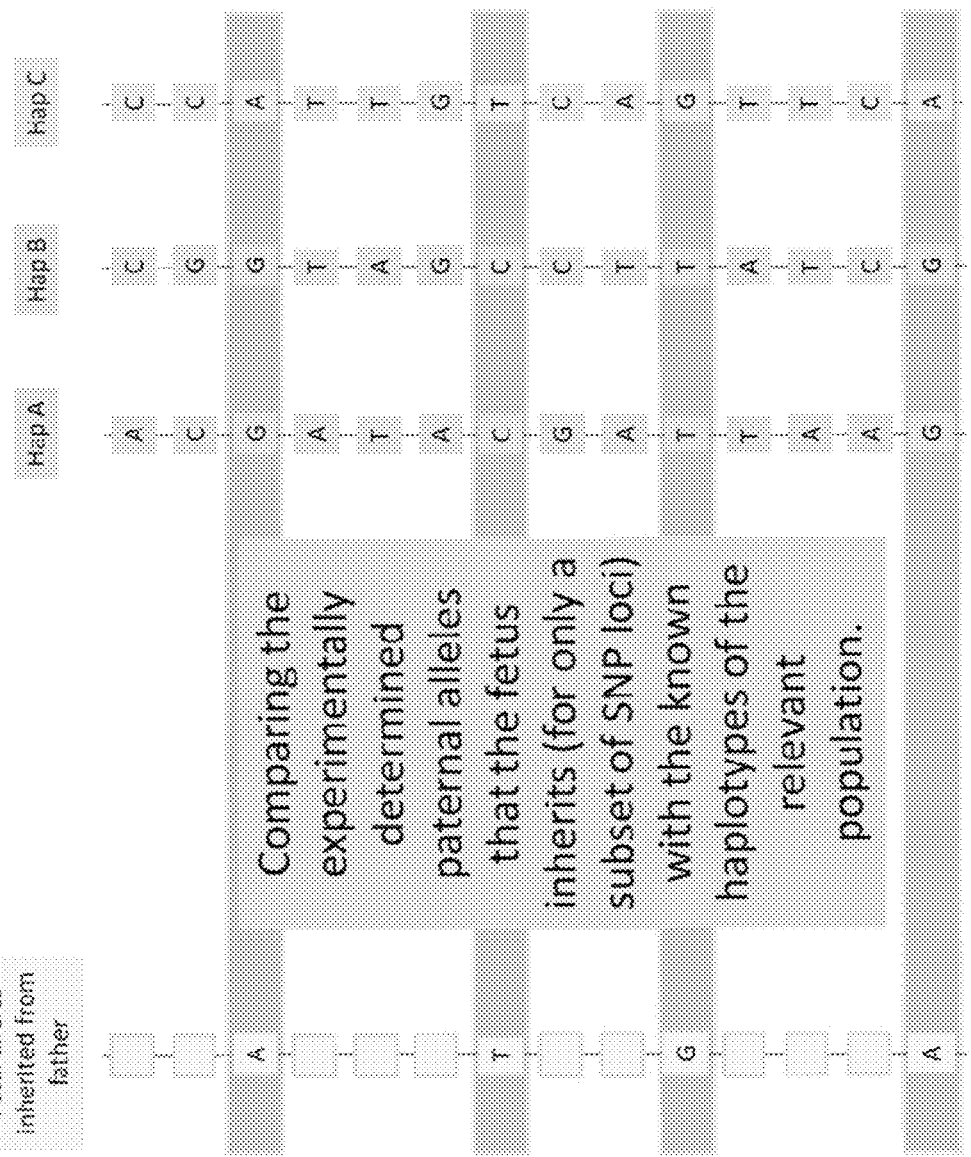
FIG. 18 shows the three reference haplotypes (Hap A (SEQ ID NO:1), Hap B (SEQ ID NO:2) and Hap C (SEQ ID NO:3)) and the paternal alleles.
Figure 19:
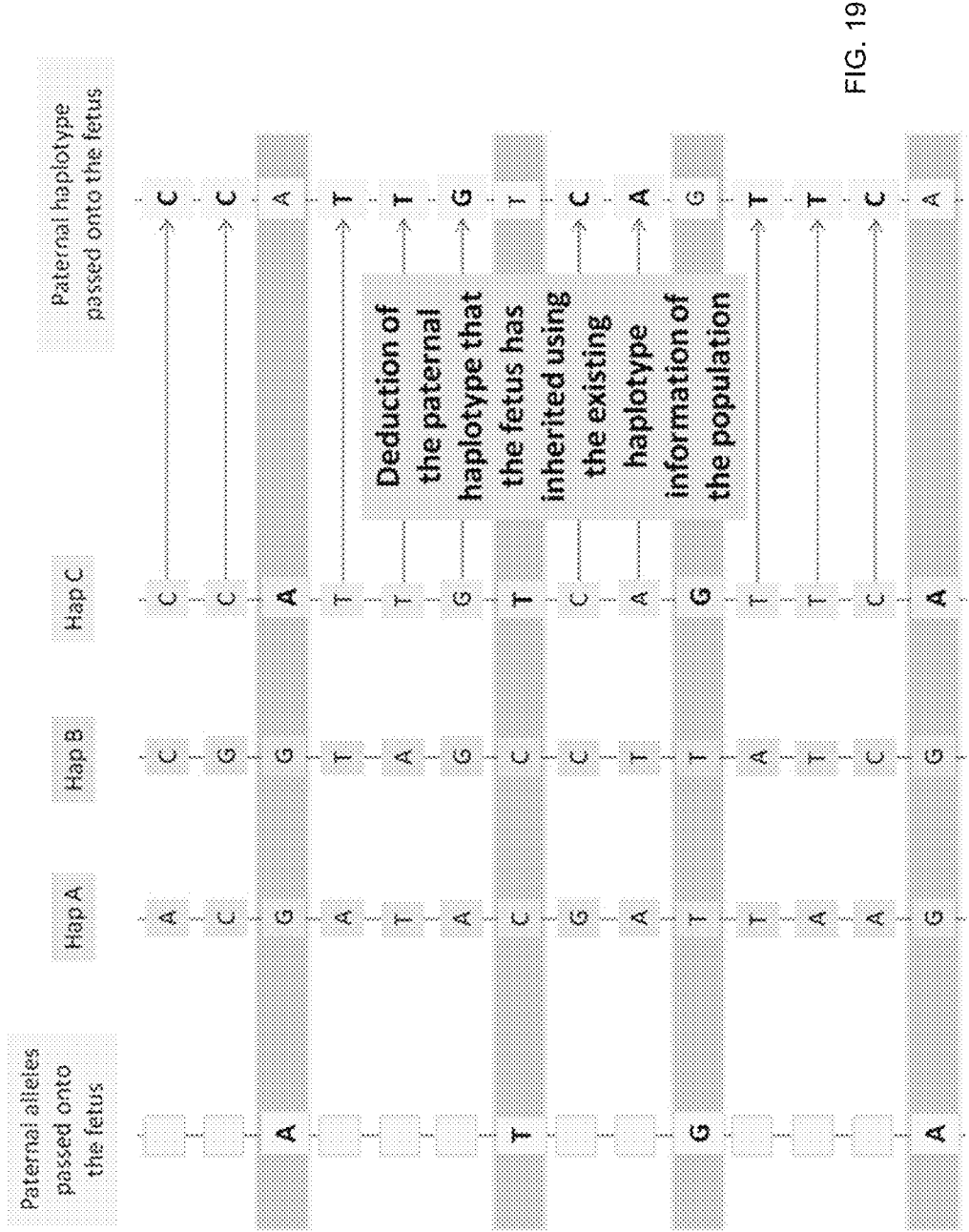
FIG. 19 shows the determination of the parental haplotype from the paternal alleles according to embodiments of the present invention. Hap A=SEQ ID NO:1; Hap B=SEQ ID NO:2; Hap c=SEQ ID NO:3.

In the example shown in FIG. 18, there are three possible haplotypes (Hap A, Hap B and Hap C) in the population. From the maternal plasma analysis, four SNPs have been identified as being homozygous for the mother and heterozygous for the fetus, thus representing the paternal alleles that the fetus inherits. The genotypes at these four SNPs fit the pattern of Hap C. Therefore, the fetus has inherited Hap C from the father, as shown in FIG. 19. In other words, for all the SNPs within the same haplotype block, the paternal alleles that the fetus has inherited can be deduced.

Figure 20:
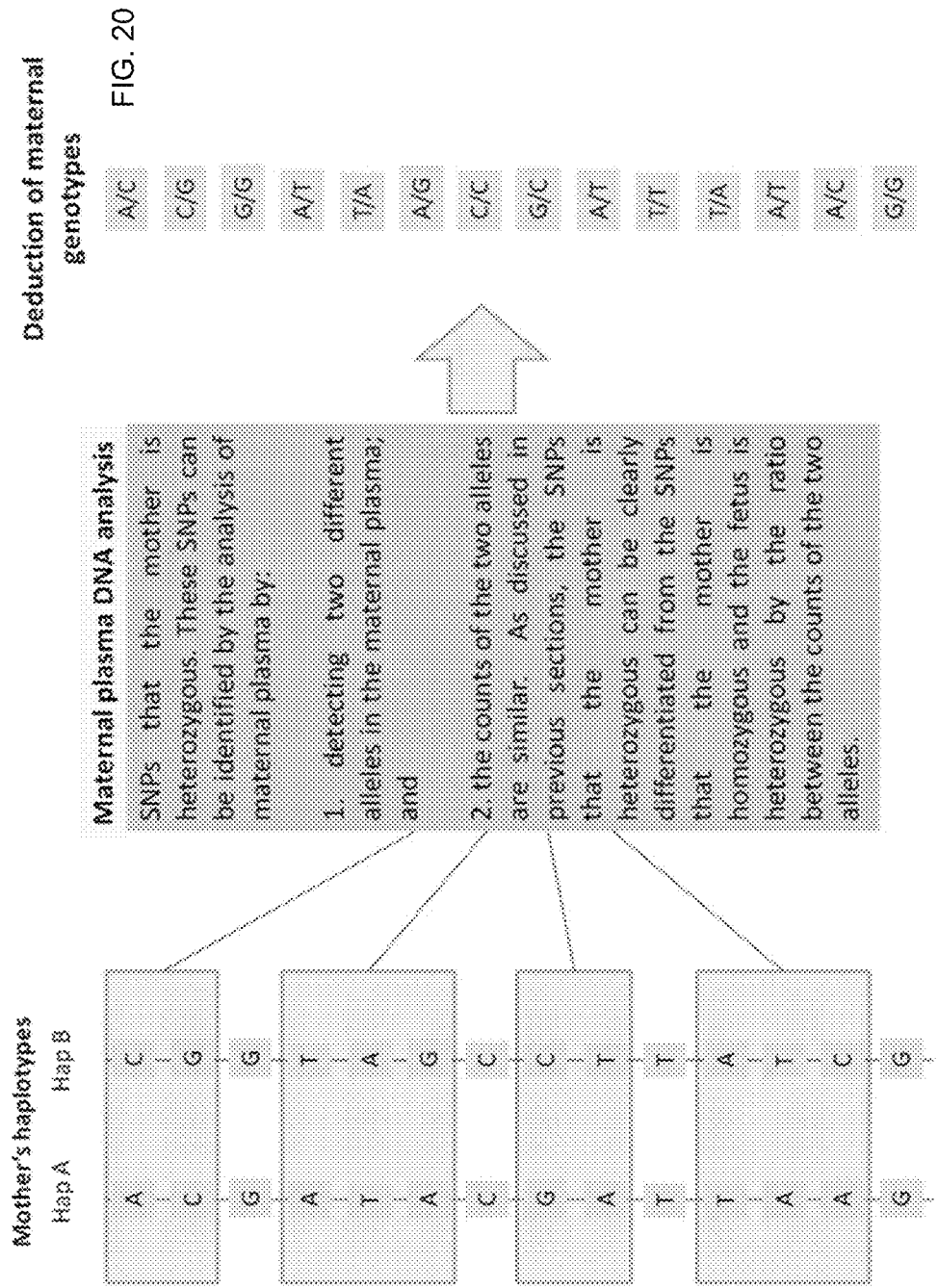
FIG. 20 shows the deduction of the maternal genotypes (SEQ ID NO:4) form the maternal sample analysis according to embodiments of the present invention. Hap A=SEQ ID NO:1; Hap B=SEQ ID NO:2.

In step 1640, loci (e.g. SNPs) at which the mother is heterozygous can be determined. In one embodiment, analysis of the maternal sample can provide SNPs that the mother is heterozygous. For example, at each of these SNPs, two different alleles can be detected in maternal plasma. In contrast to the SNPs that the mother is homozygous and the fetus is heterozygous which the fetal-specific allele only contributes a small proportion of the total alleles in maternal plasma, the counts of the two alleles would be similar for SNPs where the mother is heterozygous. Thus, the complete maternal genotype for all the SNP loci within the haplotype block could be determined from maternal plasma analysis, e.g., as shown in FIG. 20.

Figure 21:
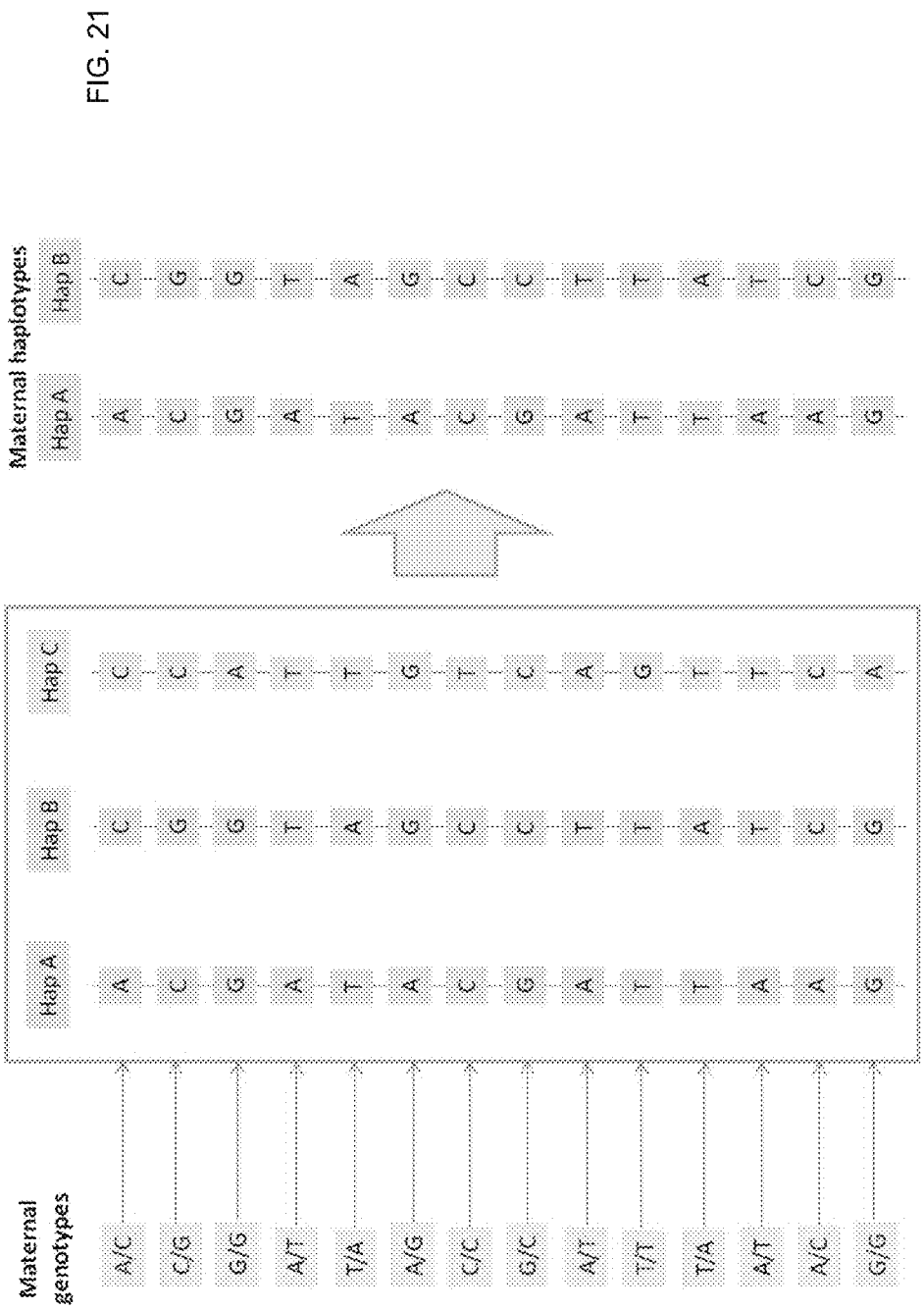
FIG. 21 shows an embodiment for determining the maternal haplotypes from the maternal genotypes and the reference haplotypes according to embodiments of the present invention. Hap A=SEQ ID NO:1; Hap B=SEQ ID NO:2; Hap c=SEQ ID NO:3; maternal genotypes=SEQ ID NO:4.
Figure 22:
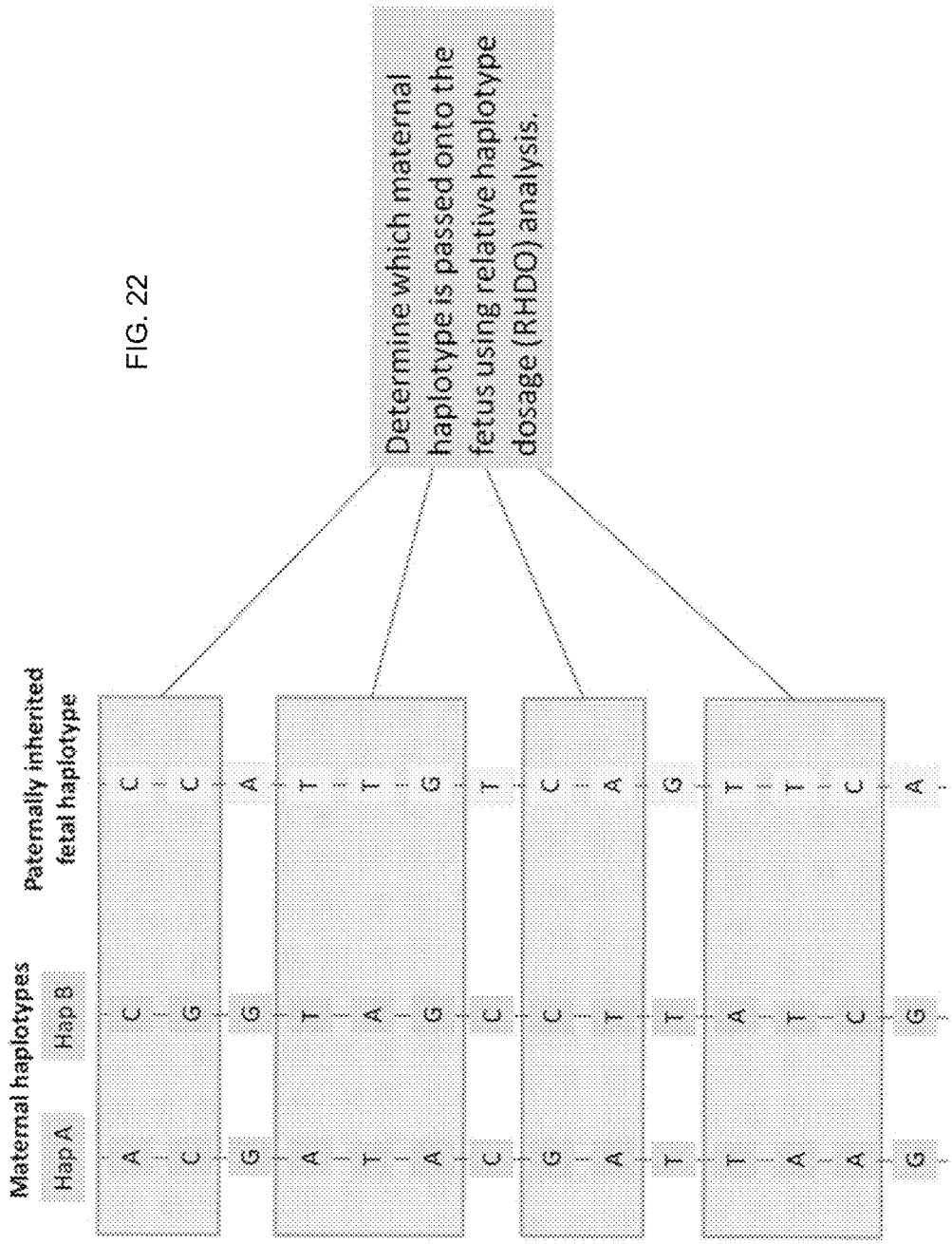
FIG. 22 shows the determined maternal haplotypes (Hap A=SEQ ID NO:1; Hap B=SEQ ID NO:2) and the paternally inherited haplotype (Hap C; SEQ ID NO:3) according to embodiments of the present invention.

In step 1650, the maternal haplotypes are deduced from the maternal genotypes from step 1640 by comparing the genotypes at the loci to the haplotype information of the relevant population. FIG. 21 shows an embodiment for determining the maternal haplotypes from the maternal genotypes and the reference haplotypes. In the example being used, the mother is homozygous for the G allele at the third SNP locus. As only Hap A and Hap B fulfill this criterion, this indicates the mother has one of the three haplotype combinations, namely Hap A/HapA, Hap A/Hap B or Hap B/HapB. In addition, as the mother is heterozygous for A and C for the first SNP, we can deduce the mother has the haplotype combination of Hap A/Hap B. In one embodiment, more than one possibility might result, and each possibility could be tested in the next step. From the above analyses, the haplotypes of the mother and the haplotype that the fetus inherits from the father have been determined. FIG. 22 shows the determined maternal haplotypes and the paternally inherited haplotype.

In step 1660, the maternal haplotype inherited by the fetus is determined from the maternal haplotypes identified in step 1650 and the paternally inherited haplotype identified in step 1630. Using this information, an embodiment can use RHDO analysis to determine which maternal haplotype is passed onto the fetus. An RHDO analysis can be performed according to any of the embodiment described herein.

Figure 23:
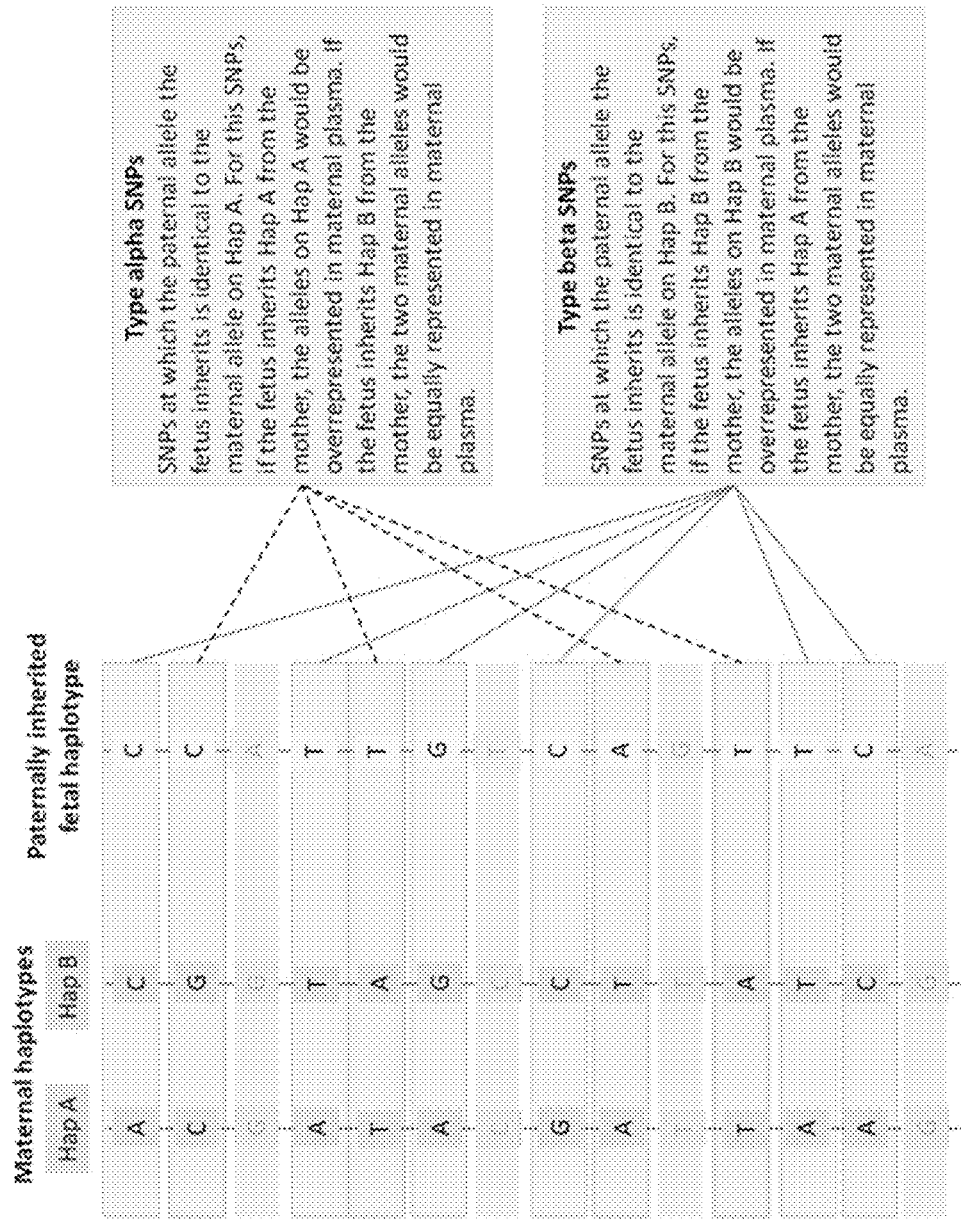
FIG. 23 shows the different types of loci (alpha (A) and beta (B)) for the maternal haplotypes (Hap A=SEQ ID NO:1; Hap B=SEQ ID NO:2) relative to the paternal haplotype (SEQ ID NO:3) according to embodiments of the present invention.

In one embodiment, for the RHDO analysis, the SNPs at which the mother is heterozygous can be divided into two types, namely type alpha and type beta (e.g. as shown in FIG. 23 and as described above). Type alpha SNPs refer to those loci where the paternal allele passed onto the fetus is identical to the maternal allele located on Hap A. For type alpha SNPs, if the fetus inherits Hap A from the mother, the allele on Hap A would be overrepresented in maternal plasma. On the other hand, if the fetus inherits Hap B from the mother, the two maternal alleles would be equally represented in maternal plasma.

Type beta SNPs refer to those loci where the paternal allele passed onto the fetus is identical to the maternal allele located on Hap B. For type beta SNPs, if the fetus inherits Hap B from the mother, the allele on Hap B would be overrepresented in maternal plasma. However, if the fetus inherits Hap A from the mother, the two maternal alleles would be equally represented in maternal plasma. The potential overrepresentation of Hap A or Hap B alleles can be determined using RHDO analysis.

In some embodiments, to apply RHDO analysis on a particular region without prior information of the maternal haplotypes and paternal genotypes, a relatively high-fold coverage of the SNPs within the haplotype block can be required, for example, 200 molecules corresponding to a SNP locus may need to be analyzed in one embodiment. This information can be obtained by, for example but not limited to, real-time PCR, digital PCR and massively parallel sequencing. In one embodiment, targeted sequencing (e.g., by a combination of target enrichment and massively parallel sequencing) can be used for obtaining representative and unbiased quantitative information of different alleles within the targeted region. An example below describes targeted sequencing. Therefore, this RHDO analysis can be applied to targeted sequencing data of maternal plasma DNA to determine which maternal alleles/haplotype are/is passed onto the fetus without prior information regarding the parental genotypes/haplotypes.

VII. DETECTION OF DE NOVO MUTATION

Some embodiments can detect a mutation that the fetus has acquired. A de novo mutation is a mutation that is not carried by the father or the mother, but is produced, for example, during gametogenesis from either the father or the mother or both. Such a detection has clinical utility because de novo mutations play a significant role in causing a number of genetic diseases e.g. hemophilia A and achondroplasia.

Figure 24:
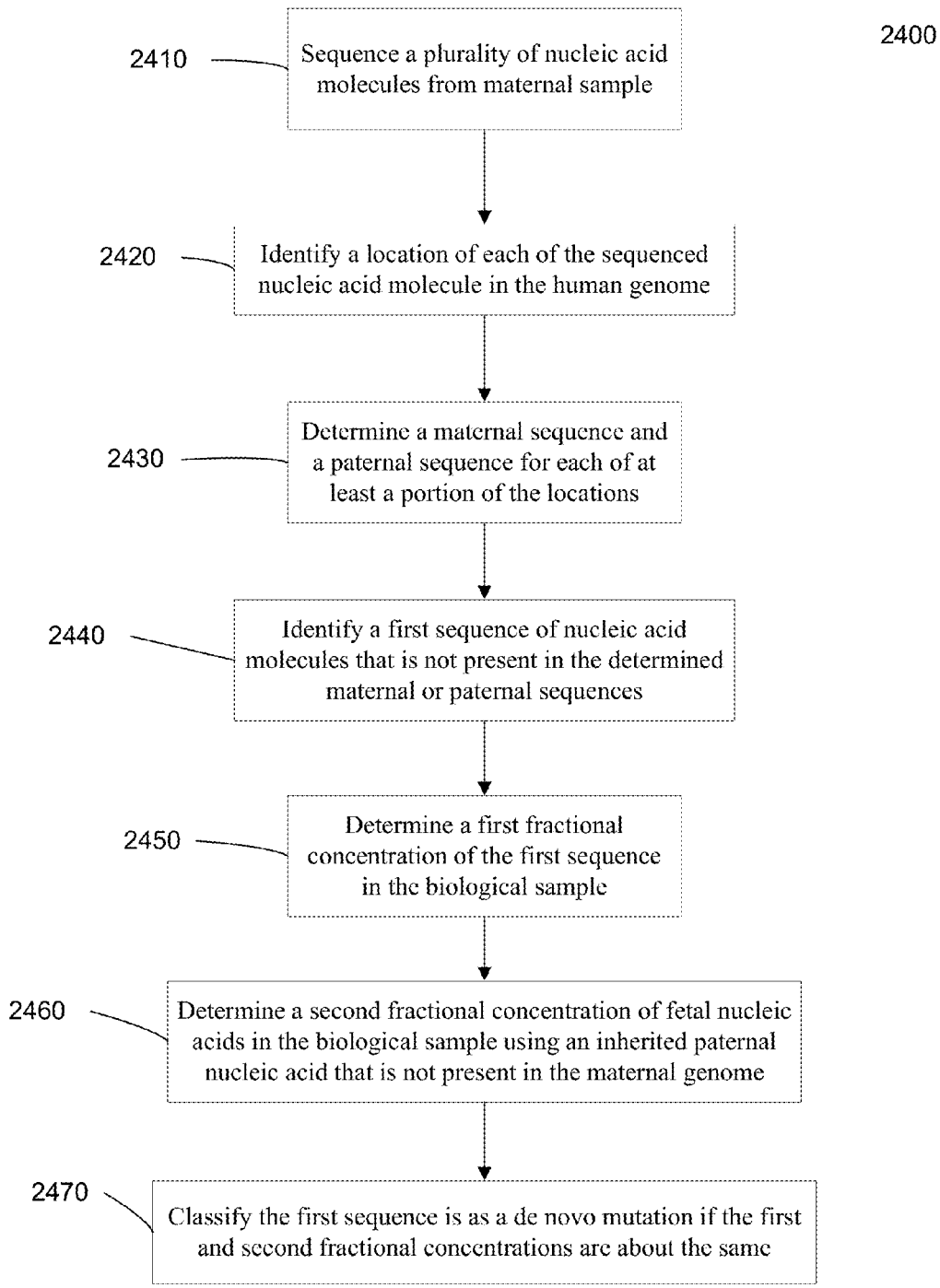
FIG. 24 is a flowchart illustrating a method 2400 of identifying a de novo mutation in the genome of an unborn fetus of a pregnant female.

FIG. 24 is a flowchart illustrating a method 2400 of identifying a de novo mutation in the genome of an unborn fetus of a pregnant female. The fetus having a father and a mother being the pregnant female, and the father having a paternal genome with two haplotypes and the mother having a maternal genome with two haplotypes, the method comprising:

In step 2410, a plurality of nucleic acid molecules from a biological sample obtained from the pregnant female are sequenced. Note the sample contains a mixture of maternal and fetal nucleic acids.

In step 2420, a location of each of the sequenced nucleic acid molecule in the human genome is identified. In one embodiment, the mapping of the sequences can be performed by single-ended or paired-end sequencing. In one aspect, a mapping to the human genome to find a location does not require an exact match of each of the nucleotides for a location to be found.

In step 2430, for each of at least a portion of the locations, a maternal sequence and a paternal sequence are determined at the location in question. For example, if 100 locations are determined in step 2420, then the maternal and paternal genomes at these 100 locations can be determined. In one embodiment, the paternal sequences are determined from a sample from the father as opposed to using reference haplotypes as is described above. Thus, a mutation not in a reference genome could still be detected. In various embodiments, the maternal sequences can be obtained from a sample that only includes maternal DNA, or can also be obtained from the biological sample, e.g., using methods described herein.

In step 2440, a first sequence in the plurality of nucleic acid molecules that is not present in the determined maternal or paternal sequences is identified. In one embodiment, a comparison of the first sequence to the determined maternal or paternal sequences requires an exact match. Thus, if the match is not exact, then the first sequence is considered to not be present in the determined maternal or paternal sequences. In this manner, even slight de novo mutations can be identified since a de novo mutation can be just a single nucleotide change.

In another embodiment, a certain number of DNA fragments showing the non-maternal and non-paternal sequence are required for the sequence to be deemed as a de novo mutation. For example, a cutoff of 3 DNA fragments could be used to determine whether a sequence, i.e. the de novo mutation, is present or not.

In step 2450, a first fractional concentration of the first sequence in the biological sample is determined. For example, the number of DNA fragments exhibiting the first sequence could be expressed as a proportion of all DNA fragments detected from that locus.

In step 2460, a second fractional concentration of fetal nucleic acids in the biological sample is determined using a nucleic acid molecule that the fetus has inherited from its father, and which is present in the paternal genome, but which is not present in the maternal genome. Such a nucleic acid molecule might contain a first allele at a location where the father is homozygous and the mother is also homozygous, but for a different allele, and thus the fetus is an obligate heterozygote. Informative loci as described above can be used to determine the nucleic acid molecule to use to determine the second fractional concentration.

In other embodiments, the second fractional concentration can be determined using other approaches, such as the use of PCR assays, digital PCR assays or assays based on mass spectrometry, on the Y chromosome, a panel of genetic polymorphisms, i.e. single nucleotide polymorphisms, or insertion-deletion polymorphisms (Lun F M F et al Clin Chem 2008; 54: 1664-1672). Another alternative is to use one or more genomic loci which exhibit different DNA methylation between the fetus and mother (Poon L L M et al. Clin Chem 2002; 48: 35-41; Chan K C A et al. Clin Chem 2006; 52: 2211-2218; U.S. Pat. No. 6,927,028).

In one embodiment, the different epigenetic status is reflected by different DNA methylation patterns. The different DNA methylation patterns can involve the RAS association domain family 1A (RASSF 1A) or the holocarboxylase synthetase (biotin-(proprionyl-Coenzyme A-carboxylase (ATP-hydrolysing)) ligase (HLCS) gene. The amount of DNA fragments with the fetal-specific DNA methylation profile can be expressed as a proportion of all DNA fragments originating from the differentially methylated locus.

In step 2470, the first sequence is classified as a de novo mutation if the first and second fractional concentrations are about the same. A non-maternal and non-paternal sequence originating from errors in the analysis process, e.g. sequencing errors, is a random event and has a low probability of recurrence. Therefore, multiple DNA fragments exhibiting the same non-maternal and non-paternal sequence at amounts similar to the measured fractional fetal DNA concentration for the sample are likely to be a de novo mutation present in the fetal genome rather than have arisen from sequencing error. In one embodiment, a cutoff value may be used to determine whether the fractional concentrations are the same. For example, if the concentrations are within a specified value of each other, then the first sequence is classified as a de novo mutation. In various embodiments, the specified value can be 5%, 10%, or 15%.

EXAMPLES

I. Example 1

To illustrate embodiments of the present invention, the following case was analyzed. A couple, attending an obstetrics clinic for the prenatal diagnosis of beta-thalassemia, was recruited. The father was a carrier of the -CTTT 4 base-pairs deletion of codons 41/42 of the human beta-globin gene. The pregnant mother was a carrier of the A→G mutation at nucleotide −28 of the human beta-globin gene. Blood samples were taken from the father and mother. For the mother, the blood sample was taken prior to chorionic villus sampling (CVS) at 12 weeks of gestation. Following CVS, a portion was stored for the experiment. An objective of the experiment was to construct a genomewide genetic map or to determine the partial or complete genomic sequence of the fetus by the massively parallel sequencing of maternal plasma DNA.

1. Determination of the Parental Genotypes

DNA was extracted from the buffy coats of the father and mother, and the CVS sample. These DNA samples were subjected to analysis by the Affymetrix Genome-Wide Human SNP Array 6.0 system. This system features 1.8 million genetic markers, including ~900,000 single nucleotide polymorphisms (SNPs) and more than 950,000 probes for the detection of copy number variations. The absolute number and the percentages of SNPs showing different genotype combinations for the father, mother and fetus (CVS) are shown in the table of FIG. 25A.

Even though the Affymetrix system was used in this example, in practice, any genotyping platform known to those of skill in the art could be used. Indeed, apart from genotyping, the buffy coat DNA of the father and mother can also be subjected to sequencing, either on a whole genome basis or for selected genomic regions. Furthermore, any source of constitutional DNA (e.g. buccal cell DNA, hair follicle DNA, etc) from the father and mother could be used establishing the parental genotypes.

The CVS sample was analyzed to provide a standard for comparison with the fetal genetic map deduced from maternal plasma analysis. In addition, for this experiment, the genotype of the CVS sample can also be used for constructing the haplotype of the mother for RHDO analysis. In this scenario, the use of the CVS genotype for such haplotype construction purpose was only used for illustration purposes. In a clinical application of embodiments, the maternal haplotype can be constructed through the analysis of other individuals in the family, for example, a previous offspring, a sibling, the parents or other relatives of the mother. The maternal haplotypes of the chromosomal regions of interest can also be constructed by other methods well known to those skilled in the art, some of which are mentioned herein.

For selected embodiments, the haplotype of the father of the unborn fetus to be analyzed could also be determined. This information can be particularly useful for relative haplotype dosage for chromosomal regions in which both the father and the mother are heterozygous.

2. Massively Parallel Sequencing of Maternal Plasma DNA

Plasma DNA obtained from the mother was subjected to massively parallel sequencing using the Illumina Genome Analyzer platform. Paired-end sequencing of the plasma DNA molecules was performed. Each molecule was sequenced at each end for 50 bp, thus totaling 100 bp per molecule. The two ends of each sequence were aligned to the repeat-unmasked human genome (Hg18 NCBI.36 downloaded from UCSC http://genome.ucsc.edu) using the SOAP2 program from the Beijing Genomics Institute at Shenzhen (soap.genomics.org.cn) (Li R et al. Bioinformatics 2009, 25 (15):1966-7) The table, FIG. 25B, lists the alignment statistics of the first 20 flow cells. Thus, with 20 flow cells, over 3.932 billion reads were aligned to the reference human genome.

3. Calculation of the Fractional Fetal DNA Concentrations

As mentioned above, the fractional concentration of fetal DNA in the maternal plasma sample can be calculated from the sequencing data. One way was to analyze SNPs in which the father and mother were both homozygous, but for different alleles from one another. For such SNPs, the fetus would be an obligate heterozygote for one paternally-inherited and one maternally-inherited allele. In one embodiment, any of the calculation methods described in section V may be used. In this example, calculations were performed on the cumulative data across different polymorphic genetic loci that fulfilled the parental genotype configuration (i.e. both parents being homozygous, but for different alleles) on different chromosomes. The fractional concentrations of fetal DNA calculated for SNPs located on different chromosomes are listed in the right-hand-most column of FIG. 26. As can be seen from the table, the fractional concentrations determined for SNPs located on different chromosomes correlate very closely with each other.

As a quality control experiment, SNPs in which the mother was homozygous and the father was heterozygous were also investigated from the Affymetrix SNP 6.0 analysis of the buffy coat samples (middle column of FIG. 26). It can be seen that at sufficient depth of DNA sequencing, the fractional fetal DNA concentrations measured from this analysis were very similar to those measured for SNPs in which both the father and mother were homozygous but for different alleles.

In one implementation, when near-concordance of the fractional fetal DNA concentrations was observed from these two types of SNPs, one could conclude that one was close to complete sequencing coverage of the fetal genome. In one aspect, at a lesser depth of coverage, the fractional fetal DNA concentrations measured for SNPs in which the mother was homozygous and the father was heterozygous would be higher than those measured for SNPs in which both the father and mother were homozygous, but for different alleles. At such a lesser depth of coverage, the absence of a paternally-unique allele from the sequencing results can have two possible causes: (i) that the fetus had not inherited this allele from the father; and/or (ii) that the fetus had inherited this allele from the father, but then this allele was missing from the sequencing results because the depth of sequencing was not enough.

4a. Calculation of the Percentage Coverage of the Fetal Genome

Also, as mentioned above, the percentage of the fetal genome that had been analyzed by sequencing of maternal plasma DNA could be determined by looking at the subset of SNPs in which the father and mother were both homozygous, but for different alleles. In this family, 45,900 SNPs on the Affymetrix SNP 6.0 array belonged to this subset. The percentage coverage of the fetal genome could be deduced by analyzing the plasma DNA sequencing data to see in what percentage of this subset of SNPs could a fetal allele be detected by sequencing.

The plot in FIG. 27A illustrates the observed percentage of SNPs in this subset in which a fetal allele could be seen from the sequencing data for the first 20 flow cells analyzed. Thus, a fetal allele could be observed in 94% of such SNPs. This degree of sequencing corresponded to over 3.932 billion reads, each with 100 bp of sequences. The plot in FIG. 27B shows the coverage vs. the number of reads, instead of the number of flow cells. With the increase in throughput of different sequencing platforms, it is expected that the number of flow cells or runs that would be used or required to generate these number of sequence reads or length of sequences would decrease in the future.

In some embodiments, as multiple SNPs were detected in each chromosomal region or chromosomes, the coverage of the fetal genome could be much lower than 94% while still providing an accurate genome mapping. For example, assume there are 30 informative SNPs in a chromosomal region, but a fetal allele is detected for only 20 SNPs out of the 30 SNPs. However, the chromosomal region may still be accurately identified with the 20 SNPs. Thus, in one embodiment, equivalent accuracy can be obtained with a coverage of less than 94%.

4b. Coverage of Genetic Map of Alleles that the Fetus Had Inherited from its Father This illustrative analysis focuses on SNP alleles in which the father was heterozygous and the mother was homozygous. In this family, 131,037 SNPs on the Affymetrix SNP 6.0 platform belonged to this category. A subset of these SNPs consisted of the 65,875 SNPs in which the mother was homozygous, while the father and the fetus were both heterozygous. With the use of 20 flow cells, the paternally-inherited alleles could be observed in 61,875 of these SNPs, indicating a coverage of 93.9%. This latter percentage fitted well with the percentage coverage data deduced in the previous paragraph. The correlation between the coverage of paternally-inherited alleles and the number of mappable sequence reads and the number of flow cells sequences are shown in FIG. 28A and FIG. 28B, respectively.

To elucidate the specificity of this approach for detecting genuine paternally-inherited fetal alleles, the 65,162 (i.e. 131,037-65,875) SNPs in which the fetus had inherited alleles that were the same as those possessed by the mother were analyzed. For such SNPs, the apparent detection of alleles different from those possessed by the mother would represent a false-positive. Thus, amongst the 65,162 SNPs, only 3,225 false-positives (4.95%) were observed when 20 flow cells were analyzed. These false-positives can be the result of sequencing errors or genotyping errors of the father's or mother's DNA, or de novo mutations in the fetus. The correlation between the false-positive rate and the number of flow cells sequenced is shown in FIG. 29A.

The false-positive rates can also be estimated by considering the subset of SNPs which both the father and mother were homozygous and with the same allele. The presence of any alternative allele at the particular locus was considered to be a false-positive. These false-positives can be the result of sequencing errors or genotyping errors of the father's or mother's DNA, or de novo mutations in the fetus. There were 500,673 SNPs in this subset. With the sequence data from 20 flow cells, false-positive results were detected in 48,396 SNPs (9.67%). The correlation between false-positive rate and the number of flow cells sequenced is shown in FIG. 29B. This false-positive rate was higher than the estimation using the subset of SNPs which the mother and the fetus were homozygous and the father was heterozygous. This is because, in the latter subset of SNPs, only the presence of the paternally inherited allele in maternal plasma is considered to be a false-positive whereas, in the former subset, any allele other than the common allele shared by the father and mother is considered as a false-positive result.

FIG. 30 shows the coverage of the fetal-specific SNPs for different number of flow cells analyzed. The SNPs that both the father and mother were homozygous, but with different alleles, are included in this analysis. The X-axis is the fold coverage of the fetal-specific SNPs, and the Y-axis is the percentage of SNPs with the specified fold coverage. With the increase in the number of flow cells being analyzed, the average number of fold coverage for the fetal-specific SNPs increases. For example, when one flow cell was analyzed, the average coverage of SNPs was 0.23 fold. The average coverage increased to 4.52 fold when 20 flow cells were analyzed.

5. Accuracy of a Genetic Map Inherited from its Mother

FIG. 31 shows the accuracy of Type A analysis when data from 10 flow cells were used. Section II.B describes embodiments of a Type A and Type B analysis (also referred to as alpha and beta). The accuracy is for the correct determination of the haplotype that was inherited from the mother. The accuracy is separately presented for each chromosome.

Using a likelihood ratio of 1,200 for SPRT analysis (Zhou W et al. Nat Biotechnol 2001; 19:78-81; Karoui N E et al. Statist Med 2006; 25:3124-33), the accuracy ranged from 96% to 100%. As shown, even with such a high likelihood ratio for SPRT classification, a total of 2,760 segments across the genome could be classified. This degree of resolution is sufficient for most purposes, when one considers that meiotic recombinations take place at the frequency of one to a low single digit number per chromosome arm per generation. In addition, one could see that all of the misclassifications could be prevented when the interlacing approach was used (right-hand-side of FIG. 31). As described above, the interlacing approach uses both Type A and Type B analysis.

FIG. 32 shows the accuracy of Type B analysis when data from 10 flow cells were used. Using a likelihood ratio of 1,200 for SPRT analysis, the accuracy ranged from 94.1% to 100%. All of the misclassifications could be prevented when the interlacing approach was used (right-hand-side of FIG. 32), as was seen in FIG. 31.

FIG. 33 shows the accuracy of Type A analysis when the data from 20 flow cells were used. Using a likelihood ratio of 1,200 for SPRT analysis and the "two consecutive blocks" algorithm, a total of 3,780 classifications were made and only 3 (0.1%) classifications were incorrect. FIG. 34 shows the accuracy of Type B analysis when the data from 20 flow cells were used. Using a likelihood ratio of 1,200 for SPRT analysis and the "two consecutive blocks" algorithm, a total of 3,355 classifications were made and only 6 (0.2%) classifications were incorrect. In these examples, the SPRT is performed across a number of genetic markers, such as SNPs.

II. Prenatal Determination of Risk of Beta-Thalassemia

In one embodiment, to determine the risk of the fetus in having beta-thalassemia (an autosomal recessive disease) one can determine if the fetus has inherited mutant alleles carried by its father and mother. In this case mentioned above, the father is a carrier of the -CTTT 4 base-pairs deletion of codons 41/42 of the human beta-globin gene. The pregnant mother was a carrier of the A→G mutation at nucleotide −28 of the human beta-globin gene.

To determine if the fetus has inherited the paternal codons 41/42 mutation, the sequencing data of the maternal plasma DNA, using the first 10 flow cells, were searched for this mutation. A total of 10 reads with this mutation were found (FIG. 35A). Hence, the fetus had inherited the paternal mutation. In addition, 62 reads were found to contain the wildtype sequence at codons 41/42 (FIG. 35B). Thus, the percentage of the reads in this region containing the mutation is 0.1389. This figure is very close to the fractional fetal DNA concentration determined in FIG. 26. In one embodiment, the risk of the fetus in inheriting the paternal mutation can also be determined by elucidating its inheritance of genetic polymorphisms linked to the paternal mutation.

In one embodiment, to determine the risk that the fetus has inherited the maternal −28 mutation, RHDO analysis was performed. In this family, the −28 mutation was located on haplotype IV while the wildtype allele was located on haplotype III. The results of the Type A RHDO analysis are shown in FIG. 36 while those of the Type B RHDO analysis are shown in FIG. 37. In both types of analysis, the fetal inheritance of haplotype III from the mother was deduced. In other words, the fetus had inherited the wildtype allele from the mother. The final diagnosis of the fetus was that it has inherited the codons 41/42 mutation from the father and a wildtype allele from the mother. Thus, the fetus is a heterozygous carrier of beta-thalassemia and thus should be clinically healthy.

III. Target-Enrichment and Targeted Sequencing

As discussed in the previous sections, the accuracy of the estimation of the fractional fetal DNA concentration and the resolution of the genetic map deduced from the analysis of maternal plasma DNA can depend on the depth of coverage of the loci-of-interest. For example, we have demonstrated that a total of 200 molecules corresponding to a SNP locus might be required to determine, with high accuracy, the fractional fetal DNA concentration without prior information of the maternal genotype. The allele counts for a SNP in maternal plasma can be obtained by, for example but not limited to, real-time PCR, digital PCR and massively parallel sequencing.

As massively parallel sequencing of maternal plasma DNA can simultaneously determine the allele counts for millions of SNPs across the whole genome, it is an ideal platform for genomewide analysis across different loci. The basic format of massively parallel sequencing allows different regions within the genome to be covered at similar depths. However, in order to sequence a particular region-of-interest at high sequencing depth using random massively parallel sequencing, the remaining parts of the genome (not intended to be analyzed) has to be sequenced to the same extent. Thus, this approach could be costly. To improve the cost-effectiveness of the massively parallel sequencing approach, one way is to enrich the target region before proceeding to sequencing. Targeted sequencing can be performed by solution phase capture (Gnirke A, et al. Solution hybrid selection with ultra-long oligonucleotides for massively parallel targeted sequencing. Nat Biotechnol 2009; 27:182-9), microarray capture (e.g. using the NimbleGen platform) or targeted amplification (Tewhey R, et al. Microdroplet-based PCR enrichment for large-scale targeted sequencing. Nat Biotechnol 2009; 27:1025-31).

Targeted sequencing was initially applied to detect population genetic variations, e.g. for genetic association studies. Therefore, its current application in genomics research is aimed at solving qualitative problems (e.g. genotyping or mutation detection). However, the application of targeted sequencing in maternal plasma DNA for noninvasive prenatal diagnosis purpose involves quantitative considerations, the feasibility of which had been unclear. For example, the use of targeted sequencing might introduce quantitative bias in the detection of fetal and maternal DNA in maternal plasma. In addition, previous work has shown that fetal DNA is shorter than maternal DNA (Chan K C A et al. Size distributions of maternal and fetal DNA in maternal plasma. Clin Chem 2004; 50: 88-92). This size difference might also introduce quantitative bias or differential efficiency in the capture of fetal and maternal DNA in maternal plasma. One was also not sure about the efficiency whereby such fragmented DNA molecules might be captured. In the following descriptions, we demonstrate that targeted sequencing can be achieved by target enrichment followed by massively parallel sequencing. We also show that target enrichment is an efficient way of estimating the fractional fetal DNA concentration compared with whole-genome sequencing.

A. Determining Fractional Concentration Using Target-Enrichment

1. Materials and Methods

Four (M6011, M6028, M6029 and M6043) pregnant women with singleton female fetuses were recruited. Maternal peripheral blood samples were collected into EDTA blood tubes before elective cesarean section in the third trimester, while placenta samples were collected after elective cesarean section. After centrifugation, DNA from the peripheral blood cells was extracted using the Blood Mini Kit (Qiagen). DNA from 2.4 mL of plasma was extracted by the DSP DNA Blood Mini Kit (Qiagen). Maternal genomic DNA was extracted from buffy coat and fetal genomic DNA was extracted from placental tissues. Third trimester samples were used in this example for illustration purposes only. First and second trimester samples can equally be used.

Maternal and fetal genotypes were determined by the Genome-Wide Human SNP Array 6.0 (Affymetrix). 5~30 ng plasma DNA for each case was used for DNA library construction by the paired-end sample preparation kit (Illumina) according to the manufacturer's protocol of Chromatin Immunoprecipitation Sequencing sample preparation. The adapter-ligated DNA was purified directly using spin columns provided in a QIAquick PCR purification kit (Qiagen), without further size selection. The adapter-ligated DNA was then amplified using a 15-cycle PCR with standard primers. The primers were PCR Primer PE 1.0 and 2.0 from Illumina. The DNA libraries were quantified by using a NanoDrop ND-1000 spectrophotometer (NanoDrop Technologies) and run on a 2100 Bioanalyzer, using a DNA 1000 kit (Agilent), to check for size distribution. 0.6~1 µg of an amplified plasma DNA library was generated for each sample in an average size of about 290 bp. The capture library was obtained from Agilent and covered 85% of the exons on the human chrX (catalog number: 5190-1993). For all four cases in this study, 500 ng of the amplified plasma DNA library of each case was incubated with the capture probes for 24 hours at 65° C., according to the manufacturer's instruction. After hybridization, the captured targets were selected by pulling down the biotinylated probe/target hybrids by using streptavidin-coated magnetic beads (Dynal DynaMag-2 Invitrogen), and purified with the MinElute PCR Purification Kit (Qiagen). Finally, the targeted DNA libraries were enriched by 12-cycle PCR amplification with SureSelect GA PE primers from Agilent. The PCR products were purified by QIAquick PCR Purification Kit (Qiagen). The DNA libraries prepared with or without target enrichment were then subjected to random massively parallel sequencing using the Illumina Genome Analyzer IIx. One sequencing lane on a standard flow cell was used to sequence each DNA library.

2. Fractional Concentration of Fetal DNA without Target Enrichment

The fractional fetal DNA concentration can be calculated based on the allele counts of the informative SNPs (i.e. SNPs that the mother is homozygous and the fetus is heterozygous). The table below shows that 120184, 110730, 107362 and 110321 informative SNPs were identified throughout the whole genome for the four cases, while 63, 61, 69 and 65 (respectively in the same case order) fell within the targeted region on chromosome X. Without target enrichment, the fractional fetal DNA concentrations were 33.4%, 31.3%, 29.2% and 34.4% based on the data of all informative SNPs in the genome.

| Sample | Target enrichment | Whole genome informative SNP no. | Shared allele counts | Fetal specific allele counts | Fractional fetal DNA concentration |
|---|---|---|---|---|---|
| M6011 | No | 120,184 | 15,309 | 3,064 | 33.4% |
| M6028 | No | 110,730 | 16,778 | 3,114 | 31.3% |
| M6029 | No | 107,362 | 19,889 | 3,404 | 29.2% |
| M6043 | No | 110,321 | 21,070 | 4,369 | 34.4% |

3. Comparison of Samples with and without Target Enrichment

In some embodiments, the depth of sequence coverage represented the average number of times each base had been sequenced in a particular region. In this embodiment, we calculated the sequence depth of the targeted region by dividing the total number of sequenced bases within the targeted region by the targeted region length (3.05 Mb). For the regions covered by the enrichment kit, the mean sequence coverage was 0.19 times for the non-enriched samples and 54.9 times for the enriched samples, indicating a mean of 289-fold enrichment. At this sequencing depth, only 4.0% of the fetal-specific alleles within the targeted region were detected before target enrichment (see table below). In comparison, 95.8% of them became detectable after target enrichment (see table below). Therefore, target enrichment greatly increased the detection rate of fetal specific alleles within the targeted region.

Then, we compared the fractional fetal DNA concentrations based on the read counts of all informative SNPs within the targeted region for each sample, with and without enrichment. Without target enrichment, the number of fetal-specific reads ranged from 0 to 6 for the four samples (see table below). Due to the low sequence coverage, inadequate sampling of the fetal DNA molecules would prevent an accurate estimation of the fractional fetal DNA concentration. With target enrichment, a much larger number of fetal specific allele counts (511~776) and shared allele counts (2570~3922) within the targeted region were observed (see table below). The fetal DNA percentages were calculated as 35.4%, 33.2%, 26.1% and 33.0%, consistent with the fetal DNA percentages estimated by the genomewide data in the non-enriched samples (see table below). These results indicated that maternal and fetal DNA molecules were enriched to a similar extent within the targeted region.

extracted from the chorionic villi. The samples were prepared and analyzed as described above. Each sample was then sequenced randomly using one lane on an Illumina flow cell.

In this example, we used the fetal genotype, along with sequencing information from nucleic acids of the mother, to deduce the maternal haplotypes for chromosome X and deduce which haplotype was inherited from the mother. For each SNP on chromosome X that the mother was heterozygous (i.e., an informative SNP), the allele that was inherited by the fetus is defined as coming from the maternal haplotype 1 (Hap I) whereas the maternal allele that was not passed onto the fetus was defined as coming from the maternal haplotype 2 (Hap II). In some embodiments, for clinical applications, the fetal genotype may not be available beforehand and the maternal haplotypes can be determined or inferred by methods well-known to those skilled in the art and methods described herein. Chromosome X is used here for illustration purposes only. Other chromosomes, e.g. the autosomes, can also be used in such analysis.

For the five cases described here, all of them were carrying a singleton male fetus. As a male fetus only inherits one chromosome X from the mother but no chromosome X from the father, the maternal chromosome X that was passed

| Sample | Target enrichment | No. of informative SNP within the targeted region | No. of detectable fetal specific alleles | Fetal specific allele detection rate | Shared allele counts | Fetal specific allele counts | Fractional fetal DNA concentration |
|---|---|---|---|---|---|---|---|
| M6011 | No | 63 | 6 | 9.5% | 13 | 6 | 63.2% |
| M6028 | No | 61 | 2 | 3.3% | 6 | 2 | 50.0% |
| M6029 | No | 69 | 2 | 2.9% | 11 | 2 | 30.8% |
| M6043 | No | 65 | 0 | 0.0% | 15 | 0 | 0.0% |
| M6011 | Yes | 63 | 60 | 95.2% | 3072 | 661 | 35.4% |
| M6028 | Yes | 61 | 60 | 98.4% | 2570 | 511 | 33.2% |
| M6029 | Yes | 69 | 66 | 95.7% | 3835 | 575 | 26.1% |
| M6034 | Yes | 65 | 61 | 93.9% | 3922 | 776 | 33.0% |

B. Determining Fetal Genome Using Target-Enrichment

One application of an RHDO method is for the noninvasive prenatal detection of maternally inherited genetic diseases. Using massively parallel sequencing of maternal plasma without target enrichment, RHDO analysis can accurately determine which maternal haplotype is passed onto the fetus with an average of 17 SNPs when the sequencing depth of maternal plasma DNA is approximately 65-fold human genome coverage. To improve the cost-effectiveness of this approach, selectively directing the sequencing to specific regions of interest within the genome and to then applying an RHDO analysis to the sequencing data can be performed. As an example, we demonstrated the concept using the targeted sequencing and RHDO analysis of chromosome X. However, the targeted sequencing and RHDO analysis can also be applied to all chromosomes, e.g. the autosomes. In one embodiment, an RHDO analysis as described above can be used for the targeted embodiments.

Five (PW226, PW263, PW316, PW370 and PW421) pregnant women with singleton male fetuses were recruited. Maternal peripheral blood samples were collected into EDTA blood tubes before chorionic villus sampling in the first trimester. After centrifugation, DNA from the peripheral blood cells was extracted using the Blood Mini Kit (Qiagen). DNA from 3.2 mL of plasma was extracted by the DSP DNA Blood Mini Kit (Qiagen). Maternal genomic DNA was extracted from the buffy coat and fetal genomic DNA was onto the fetus would be overrepresented in the maternal plasma. The RHDO analysis was carried out from the pter to qter of chromosome X. Starting with the SNP closest to the pter of chromosome X, SPRT analysis can determine if the allele on Hap I or Hap II was statistically significantly overrepresented in the maternal plasma. If none of the two haplotypes was statistically significantly overrepresented, the allelic counts for the next SNP can be combined for further SPRT analysis. Additional SNPs can be combined for analysis until the SPRT process identified one of the haplotypes as statistically significantly overrepresented. The classification process can then be restarted at the next SNP.

FIGS. 38A and 38B shows the SPRT classification results for case PW226 as an example. There were a total of nine successful SPRT classifications for chromosome X in this case. For each SPRT classification, the alleles on Hap I was shown to be overrepresented in the maternal plasma sample, indicating that the fetus had inherited Hap I from the mother. As we defined Hap I to be the haplotype containing the alleles passed onto the fetus, the results of all these SPRT classification were correct.

The RHDO analysis results for the five cases are summarized in FIG. 39. The number of successful SPRT classifications ranged from 1 to 9. All of the SPRT classifications were correct. A higher fractional fetal DNA concentration was associated with a higher number of classifications. This is because the allelic imbalance due to the presence of fetal DNA can be detected more easily when the fractional concentration of fetal DNA is higher. Therefore, fewer SNPs may be needed to reach a successful RHDO classification. Defined chromosomal region(s) can thus be divided into more RHDO blocks. Our results confirm that RHDO analysis can be performed on the massively sequencing data which are obtained after target enrichment.

Our data further showed that the targeted approach is a more cost-effective way of performing RHDO analysis. Without target enrichment, for samples with similar fetal DNA concentrations, sequencing by approximately 5 flow cells (i.e. 40 sequencing lanes) was required (FIG. 40) to reach the average depth achieved for samples shown in FIG. 39. Here we show that with target enrichment, sequencing by only one lane already reaches the average sequencing depth of some 15 to 19 fold for successful RHDO classification. Alternatively, even higher fold-level of sequencing coverage could be achieved with relatively little additional cost when target enrichment is used. The higher level of sequencing coverage can effectively reduce the size of the genomic region required for successful RHDO classification and hence improves the resolution of the analysis.

IV. Target-Enrichment

It has been known since 2004 that circulating fetal DNA molecules are generally shorter than maternal DNA in maternal plasma (Chan K C A et al Clin Chem 2004; 50: 88-92; Li et al Clin Chem 2004). However, the molecular basis of this observation remained unsolved. In our current study, we generated $3.931 \times 10^9$ reads in the study plasma sample and used 1-bp bins in our bioinformatics analysis. The size of each sequenced plasma DNA molecule were deduced from the genome coordinates of the ends of the paired-end reads.

For this analysis, we focused on single nucleotide polymorphisms (SNPs) in which the father and mother were both homozygous, but for a different allele. For such SNPs, the fetus was an obligate heterozygote. The allele for each SNP that the fetus had inherited from the father could be used as a fetal-specific marker. The sizes of the fetal (using the paternally-inherited fetal-specific alleles) and total sequences were determined for the whole genome (FIG. 41) and individually for each chromosome (FIG. 42A-42C).

Figure 41:
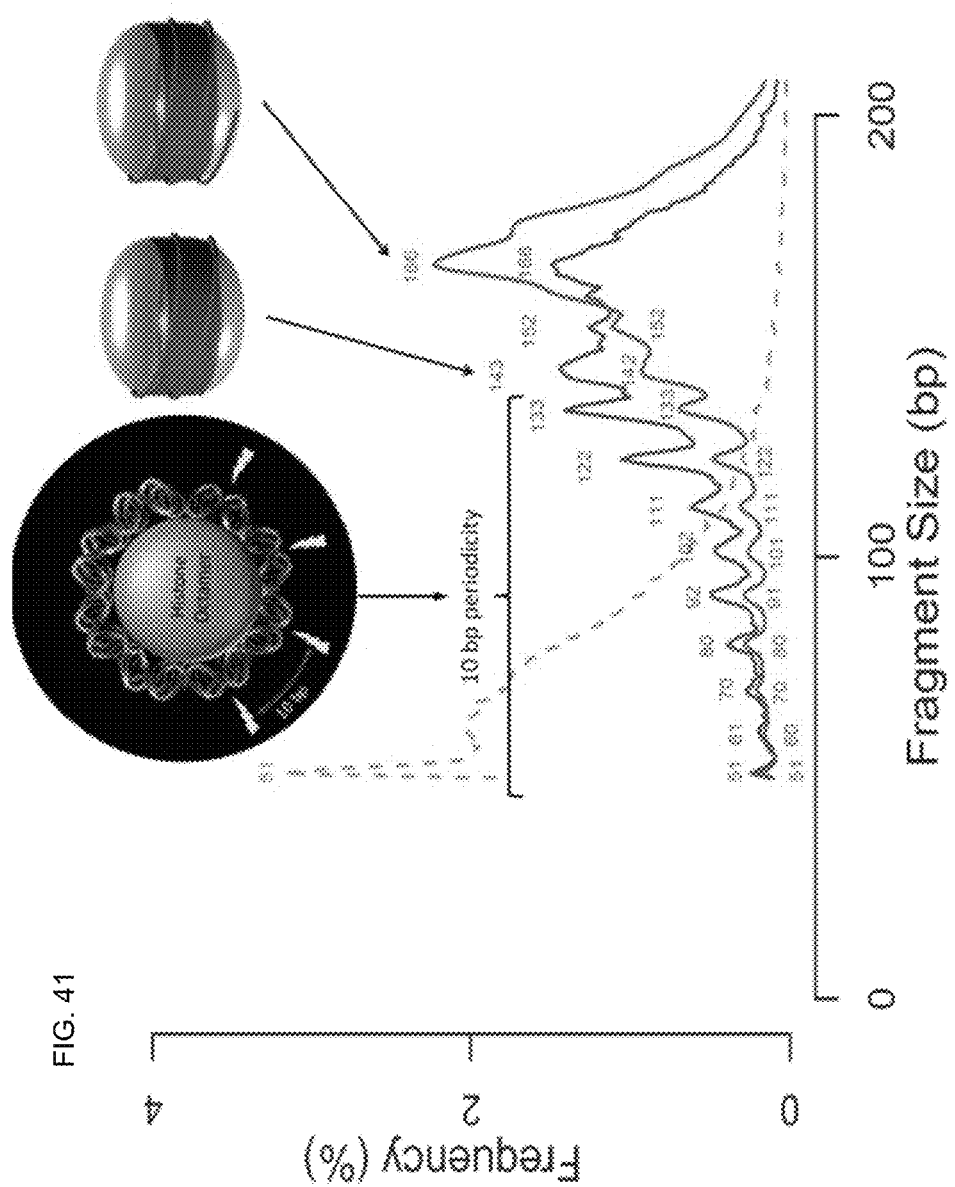
FIG. 41 shows a plot of the sizes of the fetal and total sequences for the whole genome.
Figure 42A:
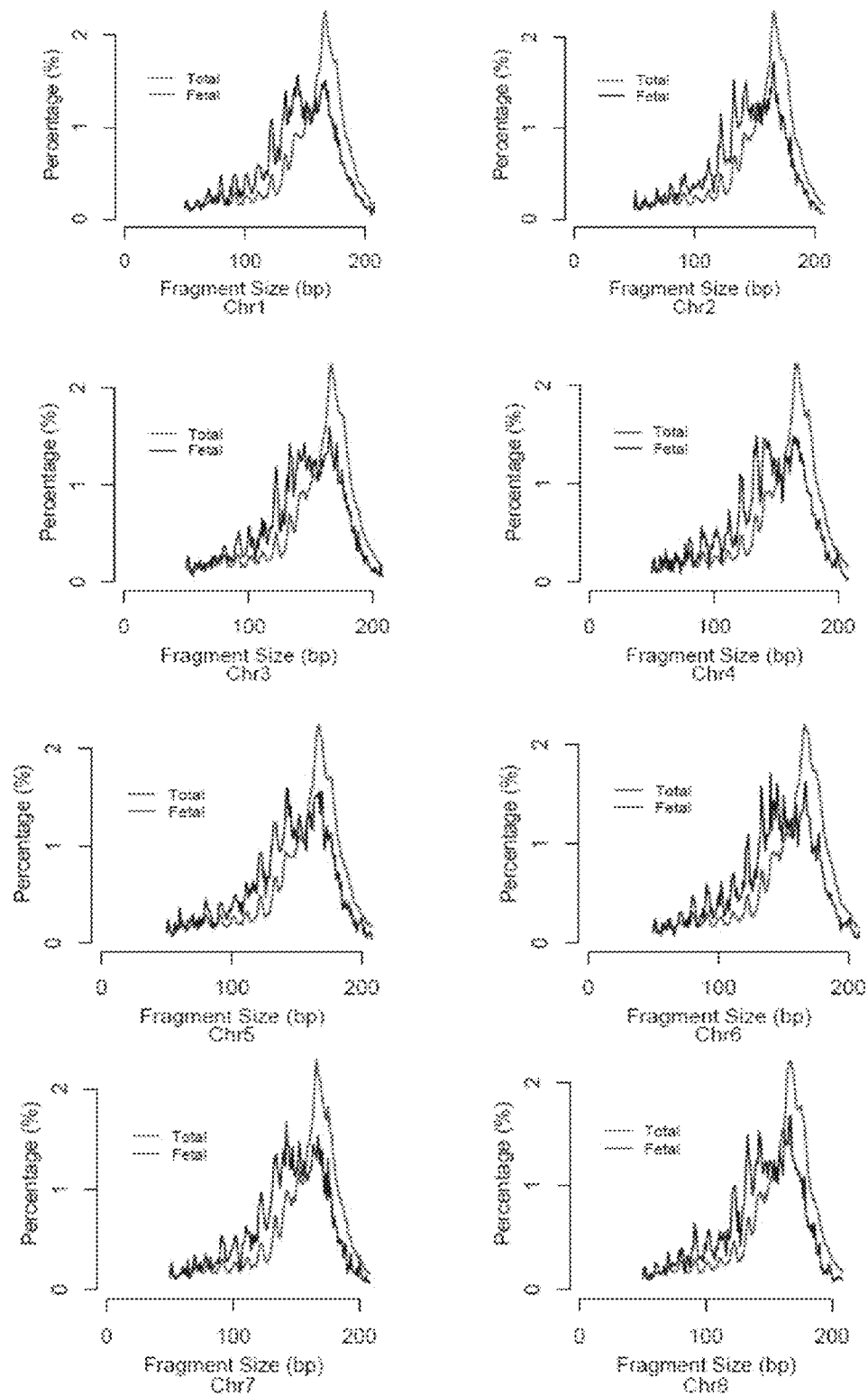
FIG. 42A-42C shows similar plots individually for each chromosome according to embodiments of the present invention.
Figure 42B:
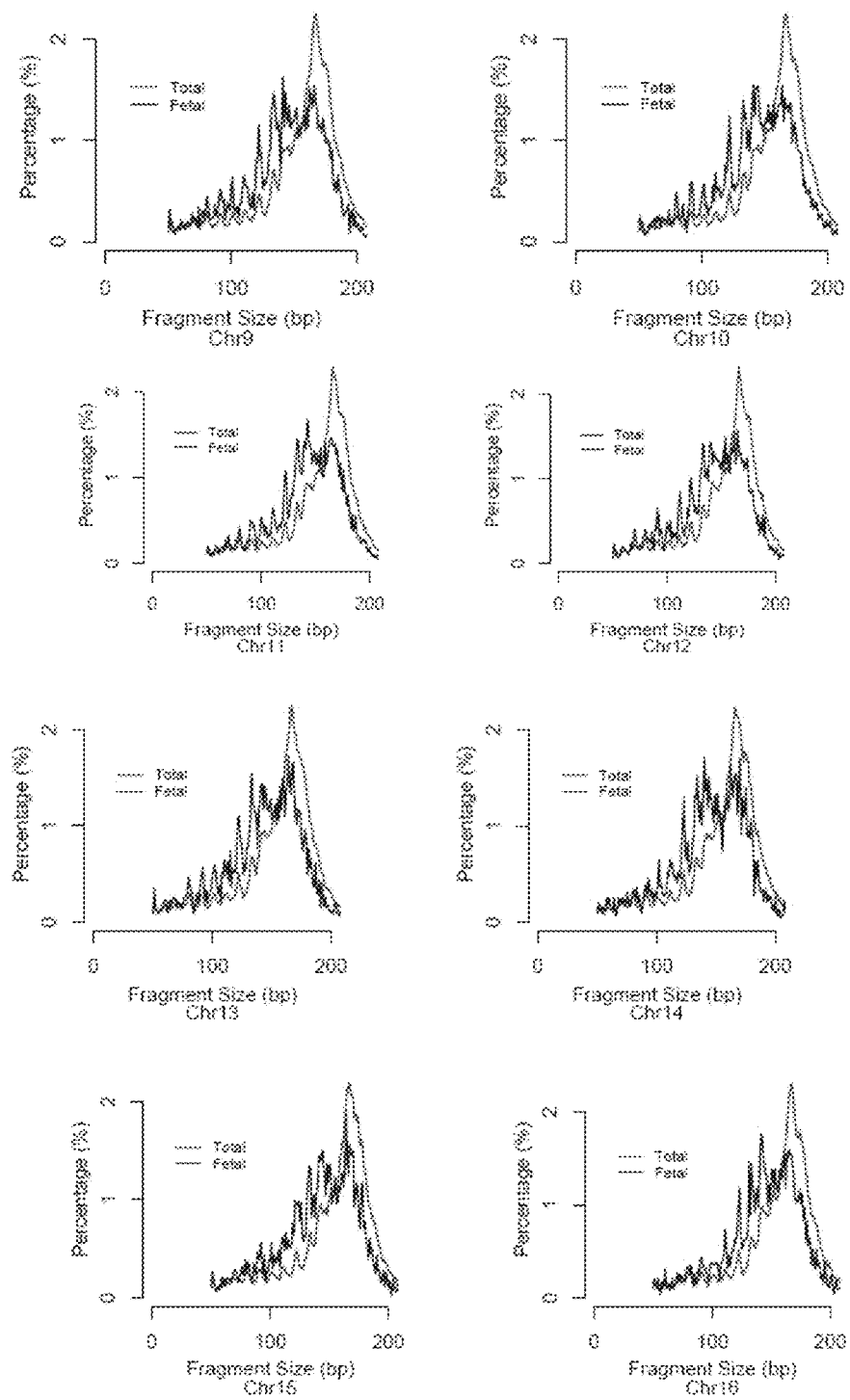
Figure 42C:
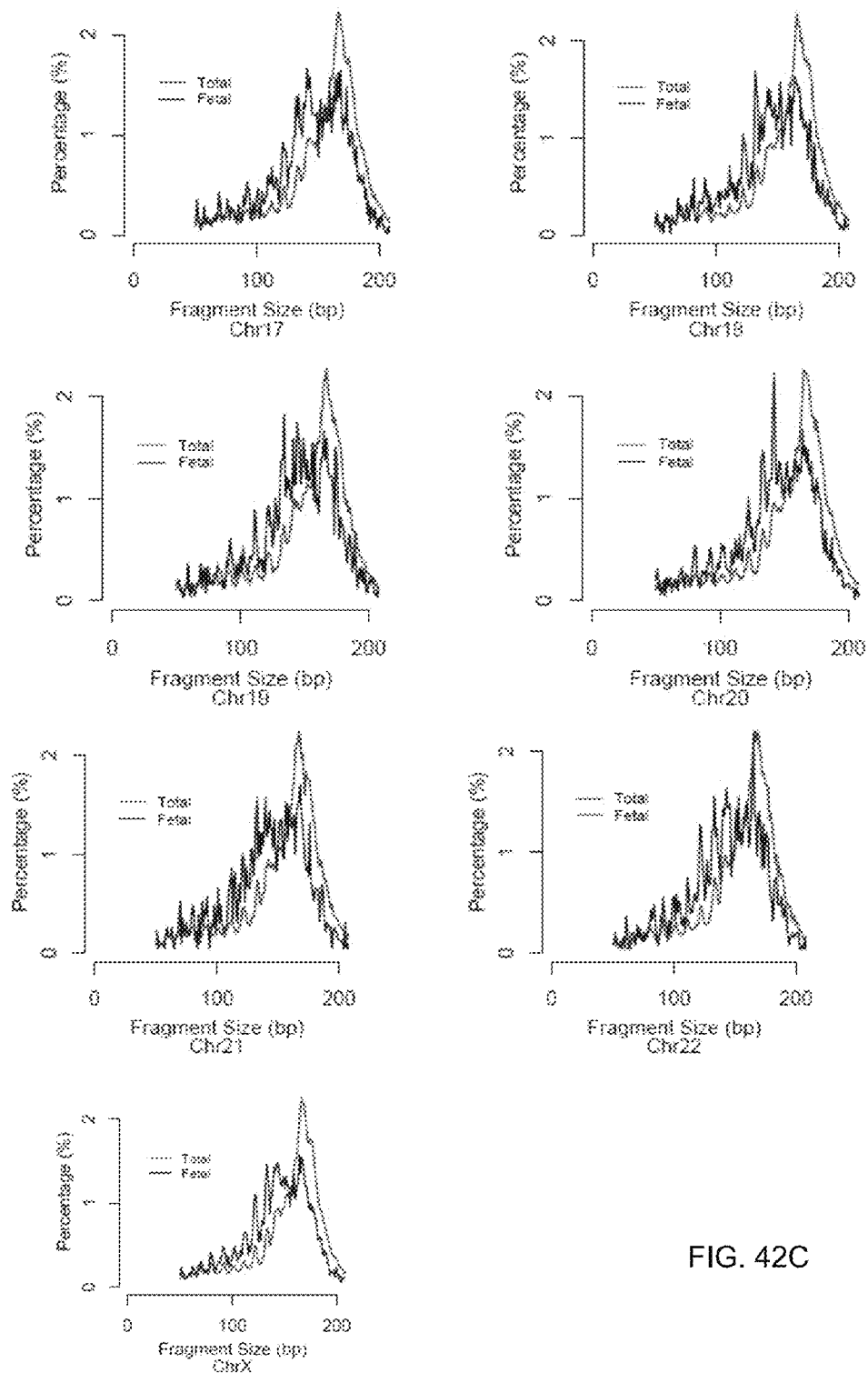

We observed that the most significant differences between fetal and maternal DNA in maternal plasma is the reduction in the 166 bp peak, relative to the 143 bp peak (FIG. 41). The most abundant total sequences (predominantly maternal) were 166 bp in length. The most significant difference in the size distribution between the fetal and total DNA was that fetal DNA exhibited a reduction in the 166 bp peak (FIG. 41) and a relative prominence of the 143 bp peak. The latter likely corresponded to the trimming of a ~20-bp linker fragment from a nucleosome to its core particle of ~146 bp (Lewin B, in Gene IX, Jones and Bartlett, Sudbury, 2008, pp. 757-795).

From approximately 143 bp and below, the distributions of both fetal and total DNA demonstrated a 10 bp periodicity reminiscent of nuclease-cleaved nucleosomes. These data suggest that plasma DNA fragments are derived from apoptotic enzymatic processing. In contrast, size analysis of reads that mapped to the non-histone bound mitochondrial genome did not show this nucleosomal pattern (FIG. 41). These results provide a previously unknown molecular explanation for the known size differences between fetal and maternal DNA using Y chromosome and selected polymorphic genetic markers (Chan K C A et al Clin Chem 2004; 50: 88-92; Li et al Clin Chem 2004; 50: 1002-1011; US Patent Application 20050164241; US Patent application 20070202525), and show that such size differences exist across the entire genome. The most likely explanation of this difference is that circulating fetal DNA molecules consist of more molecules in which the ~20 bp linker fragment has been trimmed from a nucleosome.

Given these observations, there are a number of ways in which the sample can be enriched for fetal DNA. In one embodiment, one can use reagents that would preferentially bind to the linker fragment. Such reagents would be expected to bind preferentially to maternal-derived DNA when compared with fetal-derived DNA in maternal plasma. One example of such reagents is an antibody. One target of such an antibody is one that binds to histone H1. Histone H1 is known to bind to the linker fragment. One application of such an antibody is for performing enrichment of fetal DNA by negative selection, i.e., via the preferential immunoprecipitation of the maternally-derived DNA in maternal plasma that contains the linker, histone H1-containing, fragment. Furthermore, H1 is known to have a number of variants, some of them exhibiting tissue-specific variation in expression (Sancho M et al PLoS Genet 2008; 4: e1000227). These variants might be further exploited to differentiate the fetal (predominantly placental) and maternal (predominantly hematopoietic (Lui Y Y N et al Clin Chem 2002; 48: 421-427) DNA. For example, one can target a histone H1 variant that is predominantly expressed by trophoblastic cells to preferentially and positively select for fetal-derived DNA in maternal plasma. This strategy can also be applied for other histone proteins or other nucleosomal proteins that exhibit tissue-specific, especially trophoblast-specific, patterns of expression.

Given the sharp 166 bp peak for maternal DNA, another possibility for enriching fetal DNA is to design a system for negative selection of DNA fragments that are of 166±2 bp in length. For example, a system based on capillary electrophoresis or high performance liquid chromatography could allow precise size measurement and separation of DNA molecules. Another way for negative selection is to do this in silico during the bioinformatic analysis of the sequencing data.

As other DNA species in plasma, e.g. tumor DNA (Vlassov V V et al. Curr Mol Med 2010; 10: 142-165) and transplanted organ DNA (Lo Y M D et al Lancet 1998; 351: 1329-1330), is also expected to share such features with fetal DNA in maternal plasma, the strategies listed in (1) and (2) above could also be used for the enrichment of these DNA species.

According to one embodiment, a method for the differential enrichment of DNA species in human plasma or serum through the targeting of the linker fragment of the nucleosomes is provided. In an embodiment, the enrichment is made by removing one of the following: maternally-derived DNA or DNA derived from hematopoietic cells. In another embodiment, the targeting involves a reagent (such as an antibody or another type of protein) that would bind preferentially to a protein or nucleic acid component of the linker fragment of the nucleosome. In another embodiment, the targeting reagent will selectively bind to histone H1 or another protein that binds to the linker fragment of the nucleosome. In another embodiment, the targeting reagent will bind to maternal or hematological variants of histone H1 or another protein that binds to the linker fragment of the nucleosome. In one embodiment, the removal of the DNA is carried out by immunoprecipitation or binding to a solid surface.

According to another embodiment, a method for the differential enrichment of fetal DNA in maternal plasma or serum includes: (a) use of an antibody that would bind to one or more components of the linker fragment of the nucleosome; (b) remove the bound fraction by immunoprecipitation or capture to a solid surface; and (c) harvest the unbound fraction which contains an increased fractional concentration of fetal DNA.

Any of the software components or functions described in this application, may be implemented as software code to be executed by a processor using any suitable computer language such as, for example, Java, C++ or Perl using, for example, conventional or object-oriented techniques. The software code may be stored as a series of instructions, or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer program product (e.g. a hard drive or an entire computer system), and may be present on or within different computer program products within a system or network. A computer system may include a monitor, printer, or other suitable display for providing any of the results mentioned herein to a user.

Figure 43:
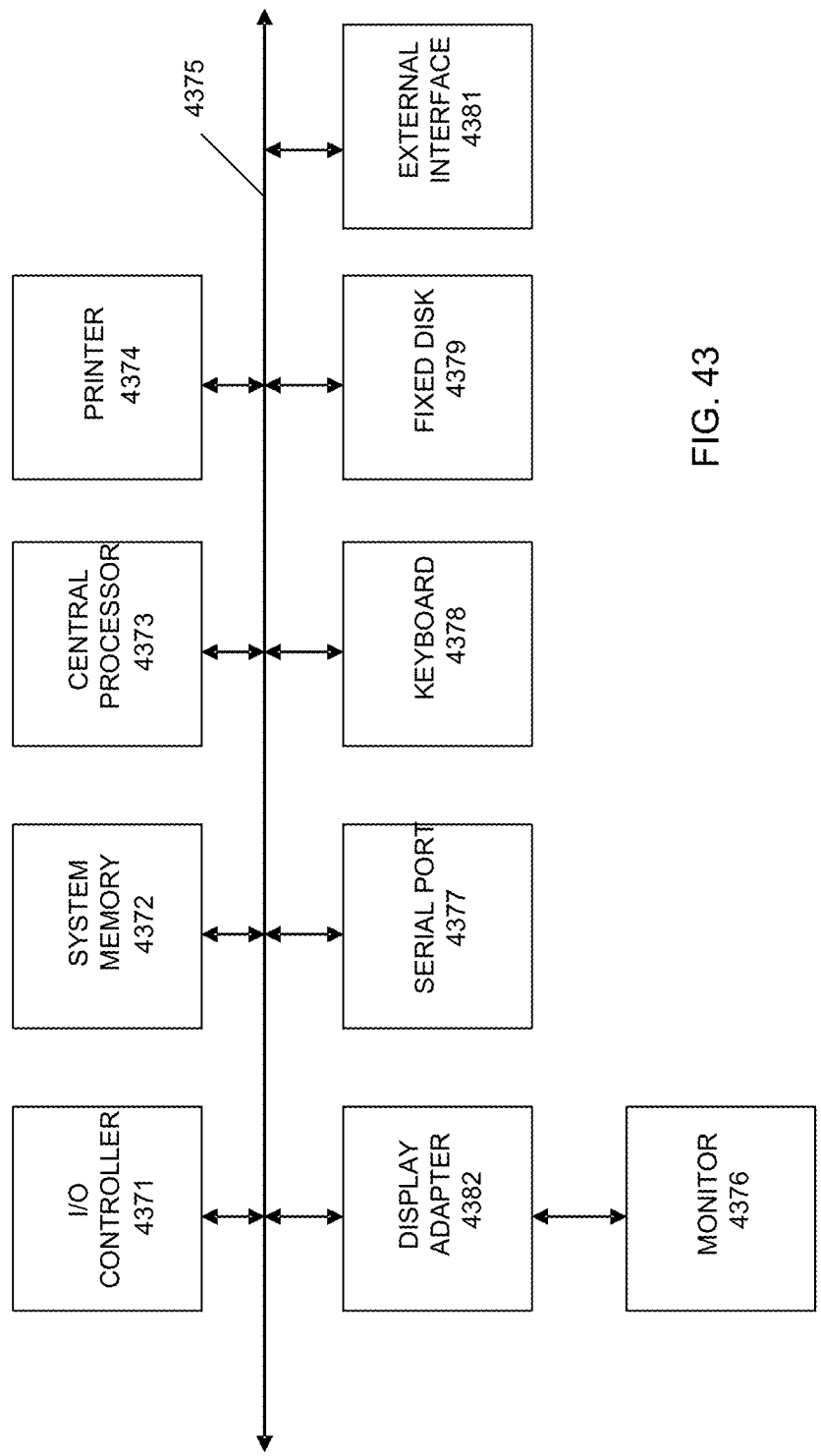
FIG. 43 shows a block diagram of an example computer system 4300 usable with system and methods according to embodiments of the present invention.

An example of a computer system is shown in FIG. 43. The subsystems shown in FIG. 43 are interconnected via a system bus 4375. Additional subsystems such as a printer 4374, keyboard 4378, fixed disk 4379, monitor 4376, which is coupled to display adapter 4382, and others are shown. Peripherals and input/output (I/O) devices, which couple to I/O controller 4371, can be connected to the computer system by any number of means known in the art, such as serial port 4377. For example, serial port 4377 or external interface 4381 can be used to connect the computer apparatus to a wide area network such as the Internet, a mouse input device, or a scanner. The interconnection via system bus allows the central processor 4373 to communicate with each subsystem and to control the execution of instructions from system memory 4372 or the fixed disk 4379, as well as the exchange of information between subsystems. The system memory 4372 and/or the fixed disk 4379 may embody a computer readable medium. Any of the values mentioned herein can be output from one component to another component and can be output to the user.

A computer system can include a plurality of the same components or subsystems, e.g., connected together by external interface 4381 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

The specific details of particular embodiments may be combined in any suitable manner or varied from those shown and described herein without departing from the spirit and scope of embodiments of the invention.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

All publications, patents, and patent applications cited herein are hereby incorporated by reference in their entirety for all purposes.

What is claimed is:

1. A method of determining a first proportion of a fetal genome that has been sequenced from a biological sample obtained from a pregnant female, the fetus having a father and a mother being the pregnant female, the father having a paternal genome and the mother having a maternal genome, wherein the sample contains a mixture of maternal and fetal nucleic acids, the method comprising:

receiving sequencing results of a sequencing of a plurality of nucleic acid molecules from the biological sample obtained from the pregnant female;

analyzing the sequencing results, the analyzing for a nucleic acid molecule including:
identifying a location of the nucleic acid molecule in a human genome; and
determining a respective allele of the nucleic acid molecule;

determining a first plurality of loci, wherein the fetal genome is heterozygous at each loci of the first plurality such that the fetal genome has a respective first and second allele at that loci, and wherein the maternal genome is homozygous at each loci of the first plurality such that the maternal genome has two of the respective second allele at that loci, the first allele being different than the second allele;

determining, with a computer system, a second proportion of loci of the first plurality of loci in which a respective first allele is detected from the sequencing results;

based on the second proportion, determining the first proportion of the fetal genome that has been sequenced from the biological sample;

determining that a threshold amount of sequencing has not been performed based on the first proportion of the fetal genome that has been sequenced from the biological sample; and performing more sequencing in response to the threshold amount of sequencing having not been reached.

2. The method of claim 1, wherein identifying the location of a nucleic acid molecule in the human genome includes mapping a sequence of the nucleic acid molecule to the human genome.

3. The method of claim 1, wherein determining the first plurality of loci includes:

for each loci of the first plurality:
determining the paternal genome is homozygous for the respective first allele; and
determining the maternal genome is homozygous for the respective second allele.

4. The method of claim 1, wherein determining a specific locus to be one of the first plurality of loci includes:

determining a cutoff value for a number of predicted counts of the respective first allele at the specific locus, the cutoff value predicting whether the maternal genome is homozygous and the fetal genome is heterozygous, wherein the cutoff value is determined based on an expected distribution of numbers of counts for different combinations of homozygosity and heterozygosity at the specific locus;

based on the analysis of the sequencing results, detecting the respective first and second alleles at the specific locus;

determining a number of actual counts of the respective first allele based on the sequencing of the plurality of nucleic acid molecules from the biological sample; and determining the fetal genome is heterozygous for the respective first and second allele and the maternal genome is homozygous for the respective second allele when the number of actual counts is less than the cutoff value.

5. The method of claim 4, wherein the statistical distribution is dependent on a fractional concentration of nucleic acid molecules from the biological sample that are derived from the fetus.

6. The method of claim 5, wherein the statistical distribution is further dependent on the number of the plurality of nucleic acid molecules corresponding to the specific locus.

7. The method of claim 1, wherein the respective first allele of at least two loci of the first plurality are different from each other.

8. The method of claim 1, wherein the first proportion equals the second proportion.

9. The method of claim 1, wherein the first proportion is a percentage.

10. The method of claim 1, wherein the first proportion is a range, where the second proportion is one end of the range.

11. The method of claim 1, wherein the first plurality of loci are on a first chromosome, and wherein the first proportion is a proportion of the first chromosome that has been sequenced from the biological sample.

12. The method of claim 11, further comprising;
determining a proportion of each chromosome of the fetal genome that has been sequenced from the biological sample.

13. A computer product comprising a non-transitory computer readable medium storing a plurality of instructions that when executed control a computer system to determine a first proportion of a fetal genome that has been sequenced from a biological sample obtained from a pregnant female, the fetus having a father and a mother being the pregnant female, the father having a paternal genome and the mother having a maternal genome, wherein the sample contains a mixture of maternal and fetal nucleic acids, the instructions comprising:
receiving sequencing results of a sequencing of a plurality of nucleic acid molecules from the biological sample obtained from the pregnant female;
analyzing the sequencing results, the analyzing for a nucleic acid molecule including:
identifying a location of the nucleic acid molecule in a human genome; and
determining a respective allele of the nucleic acid molecule;
determining a first plurality of loci, wherein the fetal genome is heterozygous at each loci of the first plurality such that the fetal genome has a respective first and second allele at that loci, and wherein the maternal genome is homozygous at each loci of the first plurality such that the maternal genome has two of the respective second allele at that loci, the first allele being different than the second allele;
determining a second proportion of loci of the first plurality of loci in which a respective first allele is detected from the sequencing results;
based on the second proportion, determining the first proportion of the fetal genome that has been sequenced from the biological sample;
determining that a threshold amount of sequencing has not been performed based on the first proportion of the fetal genome that has been sequenced from the biological sample; and
directing a machine to perform more sequencing in response to the threshold amount of sequencing having not been reached.

14. The computer product of claim 13, wherein determining the first plurality of loci includes:
for each loci of the first plurality:
determining the paternal genome is homozygous for the respective first allele; and
determining the maternal genome is homozygous for the respective second allele.

15. The computer product of claim 13, wherein determining a specific locus to be one of the first plurality of loci includes:
determining a cutoff value for a number of predicted counts of the respective first allele at the specific locus, the cutoff value predicting whether the maternal genome is homozygous and the fetal genome is heterozygous, wherein the cutoff value is determined based on an expected distribution of numbers of counts for different combinations of homozygosity and heterozygosity at the specific locus;
based on the analysis of the sequencing results, detecting the respective first and second alleles at the specific locus;
determining a number of actual counts of the respective first allele based on the sequencing of the plurality of nucleic acid molecules from the biological sample; and
determining the fetal genome is heterozygous for the respective first and second allele and the maternal genome is homozygous for the respective second allele when the number of actual counts is less than the cutoff value.

16. The computer product of claim 15, wherein the statistical distribution is dependent on a fractional concentration of nucleic acid molecules from the biological sample that are derived from the fetus.

17. The computer product of claim 16, wherein the statistical distribution is further dependent on the number of the plurality of nucleic acid molecules corresponding to the specific locus.

18. The computer product of claim 13, wherein the first plurality of loci are on a first chromosome, and wherein the first proportion is a proportion of the first chromosome that has been sequenced from the biological sample.

19. The computer product of claim 18, wherein the instructions further comprise;
determining a proportion of each chromosome of the fetal genome that has been sequenced from the biological sample.

* * * * *

SEQUENCE LISTING

```
<160> NUMBER OF SEQ ID NOS: 52

<210> SEQ ID NO 1
<211> LENGTH: 14
<212> TYPE: DNA
<213> ORGANISM: Artificial Sequence
<220> FEATURE:
<223> OTHER INFORMATION: synthetic haplotype A (Hap A)

<400> SEQUENCE: 1
acgatacgat taag                                                       14

<210> SEQ ID NO 2
<211> LENGTH: 14
<212> TYPE: DNA
<213> ORGANISM: Artificial Sequence
<220> FEATURE:
<223> OTHER INFORMATION: synthetic haplotype B (Hap B)

<400> SEQUENCE: 2
cggtagcctt atcg                                                       14
```

```
<210> SEQ ID NO 3
<211> LENGTH: 14
<212> TYPE: DNA
<213> ORGANISM: Artificial Sequence
<220> FEATURE:
<223> OTHER INFORMATION: synthetic haplotype C (Hap C)

<400> SEQUENCE: 3
ccattgtcag ttca                                                    14

<210> SEQ ID NO 4
<211> LENGTH: 14
<212> TYPE: DNA
<213> ORGANISM: Artificial Sequence
<220> FEATURE:
<223> OTHER INFORMATION: synthetic maternal genotypes

<400> SEQUENCE: 4
msgwwrcswt wwmg                                                    14

<210> SEQ ID NO 5
<211> LENGTH: 50
<212> TYPE: DNA
<213> ORGANISM: Artificial Sequence
<220> FEATURE:
<223> OTHER INFORMATION: synthetic read with codons 41/42 paternally
      inherited mutation

<400> SEQUENCE: 5
cgggtattgt cgtagtcctc acctgtctag gggtttcctg agttggagac              50

<210> SEQ ID NO 6
<211> LENGTH: 50
<212> TYPE: DNA
<213> ORGANISM: Artificial Sequence
<220> FEATURE:
<223> OTHER INFORMATION: synthetic read with codons 41/42 paternally
      inherited mutation

<400> SEQUENCE: 6
gggtattgtc gtagtcctca cctgtctagg ggtttcctga gttggagacc              50

<210> SEQ ID NO 7
<211> LENGTH: 50
<212> TYPE: DNA
<213> ORGANISM: Artificial Sequence
<220> FEATURE:
<223> OTHER INFORMATION: synthetic read with codons 41/42 paternally
      inherited mutation

<400> SEQUENCE: 7
ggtattgtcg tagtcctcac ctgtctaggg gtttcctgag ttggagaccc              50

<210> SEQ ID NO 8
<211> LENGTH: 50
<212> TYPE: DNA
<213> ORGANISM: Artificial Sequence
<220> FEATURE:
<223> OTHER INFORMATION: synthetic read with codons 41/42 paternally
      inherited mutation

<400> SEQUENCE: 8
cgtagtcctc acctgtctag gggtttcctg agttggagac ccaggttccc              50
```

-continued

```
<210> SEQ ID NO 9
<211> LENGTH: 50
<212> TYPE: DNA
<213> ORGANISM: Artificial Sequence
<220> FEATURE:
<223> OTHER INFORMATION: synthetic read with codons 41/42 paternally
      inherited mutation

<400> SEQUENCE: 9
gtagtcctca cctgtctagg ggtttcctga gttggagacc caggttccca              50

<210> SEQ ID NO 10
<211> LENGTH: 50
<212> TYPE: DNA
<213> ORGANISM: Artificial Sequence
<220> FEATURE:
<223> OTHER INFORMATION: synthetic read with codons 41/42 paternally
      inherited mutation

<400> SEQUENCE: 10
ctgtctaggg gtttcctgag ttggagaccc aggttcccat ctggtggtcg              50

<210> SEQ ID NO 11
<211> LENGTH: 50
<212> TYPE: DNA
<213> ORGANISM: Artificial Sequence
<220> FEATURE:
<223> OTHER INFORMATION: synthetic read with codons 41/42 paternally
      inherited mutation

<400> SEQUENCE: 11
tgtctagggg tttcctgagt tggagaccca ggttcccatc tggtggtcgt              50

<210> SEQ ID NO 12
<211> LENGTH: 50
<212> TYPE: DNA
<213> ORGANISM: Artificial Sequence
<220> FEATURE:
<223> OTHER INFORMATION: synthetic read with codons 41/42 paternally
      inherited mutation

<400> SEQUENCE: 12
ttcctgagtg ggagacccag gttcccatct ggtggtcgtc ggattcccac              50

<210> SEQ ID NO 13
<211> LENGTH: 50
<212> TYPE: DNA
<213> ORGANISM: Artificial Sequence
<220> FEATURE:
<223> OTHER INFORMATION: synthetic read with codons 41/42 paternally
      inherited mutation

<400> SEQUENCE: 13
gtgggagacc caggttccca tctggtggtc gtcggattcc cacccttta               50

<210> SEQ ID NO 14
<211> LENGTH: 44
<212> TYPE: DNA
<213> ORGANISM: Artificial Sequence
<220> FEATURE:
<223> OTHER INFORMATION: synthetic read with codons 41/42 wildtype
      sequence

<400> SEQUENCE: 14
gtattgtcgt agtcctcacc tgtctagggg tttcctgagt ttct                    44
```

```
<210> SEQ ID NO 15
<211> LENGTH: 45
<212> TYPE: DNA
<213> ORGANISM: Artificial Sequence
<220> FEATURE:
<223> OTHER INFORMATION: synthetic read with codons 41/42 wildtype
      sequence

<400> SEQUENCE: 15
gtattgtcgt agtcctcacc tgtctagggg tttcctgagt ttctt                    45

<210> SEQ ID NO 16
<211> LENGTH: 46
<212> TYPE: DNA
<213> ORGANISM: Artificial Sequence
<220> FEATURE:
<223> OTHER INFORMATION: synthetic read with codons 41/42 wildtype
      sequence

<400> SEQUENCE: 16
gtattgtcgt agtcctcacc tgtctagggg tttcctgagt ttcttg                   46

<210> SEQ ID NO 17
<211> LENGTH: 47
<212> TYPE: DNA
<213> ORGANISM: Artificial Sequence
<220> FEATURE:
<223> OTHER INFORMATION: synthetic read with codons 41/42 wildtype
      sequence

<400> SEQUENCE: 17
gtattgtcgt agtcctcacc tgtctagggg tttcctgagt ttcttgg                  47

<210> SEQ ID NO 18
<211> LENGTH: 47
<212> TYPE: DNA
<213> ORGANISM: Artificial Sequence
<220> FEATURE:
<223> OTHER INFORMATION: synthetic read with codons 41/42 wildtype
      sequence

<400> SEQUENCE: 18
gtatcgtcgt agtcctcacc tgtctagggg tttcctgagt ttcttgg                  47

<210> SEQ ID NO 19
<211> LENGTH: 48
<212> TYPE: DNA
<213> ORGANISM: Artificial Sequence
<220> FEATURE:
<223> OTHER INFORMATION: synthetic read with codons 41/42 wildtype
      sequence

<400> SEQUENCE: 19
gtattgtcgt agtcctcacc tgtctagggg tttcctgagt ttcttgga                 48

<210> SEQ ID NO 20
<211> LENGTH: 49
<212> TYPE: DNA
<213> ORGANISM: Artificial Sequence
<220> FEATURE:
<223> OTHER INFORMATION: synthetic read with codons 41/42 wildtype
      sequence

<400> SEQUENCE: 20
gtattgtcgt agtcctcacc tgtctagggg tttcctgagt ttcttggag                49
```

```
<210> SEQ ID NO 21
<211> LENGTH: 50
<212> TYPE: DNA
<213> ORGANISM: Artificial Sequence
<220> FEATURE:
<223> OTHER INFORMATION: synthetic read with codons 41/42 wildtype
      sequence

<400> SEQUENCE: 21
tattgtcgta gtcctcacct gtctaggggt ttcctgagtt tcttggagac            50

<210> SEQ ID NO 22
<211> LENGTH: 50
<212> TYPE: DNA
<213> ORGANISM: Artificial Sequence
<220> FEATURE:
<223> OTHER INFORMATION: synthetic read with codons 41/42 wildtype
      sequence

<400> SEQUENCE: 22
attgtcgtag tcctcacctg tctaggggtt tcctgagttt cttggagacc            50

<210> SEQ ID NO 23
<211> LENGTH: 50
<212> TYPE: DNA
<213> ORGANISM: Artificial Sequence
<220> FEATURE:
<223> OTHER INFORMATION: synthetic read with codons 41/42 wildtype
      sequence

<400> SEQUENCE: 23
ttgtcgtagt cctcacctgt ctaggggttt cctgagtttc ttggagaccc            50

<210> SEQ ID NO 24
<211> LENGTH: 50
<212> TYPE: DNA
<213> ORGANISM: Artificial Sequence
<220> FEATURE:
<223> OTHER INFORMATION: synthetic read with codons 41/42 wildtype
      sequence

<400> SEQUENCE: 24
tcgtagtcct cacctgtcta ggggtttcct gagtttcttg gagacccagg            50

<210> SEQ ID NO 25
<211> LENGTH: 50
<212> TYPE: DNA
<213> ORGANISM: Artificial Sequence
<220> FEATURE:
<223> OTHER INFORMATION: synthetic read with codons 41/42 wildtype
      sequence

<400> SEQUENCE: 25
tcggagtcct cacctgtcta ggggtttcct gagtttcttg gagacccagg            50

<210> SEQ ID NO 26
<211> LENGTH: 50
<212> TYPE: DNA
<213> ORGANISM: Artificial Sequence
<220> FEATURE:
<223> OTHER INFORMATION: synthetic read with codons 41/42 wildtype
      sequence

<400> SEQUENCE: 26
cgtagtcctc acctgtctag ggtttcctg agtttcttgg agacccaggt            50
```

```
<210> SEQ ID NO 27
<211> LENGTH: 50
<212> TYPE: DNA
<213> ORGANISM: Artificial Sequence
<220> FEATURE:
<223> OTHER INFORMATION: synthetic read with codons 41/42 wildtype
      sequence

<400> SEQUENCE: 27
gtagtcctca cctgtctagg ggtttcctga gtttcttgga gacccaggtt            50

<210> SEQ ID NO 28
<211> LENGTH: 50
<212> TYPE: DNA
<213> ORGANISM: Artificial Sequence
<220> FEATURE:
<223> OTHER INFORMATION: synthetic read with codons 41/42 wildtype
      sequence

<400> SEQUENCE: 28
tagtcctcac ctgtctaggg gtttcctgag tttcttggag acccaggttc            50

<210> SEQ ID NO 29
<211> LENGTH: 50
<212> TYPE: DNA
<213> ORGANISM: Artificial Sequence
<220> FEATURE:
<223> OTHER INFORMATION: synthetic read with codons 41/42 wildtype
      sequence

<400> SEQUENCE: 29
agtcctcacc tgtctagggg tttcctgagt tcttggaga cccaggttcc             50

<210> SEQ ID NO 30
<211> LENGTH: 50
<212> TYPE: DNA
<213> ORGANISM: Artificial Sequence
<220> FEATURE:
<223> OTHER INFORMATION: synthetic read with codons 41/42 wildtype
      sequence

<400> SEQUENCE: 30
gtcctcacct gtctaggggt tcctgagtt tcttggagac ccaggttccc             50

<210> SEQ ID NO 31
<211> LENGTH: 50
<212> TYPE: DNA
<213> ORGANISM: Artificial Sequence
<220> FEATURE:
<223> OTHER INFORMATION: synthetic read with codons 41/42 wildtype
      sequence

<400> SEQUENCE: 31
gccctcacct gtctaggggt ttcctgagtt tcttggagac ccaggttccc            50

<210> SEQ ID NO 32
<211> LENGTH: 50
<212> TYPE: DNA
<213> ORGANISM: Artificial Sequence
<220> FEATURE:
<223> OTHER INFORMATION: synthetic read with codons 41/42 wildtype
      sequence

<400> SEQUENCE: 32
cctcacctgt ctaggggttt cctgagtttc ttggagaccc aggttcccat            50
```

<210> SEQ ID NO 33
<211> LENGTH: 50
<212> TYPE: DNA
<213> ORGANISM: Artificial Sequence
<220> FEATURE:
<223> OTHER INFORMATION: synthetic read with codons 41/42 wildtype
      sequence

<400> SEQUENCE: 33
tcacctgtct aggggtttcc tgagtttctt ggagacccag gttcccatct            50

<210> SEQ ID NO 34
<211> LENGTH: 50
<212> TYPE: DNA
<213> ORGANISM: Artificial Sequence
<220> FEATURE:
<223> OTHER INFORMATION: synthetic read with codons 41/42 wildtype
      sequence

<400> SEQUENCE: 34
acgtgtctag gggtttcctg agtttcttgg agacccaggt tcccatctgg            50

<210> SEQ ID NO 35
<211> LENGTH: 50
<212> TYPE: DNA
<213> ORGANISM: Artificial Sequence
<220> FEATURE:
<223> OTHER INFORMATION: synthetic read with codons 41/42 wildtype
      sequence

<400> SEQUENCE: 35
acctgtctag gggtttcctg agtttcttgg agacccaggt tcccatctgg            50

<210> SEQ ID NO 36
<211> LENGTH: 50
<212> TYPE: DNA
<213> ORGANISM: Artificial Sequence
<220> FEATURE:
<223> OTHER INFORMATION: synthetic read with codons 41/42 wildtype
      sequence

<400> SEQUENCE: 36
cctgtctagg ggtttcctga gtttcttgga gacccaggtt cccatctggt            50

<210> SEQ ID NO 37
<211> LENGTH: 50
<212> TYPE: DNA
<213> ORGANISM: Artificial Sequence
<220> FEATURE:
<223> OTHER INFORMATION: synthetic read with codons 41/42 wildtype
      sequence

<400> SEQUENCE: 37
gtctaggggt tcctgagtt tcttggagac ccaggttccc atctggtggt             50

<210> SEQ ID NO 38
<211> LENGTH: 50
<212> TYPE: DNA
<213> ORGANISM: Artificial Sequence
<220> FEATURE:
<223> OTHER INFORMATION: synthetic read with codons 41/42 wildtype
      sequence

<400> SEQUENCE: 38
ctaggggttt cctgagtttc ttggagaccc aggttcccat ctggtggtcg            50

```
<210> SEQ ID NO 39
<211> LENGTH: 50
<212> TYPE: DNA
<213> ORGANISM: Artificial Sequence
<220> FEATURE:
<223> OTHER INFORMATION: synthetic read with codons 41/42 wildtype
      sequence

<400> SEQUENCE: 39
aggggtttcc tgagtttctt ggagacccag gttcccatct ggtggtcgtc          50

<210> SEQ ID NO 40
<211> LENGTH: 50
<212> TYPE: DNA
<213> ORGANISM: Artificial Sequence
<220> FEATURE:
<223> OTHER INFORMATION: synthetic read with codons 41/42 wildtype
      sequence

<400> SEQUENCE: 40
aggggtttcc tgagtttctg ggagacccag gttcccatct gggggtcgtc          50

<210> SEQ ID NO 41
<211> LENGTH: 50
<212> TYPE: DNA
<213> ORGANISM: Artificial Sequence
<220> FEATURE:
<223> OTHER INFORMATION: synthetic read with codons 41/42 wildtype
      sequence

<400> SEQUENCE: 41
ggggtttcct gagtttcttg gagacccagg ttcccatctg gtggtcgtcg          50

<210> SEQ ID NO 42
<211> LENGTH: 50
<212> TYPE: DNA
<213> ORGANISM: Artificial Sequence
<220> FEATURE:
<223> OTHER INFORMATION: synthetic read with codons 41/42 wildtype
      sequence

<400> SEQUENCE: 42
gggtttcctg agtttcttgg agacccaggt tcccatctgg tggtcgtcgg          50

<210> SEQ ID NO 43
<211> LENGTH: 50
<212> TYPE: DNA
<213> ORGANISM: Artificial Sequence
<220> FEATURE:
<223> OTHER INFORMATION: synthetic read with codons 41/42 wildtype
      sequence

<400> SEQUENCE: 43
ggtttcctga gtttcttgga gacccaggtt cccatctggt ggtcgtcgga          50

<210> SEQ ID NO 44
<211> LENGTH: 50
<212> TYPE: DNA
<213> ORGANISM: Artificial Sequence
<220> FEATURE:
<223> OTHER INFORMATION: synthetic read with codons 41/42 wildtype
      sequence

<400> SEQUENCE: 44
gtttcctgat tttcttggag acccagggtc ccatctggtg gtcgtcggat          50
```

<210> SEQ ID NO 45
<211> LENGTH: 50
<212> TYPE: DNA
<213> ORGANISM: Artificial Sequence
<220> FEATURE:
<223> OTHER INFORMATION: synthetic read with codons 41/42 wildtype
      sequence

<400> SEQUENCE: 45
gtttcctgag tttcttggag acccaggttc ccatctggtg gtcgtcggat         50

<210> SEQ ID NO 46
<211> LENGTH: 50
<212> TYPE: DNA
<213> ORGANISM: Artificial Sequence
<220> FEATURE:
<223> OTHER INFORMATION: synthetic read with codons 41/42 wildtype
      sequence

<400> SEQUENCE: 46
ttcctgagtt tcttggagac ccaggttccc atctggtggt cgtcggattc         50

<210> SEQ ID NO 47
<211> LENGTH: 50
<212> TYPE: DNA
<213> ORGANISM: Artificial Sequence
<220> FEATURE:
<223> OTHER INFORMATION: synthetic read with codons 41/42 wildtype
      sequence

<400> SEQUENCE: 47
cctgagtttc ttggagaccc aggttcccat ctggtggtcg tcggattccc         50

<210> SEQ ID NO 48
<211> LENGTH: 50
<212> TYPE: DNA
<213> ORGANISM: Artificial Sequence
<220> FEATURE:
<223> OTHER INFORMATION: synthetic read with codons 41/42 wildtype
      sequence

<400> SEQUENCE: 48
tgagtttctt ggagacccag gttcccatct ggtggtcgtc ggattcccac         50

<210> SEQ ID NO 49
<211> LENGTH: 50
<212> TYPE: DNA
<213> ORGANISM: Artificial Sequence
<220> FEATURE:
<223> OTHER INFORMATION: synthetic read with codons 41/42 wildtype
      sequence

<400> SEQUENCE: 49
tgagttcctt ggagacccag gttcccatct ggggtcgtc ggattcccac          50

<210> SEQ ID NO 50
<211> LENGTH: 50
<212> TYPE: DNA
<213> ORGANISM: Artificial Sequence
<220> FEATURE:
<223> OTHER INFORMATION: synthetic read with codons 41/42 wildtype
      sequence

<400> SEQUENCE: 50
gatgtccttg gagacccagg ttcccatctg ggggtcgtcg gattcccacc         50

```
<210> SEQ ID NO 51
<211> LENGTH: 50
<212> TYPE: DNA
<213> ORGANISM: Artificial Sequence
<220> FEATURE:
<223> OTHER INFORMATION: synthetic read with codons 41/42 wildtype
      sequence

<400> SEQUENCE: 51
gagtttgttg gagacccagg ttcccatctg ggggtcgtcg gattcccacc                50

<210> SEQ ID NO 52
<211> LENGTH: 50
<212> TYPE: DNA
<213> ORGANISM: Artificial Sequence
<220> FEATURE:
<223> OTHER INFORMATION: synthetic read with codons 41/42 wildtype
      sequence

<400> SEQUENCE: 52
gagtttcttg gagacccagg ttcccatctg gtggtcgtcg gattcccacc                50
```